United States Patent
Masakari et al.

(10) Patent No.: US 11,046,993 B2
(45) Date of Patent: Jun. 29, 2021

(54) GLUCOSE DEHYDROGENASE HAVING MODIFIED ELECTRON TRANSFER PROPERTIES, AND GLUCOSE MEASUREMENT METHOD

(71) Applicant: KIKKOMAN CORPORATION, Chiba (JP)

(72) Inventors: Yosuke Masakari, Chiba (JP); Seiichi Hara, Chiba (JP)

(73) Assignee: KIKKOMAN CORPORATION, Chiba (JP)

( * ) Notice: Subject to any disclaimer, the term of this patent is extended or adjusted under 35 U.S.C. 154(b) by 93 days.

(21) Appl. No.: 15/771,510

(22) PCT Filed: Oct. 31, 2016

(86) PCT No.: PCT/JP2016/082306
§ 371 (c)(1),
(2) Date: Apr. 27, 2018

(87) PCT Pub. No.: WO2017/073786
PCT Pub. Date: May 4, 2017

(65) Prior Publication Data
US 2018/0340211 A1    Nov. 29, 2018

(30) Foreign Application Priority Data
Oct. 30, 2015 (JP) .............. JP2015-214400

(51) Int. Cl.
| | |
|---|---|
| *C12Q 1/54* | (2006.01) |
| *G01N 33/66* | (2006.01) |
| *C12N 5/10* | (2006.01) |
| *G01N 27/327* | (2006.01) |
| *C12N 15/09* | (2006.01) |
| *C12M 1/34* | (2006.01) |
| *C12Q 1/32* | (2006.01) |
| *C12N 5/07* | (2010.01) |
| *C12N 9/02* | (2006.01) |

(52) U.S. Cl.
CPC ............. *C12Q 1/54* (2013.01); *C12M 1/34* (2013.01); *C12N 5/06* (2013.01); *C12N 5/10* (2013.01); *C12N 9/0004* (2013.01); *C12N 15/09* (2013.01); *C12Q 1/32* (2013.01); *G01N 27/327* (2013.01); *G01N 33/66* (2013.01)

(58) Field of Classification Search
CPC ... C12M 1/34; C12Q 1/32; C12Q 1/54; C12N 5/10; C12N 15/09; C12N 5/06; C12N 9/0004; G01N 33/66; G01N 27/327
See application file for complete search history.

(56) References Cited

U.S. PATENT DOCUMENTS 9,260,699 B2 *  2/2016  Sumida .............. C12Q 1/32
9,404,144 B2 *  8/2016  Sumida ............ C12N 9/0006
2004/0023330 A1  2/2004  Sode
2006/0258959 A1  11/2006  Sode
2014/0302542 A1  10/2014  Araki et al.

FOREIGN PATENT DOCUMENTS

| EP | 2719761 A1 | 4/2014 | |
|---|---|---|---|
| EP | 3456823 A1 | 3/2019 | |
| JP | 2012039949 A | 3/2012 | |
| JP | WO/2013/065770 * | 5/2013 | ............. C12N 15/09 |
| JP | WO/2016/076364 * | 5/2016 | ............... C12N 9/04 |
| WO | 2002036779 A1 | 5/2002 | |
| WO | 2002036779 A1 | 3/2004 | |
| WO | 2005023111 | 3/2005 | |
| WO | 2013065770 A1 | 5/2013 | |
| WO | 2013065770 A1 | 10/2013 | |
| WO | 2017/0195765 A1 | 11/2017 | |

OTHER PUBLICATIONS

Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*

(Continued)

*Primary Examiner* — Ganapathirama Raghu
(74) *Attorney, Agent, or Firm* — Lucas & Mercanti, LLP

(57) ABSTRACT

A glucose dehydrogenase having modified electron transfer properties, and a glucose measurement method and measuring kit using the glucose dehydrogenase are provided. Provided are a glucose dehydrogenase having at least 1, 2 or 3 amino acid substitutions, for example, amino acid substitution with a polar amino acid or alanine, in the region corresponding to the 457th to 477th position in SEQ ID NO: 1 of a glucose dehydrogenase having homology with SEQ ID NO: 1, a glucose measurement method, a measurement reagent kit and a sensor using the glucose dehydrogenase. The electron transfer properties of the glucose dehydrogenase of the present invention is modified and can be used in measuring glucose in the presence of a mediator with reduced concentration or in the absence of a mediator, and can be used, for example, in continuous glucose measurement.

12 Claims, 6 Drawing Sheets
Specification includes a Sequence Listing.

(56) References Cited

OTHER PUBLICATIONS

Chica et al., Semi-rational approaches to engineering enzyme activity: combining the benefits of directed evolution and rational design. Curr. Opi. Biotechnol., 2005, vol. 16: 378-384. (Year: 2005).*

Sen et al., Developments in directed evolution for enzyme functions. Appl. Biochem. Biotechnol., 2007, vol. 143: 212-223. (Year: 2007).*

Degani, Y. et al., "Direct Electrical Communication between Chemically Modified Enzymes and Metal Electrodes. a. Electron Transfer form Glucoze Oxidase to Metal Electrodes via Electron Relays, Bound Covalently to the Enzyme", The Journal of Physical Chemistry, vol. 91, No. 6, 1987 (pp. 1285-1289).

Wada, K., "Structural and Functional Analyses of the Proteins Involved in the Iron-Sulfur Cluster Biosynthesis", Journal of the Crystallographic Society of Japan, vol. 52, 2010 (pp. 174-183), with partial English translation.

Oh-Oka, H., "Iron-Sulfur Centers in Photosystem I.", Low Temperature Science, vol. 67, 2009 (pp. 245-247), with partial English translation.

Farinas, E. et al., "The de novo design of a rubredoxin-like Fe site" Protein Science, vol. 7, 1998 (pp. 1939-1946).

Flexer, V. et al., "Efficient Direct Electron Transfer of PQQ-glucose Dehydrogenase on Carbon Cryogel Electrpdes at Neutral pH", Analytical Chemistry, vol. 83, 2011 (pp. 5721-5727).

Shiota, M. et al., "An Fe—S cluster in the conserved Cys-rich region in the catalytic subunit of FAD-dependent dehydrogenase complexes", Bioelectrochemistry, vol. 112, 2016 (pp. 178-183).

European Patent Office, Supplementary European Search Report, dated Mar. 13, 2019, which was issued in connection with corresponding European patent application No. 16860014.6 (7 pages).

\* cited by examiner

```
MpGDH  359 TNSVFTVNETLAQEQREETEANKTGIWATTPNNLGYPTPEQLFNTTEFYSGKEFADKIRNS 418
MhGDH  356 TDSVFQNETLAQEEQRQTYYNNKTGIWTTTPNNLGYPSPSQLFDGTSFESGKSQAFANRNS 415
MdrGDH 356 TNSVFTNETLAQEEQKDLYYNNKTGIWTTTPNNLGYPSPSQLFTNTTFKSGKFEAAMIRNS 415
MsGDH  358 TDSVFQNETLAEEQRQTYYNNKTGIWTTTPNNLGYPSPSQLFTNTTFRSGKFEAAIRNS 417
MgGDH  354 ASVFLNGTEFYSGKQFAAIRNS 413
CsGDH  358 TNSIFTNDALAAEERQEYDNNKTGIWTTTPNNLGYPTPALENGTEFMDGKAFAAIRNS 417
CrGDH  358 TNSLFTNDALAAEERAEYDNNKTGIWTTTPNNLGYPSPSQLFRGTSFVSGKQFAAIRNS 417
McGDH  360 TNSVFTNETLAQEQVEANKTGIWTTTPNNLGYPTPEQLFNGTIEFYSGKEFAAKIRNS 419

MpGDH  419 TDEWANYYAST-NASNVELLKKQYAIVASRYEENYLSPIEINFTPGYEGISNVDLQNNKY 477
MhGDH  416 TDKYAQYYAST-NATNIELLKKQYAIVASRYEENYLSPIEINFTPGYGGTGDVDLQNNKY 474
MdrGDH 416 TDKYAQYYASTKNATNVELLKKQLAIVASRYEENYLSPIEINFTPGYGGTGMADLQNKKY 474
MsGDH  418 SQEWAQYYASK-NATNIQLLKKQYSIVASRYEENYLSPIEINFTPGYGGTGEVDLQNNKY 477
MgGDH  414 TDEWAERYAAD-NASTVELLKKQYEIVASRYEEDYLSPIEINLTPGYGGTADVDLTNNKY 472
CsGDH  418 TDEWAERYAAD-NATNAELLKKQYAILASRYEEDYLSPIEINLTPGYGGTADVDLTNNKY 476
CrGDH  418 TDEWAERYAAD-NATNADLLKKQYAIVASRYEENYLSPIEINLTPGYGGTGSPDLQNNKY 476
McGDH  420 TDEWANYYAST-AHINSDLIKKQYAIVASRYEENYLSPIEINLTPGYGGTGSPDLQNNKY 478

MpGDH  478 QTVNHVLIAPLSRGYTHINSSDMEDHSMINPQYYSHPMDLDVHIASTKLAREIITASPGL 537
MhGDH  475 QTVNHVLIAPLSRGYTHINSSNIEDPVVINPQYYSHPMDVDVHLASTKLAREILGAEPGL 534
MdrGDH 475 QTVNHVLIAPLSRGYTHINSSDIEDPVVIDPQYYSHPMDVDVHVASTQLARSIILN-APGL 533
MsGDH  478 QTVNHVLVAPLSRGYTHINSSDIEDPVVIDPQYYSHPMDVDVHVASTKLARSILN-AFAL 536
MgGDH  473 QTVNHVLIAPLSRGYTHINSSDIEDPYNINPQYYSHPMDVDVHVASTKLAREIISASPGL 531
CsGDH  477 QTVNHVLIAPLSRGYTHIKSADIEDAVDINPQYYSHPMDVDVHVASTKLAREIISASPGL 536
CrGDH  477 QTVNHVLIAPLSRGYTHIKSADIEDAVDINPQYYSHPMDVDVHVASTKLAREIISASPGL 536
McGDH  479 QTVNHVLIAPLSRGYAHINSDIEPSVINPQYYSHPLDTDVHVASTKLAREIITASPGL 538
```

Fig. 1-4

```
MpGDH  538  GDINSGEIEPGMNITSEDDLRSWLSNVRSDWHPVGTCAMLPKELGGVVSFALMVYGTSN  597
MhGDH  535  ASINSGELQPGSNLTSDEDLKQWLADVRKWLSDNVRSDWHPVGTCAMLPRELGGVVDPNLLVYGTAN  594
MdrGDH 534  ASINSGEVEPGEKVQSDEDVRKWLSDNVRSDWHPVGTCAMLPRKLGGVVDSKLKVYGTAN  593
MsGDH  537  AAINSGEVEPGEKITPQDVRKWLSDNVRSDWHPVGTCAMLPKYLGGVVDSNLKVYGTAN  596
MgGDH  532  GDLNSGEVEPGMDITSDSDVRAWLANNVRSDWHPVGTCAMLPKELGGVVDSLKVYGTAN  591
CsGDH  537  GDINSGETEPGKEITSDSDVRKWLADNVRSDWHPVGTCAMLPKELGGVVDPNLKVYGTSN  596
CrGDH  537  GDINSGEHEPGKELTSDSDVRKWLADNVRSDWHPVGTCAMLPKELDGVVDPNLKVYGTSN  596
McGDH  539  GDLNSGEVEPGMNVTSEDDLRSWLSNVRSDWHPVGTCAMLPQELGGVVSPALMVYGTSN  598

MpGDH  598  LRVVDASIMPLEVSSHLMQPTYGIAEKAADIIKNFYTQHKNQN------  641  (SEQ ID NO: 1)
MhGDH  595  LRVVDASIMPLEISSHLMQPTYGVAEKAADIIKMSRKNNNN-------  635  (SEQ ID NO: 3)
MdrGDH 594  LRVVDASIPLEISSHLMQPTYGVAEKAADIIKISSKK----------  631  (SEQ ID NO: 4)
MsGDH  597  LRVVDASILPLEISSHLMQPTYGVAERAADIIKGSRN----------  633  (SEQ ID NO: 5)
MgGDH  592  LRVVDASVMPLEVSSHLMQPTFGVAEKAADIIKRAEYKK@KAQ-----  633  (SEQ ID NO: 6)
CsGDH  597  LRVVDASIMPLEVSSHLMQPTEGIAEKAADIIKSANKKRSN-------  637  (SEQ ID NO: 7)
CrGDH  597  LRVVDASIMPLEVSSHLMQPTYGIAEKAADIIKSANKKRSN-------  637  (SEQ ID NO: 8)
McGDH  599  LRVVDASIMPLEVSSHLMQPTYGIAEKAADIIKNYYLSQYSGAGKN  644  (SEQ ID NO: 9)
```

GLUCOSE DEHYDROGENASE HAVING MODIFIED ELECTRON TRANSFER PROPERTIES, AND GLUCOSE MEASUREMENT METHOD

CROSS-REFERENCE TO RELATED APPLICATIONS

This application is a 371 of PCT/JP2016/082306, filed Oct. 31, 2016, which claims benefit of Japanese Patent Application No. 2015-214400 filed on Oct. 30, 2015.

TECHNICAL FIELD

The present invention relates to glucose dehydrogenase and a method for measuring glucose. More specifically, the present invention relates to glucose dehydrogenase having modified electron transfer properties and a method for measuring glucose using such glucose dehydrogenase. The present invention also relates to glucose dehydrogenase having modified electron transfer properties that can be advantageously used in a glucose measurement kit as a diagnostic enzyme for diabetes and/or a glucose sensor.

BACKGROUND ART

Glucose measurement is among other things used for monitoring blood glucose of diabetic patients. Quantification of glucose is usually carried out using glucose oxidase (hereinafter, also referred to as GOD) and glucose dehydrogenase (hereinafter, also referred to as GDH). These are used in self-measurement apparatuses for blood glucose (SMBG) that can be used at home, self-contained continuous glucose measurement apparatuses (hereinafter, also referred to as CGM) and apparatuses that can measure blood glucose level immediately upon passing a reading unit over a sensor (hereinafter, also referred to as FGM apparatuses).

Glucose oxidase is an oxidoreductase, which catalyzes the reaction of oxidizing β-D-glucose into D-glucono-1,5-lactone (gluconolactone). Glucose oxidase uses oxygen as an electron acceptor and flavin adenine dinucleotide (FAD) as a cofactor.

Glucose dehydrogenase is classified as an oxidoreductase, uses glucose and an electron acceptor as substrates, and catalyzes a reaction which generates gluconolactone and a reduced-form acceptor. Examples of the glucose dehydrogenase include nicotinamide dinucleotide-dependent GDH, nicotinamide dinucleotide phosphate-dependent GDH, pyrroloquinoline quinone (PQQ)-dependent GDH and FAD-dependent-GDH (flavin bound GDH).

When GOD is used for glucose measurement, a hydrogen peroxide electrode can be used. In this method, a voltage of +0.6 V (vs. Ag/AgCl) to +0.9 V (vs. Ag/AgCl) is applied to the hydrogen peroxide electrode, and the hydrogen peroxide generated when gluconolactone is produced from glucose is measured. At this time, the hydrogen peroxide generated is measured. This method is mainly used in SMBG and CGM. However, this method is problematic in that since a relatively high voltage is applied, measurement is affected with contaminants such as ascorbic acid contained in the measurement solution.

Next, a method using an artificial electron mediator (hereinafter, also referred to simply as a mediator) in place of hydrogen peroxide, was developed. In this method, when glucose is enzymatically converted into gluconolactone, an oxidized-form mediator is converted into a reduced-form mediator. The reduced-form mediator transfers an electron to an electrode and returns to the oxidized-form mediator. An advantage of the method using a mediator is that the applied voltage can be lowered compared to the method using a hydrogen peroxide electrode. Typically, the mediator is a metal complex such as potassium ferricyanide; however, potassium ferricyanide may be deleterious if it enters the human body.

In the cases of GODs and GDHs, the cofactor FAD is frequently buried (resides) deep inside the enzyme molecule. Because of this, when GODs and GDHs are used for glucose measurement, usually the electron cannot be transferred to the electrode if a mediator is not present. However, mediators are costly and difficult to immobilized onto the electrode surface. For example, in glucose measurement of diabetic patients, if the mediator is used without immobilizing the same to an electrode in a self-contained continuous glucose measurement (CGM) apparatus or an FGM apparatus, the mediator present in the measurement solution may flow into the body. However, since most mediators are not biologically compatible or are toxic, it is undesirable for the mediator to flow into the body. Because of this, glucose measurement methods using mediators are not suitable for CGM and FGM apparatuses. Furthermore, when comparing GOD to GDH, there is the possibility that GOD can be influenced by dissolved oxygen present in the system and, therefore, GDH is needed more than GOD. As such, a GDH, which can be used for a compound that can be measured even when a low-voltage is applied, is desired. Moreover, a GDH capable of transferring an electron directly to an electrode in the absence of a mediator, is desired.

Non Patent Literature 1 reports, apart from an approach to immobilizing the mediator to an electrode, a method for modifying GOD with a mediator. However, for reasons of decrease in enzyme activity due to chemical modification and the possibility that the mediator may flow into the body cannot be denied, practical use of this method has not yet been implemented.

On the other hand, iron sulfur clusters are known as substances involved in redox reactions. An iron sulfur cluster (also referred to as an FeS cluster) is composed of iron atom(s) and sulfur atom(s). Various types of proteins comprising an iron sulfur cluster are known and, primarily, a cysteine residue of the polypeptide forms a coordinate bond with an iron atom of the iron sulfur cluster. Typical iron sulfur clusters contained in proteins include [2Fe-2S] type, [3Fe-4S] type and [4Fe-4S] type. With regard to the amino acid sequence, motifs characteristic to an iron sulfur cluster coordination are known. For example, Non Patent Literature 2 describes a motif represented by $C-X_{2-5}-C-XX-C$ (X represents an amino acid). Non Patent Literature 3 describes an iron sulfur cluster present in the reaction center of photochemical system I, and describes that the amino acid sequence, which coordinates to the cluster, is C-XX-C-XX-C-XXX-CP, a motif characteristic to cluster coordination.

Patent Literature 1 describes a GDH from *Burkholderia cepacia*. The GDH described is a complex protein consisting of an α subunit and a β subunit. In the α subunit, FAD and FeS cluster are contained. The β subunit is cytochrome c and plays a role in electron transfer of the electron from FAD to the electrode. Patent Literature 2 describes glucose measurement and a glucose sensor using the GDH from *Burkholderia cepacia*. Patent Literature 2 also describes that if the β subunit responsible for electron transfer is not present, the activity to directly transfer the electron from the GDH to the electrode is markedly decreased.

The direct electron transfer type-GDH known in the art has the possibility of acting not only on glucose but also on other sugars. Because of this, the substrate specificity thereof is not necessarily sufficient for use in glucose sensors. Further, the direct electron transfer type-GDH known in the art requires an electron transfer domain, which plays a role analogous to a mediator and, therefore, is accompanied with problems such as large molecular weight of the enzyme, stability of the enzyme and productivity. Furthermore, since this enzyme is a membrane bound enzyme from *Burkholderia cepacia*, a complicated treatment such as solubilization is required in order to obtain a subunit of the enzyme or the enzyme itself. In addition, the enzyme subjected to solubilization treatment is unstable. If treatment such as drying is applied, it is difficult to maintain the structure of the enzyme or a subunit thereof.

As an example where an iron sulfur cluster is introduced into a protein, Non Patent Literature 4 can be mentioned. Non Patent Literature 4 describes that an iron sulfur cluster was introduced by substituting each of four amino acid residues in immunoglobulin-bound B1 domain of *Streptococcus*-derived protein G, with a cysteine residue. According to Non Patent Literature 4, the designed iron sulfur cluster-containing protein is unstable.

CITATION LIST

Patent Literatures

Patent Literature 1: JP Patent No. 4107386 (WO 2002/036779)
Patent Literature 2: JP Patent No. 4359595 (WO 2005/023111)

Non Patent Literatures

Non Patent Literature 1: The Journal of Physical Chemistry, 91 (6), 1285-9, 1987
Non Patent Literature 2: Journal of the Crystallographic Society of Japan, 52, 174-183, 2010
Non Patent Literature 3: Low Temperature Science, 67, 245-247, 2009
Non Patent Literature 4: Protein Science, 7, 1939-1946, 1998

SUMMARY OF INVENTION

Technical Problem

An object of the present invention is to provide a glucose dehydrogenase having modified electron transfer properties which can overcome the problem(s) mentioned above.

Solution to Problem

As a result of conducting intensive studies in order to solve the problems above, the present inventors conceived of the idea of introducing amino acid substitutions into the glucose dehydrogenase, instead of immobilizing the mediator to the electrode surface. Upon carrying out amino acid substitution to a glucose dehydrogenase having no cytochrome domain, surprisingly, a glucose dehydrogenase having modified electron transfer properties was obtained and the present invention was made.

The present invention encompasses the following embodiments.

[1] A glucose dehydrogenase mutant having at least one amino acid substitution, capable of transferring an electron from the enzyme directly to an electrode and having no cytochrome domain, or a glucose dehydrogenase mutant having at least one amino acid substitution in a region consisting of the 457th position to 477th position or the 461st to 477th position of SEQ ID NO: 1 or a region corresponding thereto; having modified electron transfer properties; and having no cytochrome domain.

[2] The mutant according to 1, wherein the glucose dehydrogenase mutant capable of transferring an electron from the enzyme directly to an electrode comprises at least one amino acid substitution in the region consisting of the 457th position to 477th position or the 461st to 477th position of SEQ ID NO: 1.

[3] The glucose dehydrogenase mutant according to 1 or 2, comprising an amino acid substitution at one or more of the positions corresponding to the 464th position, 470th position and 472nd position of the amino acid sequence of SEQ ID NO: 1.

[4] The glucose dehydrogenase mutant according to any one of 1 to 3, wherein, in said glucose dehydrogenase, the full length amino acid sequence of said glucose dehydrogenase has an amino acid sequence identity of 70% or more with the amino acid sequence of SEQ ID NO: 1; and the amino acid sequence in the homologous region consisting of the amino acid sequences of 32 to 34th position, 58 to 62nd position, 106 to 109th position, 111 to 116th position, 119 to 126th position, 132 to 134th position, 136 to 144th position, 150 to 153rd position, 167 to 171st position, 222 to 225th position, 253 to 262nd position, 277 to 281st position, 301 to 303rd position, 305 to 312nd position, 314 to 319th position, 324 to 326th position, 332 to 337th position, 339 to 346th position, 388 to 390th position, 415 to 417th position, 454 to 456th position, 486 to 491st position, 508 to 511st position, 564 to 567th position, 570 to 574th position, 584 to 586th position, 592 to 594th position, 597 to 599th position, 601 to 604th position, 607 to 609th position, 611 to 617th position, and 625 to 630th position of SEQ ID NO: 1 and the amino acid sequence in the homologous region of the corresponding positions of said glucose dehydrogenase have an amino acid sequence identity of 90% or more; and said glucose dehydrogenase has glucose dehydrogenase activity capable of transferring an electron from the enzyme directly to an electrode.

[5] The glucose dehydrogenase mutant according to 3 or 4, wherein
the amino acid at the position corresponding to the 464th position of the amino acid sequence of SEQ ID NO: 1 is substituted with a polar amino acid or alanine,
the amino acid at the position corresponding to the 470th position of the amino acid sequence of SEQ ID NO: 1 is substituted with a polar amino acid or alanine, and/or
the amino acid at the position corresponding to the 472nd position of the amino acid sequence of SEQ ID NO: 1 is substituted with a polar amino acid or alanine.

[6] The glucose dehydrogenase mutant according to any one of 3 to 5, wherein,
the amino acid at the position corresponding to the 464th position of the amino acid sequence of SEQ ID NO: 1 is substituted with an amino acid selected from the group consisting of cysteine, aspartic acid, histidine, serine, alanine and threonine,
the amino acid at the position corresponding to the 470th position of the amino acid sequence of SEQ ID NO: 1 is substituted with an amino acid selected from the group consisting of cysteine, aspartic acid, histidine, serine, alanine, threonine and arginine, and/or
the amino acid at the position corresponding to the 472nd position of the amino acid sequence of SEQ ID NO: 1 is substituted with an amino acid selected from the group consisting of cysteine, aspartic acid, histidine and serine.

[7] The glucose dehydrogenase mutant according to 5 or 6, wherein 2 or 3 amino acids at the positions corresponding to the 464th position, 470th position or 472nd position of the amino acid sequence of SEQ ID NO: 1 are substituted with cysteine;

2 or 3 amino acids at the positions corresponding to the 464th position, 470th position or 472nd position of the amino acid sequence of SEQ ID NO: 1 are substituted with aspartic acid, or 2 or 3 amino acids at the positions corresponding to the 464th position, 470th position or 472nd position of the amino acid sequence of SEQ ID NO: 1 are substituted with histidine.

[8] The glucose dehydrogenase according to any one of 1 to 4, wherein, (i) when the amino acid sequence of glucose dehydrogenase is aligned with the amino acid sequence of SEQ ID NO: 1, the glucose dehydrogenase comprises at least 1, 2 or 3 substitutions with a polar amino acid or alanine or a substitution with an amino acid selected from the group consisting of cysteine, aspartic acid, histidine, serine, alanine, threonine and arginine, in the region consisting of the 457th position to 477th position or the 461st to 477th position of SEQ ID NO: 1 or in the region corresponding thereto, or a motif sequence consisting of Cys-Xaa-Xaa-Xaa-Xaa-Xaa-Cys-Xaa-Cys in the region from the 461st to 476th position of SEQ ID NO: 1 or in the region corresponding thereto; or a substitution with a polar amino acid or alanine, or a substitution of an amino acid selected from the group consisting of cysteine, aspartic acid, histidine, serine, alanine, threonine and arginine at at least 1, 2 or 3 positions corresponding to the 464th position, 470th position and 472nd position of the amino acid sequence of SEQ ID NO: 1; and comprises glucose dehydrogenase activity capable of transferring an electron from the enzyme directly to an electrode, (ii) with regard to the glucose dehydrogenase of said (i), the glucose dehydrogenase has an amino acid sequence comprising a substitution, deletion or addition of one or several amino acids at a position other than the position(s) having the above amino acid substitution introduced thereto, and comprises glucose dehydrogenase activity capable of transferring an electron from the enzyme directly to an electrode, (iii) with regard to the glucose dehydrogenase of said (i), the full length amino acid sequence of said glucose dehydrogenase has an amino acid sequence identity of 70% or more with the amino acid sequence of SEQ ID NO: 1;

the amino acid sequence in the homologous region consisting of the amino acid sequences at the 32 to 34th position, 58 to 62nd position, 106 to 109th position, 111 to 116th position, 119 to 126th position, 132 to 134th position, 136 to 144th position, 150 to 153rd position, 167 to 171st position, 222 to 225th position, 253 to 262nd position, 277 to 281st position, 301 to 303rd position, 305 to 312nd position, 314 to 319th position, 324 to 326th position, 332 to 337th position, 339 to 346th position, 388 to 390th position, 415 to 417th position, 454 to 456th position, 486 to 491st position, 508 to 511st position, 564 to 567th position, 570 to 574th position, 584 to 586th position, 592 to 594th position, 597 to 599th position, 601 to 604th position, 607 to 609th position, 611 to 617th position, and 625 to 630th position of SEQ ID NO: 1 and the amino acid sequence in the homologous region of the corresponding positions of the glucose dehydrogenase have an amino acid sequence identity of 90% or more; and has glucose dehydrogenase activity capable of transferring an electron from the enzyme directly to an electrode, (iv) the amino acid residues at the positions corresponding to the positions of the 464th position, 470th position and 472nd position of the amino acid sequence of SEQ ID NO: 1 are cysteine, (v) the amino acid residues at the positions corresponding to the positions of the 464th position, 470th position and 472nd position of the amino acid sequence of SEQ ID NO: 1 are aspartic acid, or (vi) the amino acid residues at the positions corresponding to the positions of the 464th position, 470th position and 472nd position of the amino acid sequence of SEQ ID NO: 1 are histidine.

[9] The glucose dehydrogenase according to any one of 1 to 8, wherein, the glucose dehydrogenase is from the genus *Mucor*, the genus *Absidia*, the genus *Actinomucor*, the genus *Circinella*, *Mucor prainii*, *Mucor circinelloides*, *Mucor hiemalis*, *Mucor subtilissimus*, *Mucor guilliermondii*, *Mucor javanicus*, *Mucor dimorphosporus*, *Absidia cylindrospora*, *Absidia hyalospora*, *Actinomucor elegans*, *Circinella simplex*, *Circinella* sp., *Circinella angarensis*, *Circinella chinensis*, *Circinella lacrymispora*, *Circinella minor*, *Circinella mucoroides*, *Circinella rigida*, *Circinella umbellata* or *Circinella muscae*.

[10] The glucose dehydrogenase according to any one of 1 to 9, capable of transferring an electron from the enzyme directly to an electrode.

[11] The glucose dehydrogenase according to any one of 1 to 10, having the following characteristics:

action: exhibits glucose dehydrogenase activity and is capable of directly transferring an electron from the enzyme directly to an electrode in the absence of a mediator, molecular weight: the molecular weight estimated based on the primary sequence of the polypeptide chain portion of the protein is about 70 kDa or the molecular weight thereof measured by SDS-polyacrylamide electrophoresis is about 80 kDa, substrate specificity: the reactivity to maltose and D-xylose is low compared to the reactivity to D-glucose, cofactor characteristics: is a flavin bound type and comprises at least one amino acid substitution within the molecule.

[12] A gene encoding a glucose dehydrogenase having modified electron transfer properties said gene consisting of (a) DNA encoding the glucose dehydrogenase according any one of 1 to 11, (b) DNA encoding the amino acid sequence of SEQ ID NO: 12, (c) DNA comprising a nucleotide sequence of SEQ ID NO: 13, or (d) DNA comprising a nucleotide sequence having a sequence identity of 65% or more with the nucleotide sequence of SEQ ID NO: 13 and encoding a protein having a glucose dehydrogenase activity capable of transferring an electron directly to an electrode in the absence of a mediator.

[13] A vector comprising the gene according to 12.

[14] A host cell comprising the vector according to 13.

[15] A method for producing a glucose dehydrogenase comprising the following steps:

culturing the host cell according to 14, expressing the glucose dehydrogenase gene contained in the host cell, and recovering glucose dehydrogenase from the culture.

[16] A method for measuring glucose using the glucose dehydrogenase of any one of 1 to 11.

[17] A glucose measuring kit comprising the glucose dehydrogenase of any one of 1 to 11.

[18] A glucose sensor comprising the glucose dehydrogenase of any one of 1 to 11.

The present specification incorporates and contains the contents disclosed in JP Patent Application No. 2015-214400, which is a priority document of the present application.

Advantageous Effects of Invention

One effect of the present invention is that glucose can be measured in the presence of a mediator reduced in concentration or in the absence of a mediator. Mediators can be toxic to diabetic patients; however, the glucose dehydrogenase of the present invention can be used in a self-contained system implanted in the body for continuous glucose measurement since a mediator is not required in glucose measurement. Further, the glucose measurement method according to the present invention can be performed at a low cost since expensive mediator molecules are not required or the amount thereof can be reduced. In addition, a wide variety of electron acceptors (compounds) can be employed with the glucose dehydrogenase according to the present invention compared to conventional glucose dehydrogenases and the present invention provides more alternatives. Furthermore, compared to glucose oxidase, the glucose dehydrogenase according to the present invention is not influenced by dissolved oxygen and, therefore, capable of more accurate glucose measurement.

BRIEF DESCRIPTION OF DRAWINGS

FIG. 1-1 shows a multiple alignment of GDHs derived from various species. MpGDH represents a GDH from *Mucor prainii* (SEQ ID NO: 1); MhGDH represents a GDH from *Mucor hiemalis* (SEQ ID NO: 3), MrdGDH represents a GDH from *Mucor* RD056860 (SEQ ID NO: 4), MsGDH represents a GDH from *Mucor subtilissimus* (SEQ ID NO: 5), MgGDH represents a GDH from *Mucor guilliermondii* (SEQ ID NO: 6), CsGDH represents a GDH from *Circinella simplex* (SEQ ID NO: 7), CrGDH represents a GDH from *Circinella* genus (SEQ ID NO: 8) and McGDH represents a GDH from *Mucor circinelloides* (SEQ ID NO: 9).

FIG. 1-2 shows the multiple alignment continued from FIG. 1-1.

FIG. 1-3 shows the multiple alignment continued from FIG. 1-1.

FIG. 1-4 shows the multiple alignment continued from FIG. 1-1.

FIG. 2 shows the measurement results of MpGDH-M1 by chronoamperometry.

FIG. 3 shows the measurement results of a triple mutant of MpGDH-M 1/Y464C/V470C/L472C by chronoamperometry.

Figure 2:
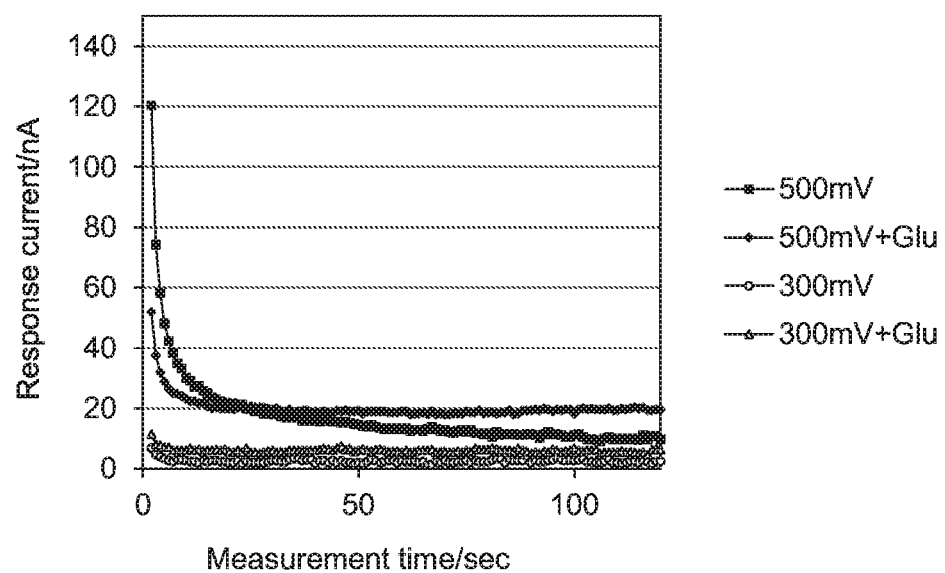

DESCRIPTION OF EMBODIMENTS (Glucose Dehydrogenase According to the Present Invention)

In the first embodiment, the present invention provides a glucose dehydrogenase mutant. In one embodiment, the present invention provides a glucose dehydrogenase having amino acid substitution and having modified electron transfer properties. In one embodiment, the amino acid substitution can be a substitution in the region of from 457th to 477th position or from 461 to 477th position of SEQ ID NO: 1, or the region corresponding thereto. In the present specification, "modified electron transfer property (properties)" means that electron transfer from the (modified) enzyme to an electrode is enhanced compared to an unmodified enzyme. The degree of enhancement of the electron transfer can be evaluated based on the ratio of response current (nA) of a modified enzyme to an unmodified enzyme when a voltage (for example, +300 mV (vs. Ag/AgCl) or +500 mV (vs. Ag/AgCl)) is applied. Accordingly, having "modified electron transfer properties" for a GDH mutant means that when a voltage is applied the response current increases by, for example, 20%, 30%, 40%, 50%, 60%, 70%, 80%, 90%, 100%, 200%, 300%, 400%, 500%, 1000%, or 1500% or more, compared to that of an unmodified enzyme. The phrase "modified electron transfer properties" for a GDH mutant means that when a voltage is applied the response current increases by, for example, 1.2 times, 1.5 times, 2 times, 3 times, 4 times, 5 times, 10 times, 15 times, 20 times, 25 times, or 30 times or more, compared to that of an unmodified enzyme.

In another embodiment, the present invention provides a glucose dehydrogenase having amino acid substitution and capable of directly transferring an electron from the enzyme to an electrode. Such a glucose dehydrogenase may also be referred to as a direct electron transferring glucose dehydrogenase in the present specification. In one embodiment, the amino acid substitution can be a substitution in the region from the 457th to 477th position of SEQ ID NO: 1 or in the region corresponding thereto.

A direct electron transferring glucose dehydrogenase does not require a mediator such as potassium ferricyanide and can transfer an electron from the enzyme directly to a solid phase electrode. That is the phrase "can directly transfer an electron" means that when a voltage is applied an electron can be transferred from the enzyme to an electrode in the absence of a mediator, and a response current can be observed. Without wishing to be bound to any particular theory, it is believed that in the situation above, the electron is transferred from a cofactor such as FAD contained in the enzyme or from a substituted amino acid contained in the enzyme to the solid phase electrode. Such electron transfer between a chemical species and solid phase electrode is referred to as heterogeneous electron transfer. Electron transfer is a type of elementary reaction involving electron transfer, and inner-sphere, outer-sphere and heterogeneous electron transfer are known. The direct electron transfer of the present invention is not particularly limited as long as the electron is transferred from the enzyme to the solid phase electrode. Incidentally, if the GDH and another protein forms a fusion by an artificial genetic engineering or if the GDH manipulated by genetic engineering forms a complex with a metal (ion) or a small molecule compound, then the term enzyme used here refers to the entire fusion or complex. In one embodiment, the glucose dehydrogenase of the present invention is a flavin bound GDH (flavin binding GDH).

In one embodiment, the glucose dehydrogenase of the present invention is a mutant of a glucose dehydrogenase, which is prepared based on glucose dehydrogenase derived from the genus *Mucor* and having the amino acid sequence of SEQ ID NO: 1, SEQ ID NO: 10 or SEQ ID NO: 12. Examples of such mutant include a glucose dehydrogenase having an amino acid sequence, which has a high sequence identity with SEQ ID NO: 1 (for example, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, for example 99% or more); and a glucose dehydrogenase having an amino acid sequence, which has a modification or mutation, or deletion, substitution, addition and/or insertion of one to several amino acids in the amino acid sequence of SEQ ID NO: 1.

Glucose dehydrogenases are found throughout nature and can be obtained by searching for enzymes from microorganisms, animals and plants. In microorganisms, glucose dehydrogenase can be obtained from, e.g., filamentous fungi, yeast or bacteria. The glucose dehydrogenase of the present invention may be prepared based on a GDH from, for example, a microorganism classified in the subphylum *Mucor*, the class *Mucor*, the order *Mucor* or the family *Mucor*, for example, species such as the genus *Mucor*, the genus *Absidia*, the genus *Actinomucor* or the genus *Circinella*.

Examples of the microorganism belonging to the genus *Mucor* include *Mucor prainii, Mucor circinelloides, Mucor hiemalis, Mucor subtilissimus, Mucor guilliermondii, Mucor javanicus* and *Mucor dimorphosporus*. Examples of the microorganism belonging to the genus *Absidia* include *Absidia cylindrospora* and *Absidia hyalospora*. Examples of the microorganism belonging to the genus *Actinomucor* include *Actinomucor elegans*. Examples of the microorganism belonging to the genus *Circinella* include *Circinella simplex, Circinella sp., Circinella angarensis, Circinella chinensis, Circinella lacrymispora, Circinella minor, Circinella mucoroides, Circinella rigida, Circinella umbellata* and *Circinella muscae*.

The GDH from which the GDH mutant of the present invention derived is a GDH having no cytochrome domain in nature. Accordingly, a GDH having a cytochrome domain in nature is excluded from (the GDH of) the present invention. The GDH of the present invention is a water soluble type and membrane-bound GDHs are excluded.

(Region to Introduce Amino Acid Substitution)

The glucose dehydrogenase mutant of the present invention can be obtained by introducing amino acid substitution(s) into a particular region of a glucose dehydrogenase. In one embodiment, the particular region is the region from the 457th to 477th position, 461 to 476th position or 461 to 477th position of SEQ ID NO: 1 or the region corresponding thereto.

In one embodiment, with regard to the amino acid sequence of a particular region of the glucose dehydrogenase, at least 1, 2 or 3 amino acid residues can be substituted with a polar amino acid or alanine, for example, cysteine, aspartic acid, histidine, serine, threonine or alanine. In one embodiment, the glucose dehydrogenase mutant of the present invention may have at least 1, 2 or 3 amino acid substitutions, for example, an amino acid substitution with cysteine, serine, alanine, aspartic acid, threonine, arginine or histidine, in the region from the 457th to 477th position or the 461st to 477th position of the amino acid sequence of SEQ ID NO: 1 or the region corresponding thereto. In another embodiment, the glucose dehydrogenase mutant of the present invention has a motif sequence consisting of Cys-Xaa-Xaa-Xaa-Xaa-Xaa-Cys-Xaa-Cys (SEQ ID NO: 14, where Xaa represents any other amino acid residue) in the region from the 461st to 476th position of the amino acid sequence of SEQ ID NO: 1, or amino acids at the positions corresponding to the 464th position, 470th position and 472nd position of the amino acid sequence of SEQ ID NO: 1 are all cysteine, all aspartic acid or all histidine.

The glucose dehydrogenase mutant of the present invention may have amino acid substitution(s) in the particular region(s) mentioned above in the amino acid sequence of SEQ ID NO: 1. The glucose dehydrogenase mutant of the present invention may further have a deletion, insertion, addition and/or substitution of one or several (for example, 1 to 15, 1 to 10, 1 to 5, for example 1 to 3) amino acids at positions other than the position(s) having the amino acid substitutions mentioned above. The present invention further includes a GDH, which may have an amino acid substitution mutation for improving properties such as substrate specificity and thermal stability apart from the amino acid substitution in the particular region(s) mentioned above; and has an amino acid sequence identity of 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, for example 99% or more, with the amino acid sequence of SEQ ID NO: 1, from which the amino acids other than amino acids substituted above are excluded; has glucose dehydrogenase activity and modified electron transfer properties. Said GDH having modified electron transfer properties include direct electron transferring (type) GDH.

In one embodiment, the GDH of the present invention having modified electron transfer properties comprises the amino acid sequence of SEQ ID NO: 1 or an amino acid sequence having a sequence identity of, for example, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, for example 99% or more, with said amino acid sequence of SEQ ID NO: 1; or has an amino acid sequence having a deletion, substitution or addition of one or several amino acids in said amino acid sequence; has glucose dehydrogenase activity, and has at least 1, 2 or 3 amino acid substitutions in the region of the 457th to 477th position or the 461st to 477th position of the amino acid sequence of SEQ ID NO: 1 or the region corresponding thereto, for example, a substitution with a polar amino acid or alanine or amino acid substitution with cysteine, serine, alanine, aspartic acid, threonine or histidine, or has a motif sequence consisting of Cys-Xaa-Xaa-Xaa-Xaa-Xaa-Cys-Xaa-Cys in the region from the 461st to 476th position of the amino acid sequence of SEQ ID NO:1 or the region corresponding thereto; or has cysteine, aspartic acid or histidine residue(s)

in the positions corresponding to the 464th position, 470th position and 472nd position of the amino acid sequence of SEQ ID NO: 1.

(Corresponding Region)

The region corresponding to the region from the 461st to 477th position of the amino acid sequence of SEQ ID NO: 1 refers to the region of the amino acid sequence of a GDH derived from another species and corresponding to the region from the 461st to 477th position of the amino acid sequence of SEQ ID NO: 1 when the amino acid sequence of the GDH is aligned with the amino acid sequence of SEQ ID NO: 1. The region corresponding to the region from the 457th to 477th position of the amino acid sequence of SEQ ID NO: 1 refers to the region of the amino acid sequence of a GDH derived from another species and corresponding to the region from the 457th to 477th position of the amino acid sequence of SEQ ID NO: 1, when the amino acid sequence of the GDH is aligned with the amino acid sequence of SEQ ID NO: 1.

Methods for specifying the "corresponding region" include the following. For example, first, amino acid sequences are compared using a known algorithm such as the Lipman-Pearson method and multiple alignment is carried out to provide maximum identity for conserved amino acid residues present in the amino acid sequences of the individual GDHs. By aligning amino acid sequences of GDHs in this manner, it is possible to determine the positions of homologous amino acid residues in individual GDH sequences regardless of insertions and deletions in the amino acid sequences. Next, and optionally, a known secondary structure predicting algorithm can be used to predict secondary structures such as α-helices, β sheets and coils.

For example, by applying a secondary structure predicting algorithm to the amino acid sequence of SEQ ID NO: 1 or the amino acid sequence of an appropriate GDH, the secondary structure thereof can be predicted. Examples of the secondary structure prediction tools include Jpred 3 (Cole C et al., The Jpred 3 secondary structure prediction server. Nucleic Acids Res. 2008, W197-201) and Jpred4 (Drozdetskiy A et al., (2015) JPred4: a protein secondary structure prediction server, Nucleic Acids Res., doi: 10. 1093/nar/gkv332) in which JNet algorithm is implemented. If the secondary structure of MpGDH (SEQ ID NO: 1) is predicted with Jpred 3, it is predicted that the regions from the 456th to 460th position and from the 477th to 483rd position of the amino acid sequence of SEQ ID NO: 1 have a β strand structure (Satake, et al., J. Biosci. Bioeng., (2015), Vol. 120, Issue 5, November 2015, 498-503); however, it is not predicted that the region from the 461st to 476th position has a β strand structure or an α helix structure. Similarly, Jpred 4 does not predicted that the region from the 461st to 477th position of SEQ ID NO: 1 has a β strand structure or an α helix structure. Where predictions made by Jpred 3 and Jpred 4 differ, the prediction by Jpred 4 should prevail.

Examples of the region corresponding to the region from the 461st to the 477th position of the amino acid sequence of SEQ ID NO: 1 include, but are not limited to,
the region from the 458th to 474th position of the amino acid sequence of SEQ ID NO 3:
the region from the 458th to 474th position of the amino acid sequence of SEQ ID NO: 4
the region from the 461st to 477th position of the amino acid sequence of SEQ ID NO: 5,
the region from the 456th to 472nd position of the amino acid sequence of SEQ ID NO: 6,
the region from the 460th to 476th position of the amino acid sequence of SEQ ID NO: 7,
the region from the 460th to 476th position of the amino acid sequence of SEQ ID NO:8, and
the region from the 462nd to 478th position of the amino acid sequence of SEQ ID NO:9. With respect to other GDHs, if alignment is performed for example in accordance with the description of Satake, et al., (J. Biosci. Bioeng., (2015), Vol. 120, Issue 5, November 2015, 498-503), the region corresponding to the region from the 461st to 477th position of the amino acid sequence of SEQ ID NO: 1 can be identified.

It is believed that corresponding regions occupy the same or analogous region in the three dimensional structures and it is rationally presumed to form an analogous region in a target GDH.

Examples of the region corresponding to the region from 457th to 477th position of the amino acid sequence of SEQ ID NO: 1 include, but are not limited to, the region from the 454th to 474th position of the amino acid sequence of SEQ ID NO: 3, the region from the 454th to 474th position of the amino acid sequence of SEQ ID NO: 4, the region from the 457th to 477th position of the amino acid sequence of SEQ ID NO: 5, the region from the 452nd to 472nd position of the amino acid sequence of SEQ ID NO: 6, the region from the 456th to 476th position of the amino acid sequence of SEQ ID NO: 7, the region from the 456th to 476th position of the amino acid sequence of SEQ ID NO: 8, and the region from the 458th to 478th position of the amino acid sequence of SEQ ID NO: 9. With respect to other GDHs, if alignment is performed for example in accordance with the description of Satake, et al., (J. Biosci. Bioeng., (2015), Vol. 120, Issue 5, November 2015, 498-503), the region corresponding to the region from the 461st to 477th position or the 457th to 477th position of the amino acid sequence of SEQ ID NO: 1 can be identified.

FIG. 1 shows amino acid sequences of GDHs derived from various known species. The top row shows the amino acid sequence of SEQ ID NO: 1. This is aligned with GDHs derived from various species based on a known algorithm. The region corresponding to 457th to 477th position or the 461st to 477th position of the GDH from the genus *Mucor* having the amino acid sequence of SEQ ID NO: 1 and positions corresponding to the 464th position, 470th position and 472nd position thereof can be specified.

In one embodiment, GDH of the present invention having modified electron transfer properties has at least three cysteine residues in the region corresponding to the 461st to 476th position, 461st to 477th position or the 457th to 477th position of the amino acid sequence of SEQ ID NO: 1. Herein, the region corresponding to the 461st to 476th position of the amino acid sequence of SEQ ID NO: 1 may have a motif sequence consisting of Cys-Xaa-Xaa-Xaa-Xaa-Xaa-Cys-Xaa-Cys (SEQ ID NO: 14), where Xaa may represent any amino acid.

(Corresponding Position)

In one embodiment, GDH of the present invention having modified electron transfer properties has 1, 2, or 3 amino acid substitutions at the positions corresponding to the 464th position, 470th position and 472nd position of the amino acid sequence of SEQ ID NO: 1, for example, substitutions with amino acids such as cysteine, serine, alanine, aspartic acid, threonine or histidine. The positions corresponding to these positions of the amino acid sequence of SEQ ID NO: 1, can be specified by the same manner as in the method above for specifying the corresponding region.

The positions corresponding to the 464th position, 470th position and 472nd position of the amino acid sequence of SEQ ID NO: 1, when the amino acid sequence of a target GDH is compared to the amino acid sequence of the GDH of SEQ ID NO: 1, refer to the positions corresponding to the 464th position, 470th position, and 472nd position of SEQ ID NO: 1, respectively. If the GDH is a particular GDH from the genus *Mucor* or *Circinella*, then these corresponding positions can be identified e.g., from FIG. 1. In the case of a GDH having homology with the GDH of SEQ ID NO: 1, the individual corresponding positions can be identified in the same manner.

(a) The position corresponding to the 464th position of the amino acid sequence of SEQ ID NO: 1 is
the 461st position in the GDH from *Mucor hiemalis* (MhGDH, SEQ ID NO: 3),
the 461st position in the GDH from *Mucor* RD056860 (MrdGDH, SEQ ID NO: 4),
the 464th position in the GDH from *Mucor subtilissimus* (MsGDH, SEQ ID NO: 5),
the 459th position in the GDH from *Mucor guilliermondii* (MgGDH, SEQ ID NO: 6),
the 463rd position in the GDH from *Circinella simplex* (CsGDH, SEQ ID NO: 7),
the 463rd position in the GDH from *Circinella* (CrGDH, SEQ ID NO: 8), and
the 465th position in the GDH from *Mucor circinelloides* (McGDH, SEQ ID NO: 9).

(b) The position corresponding to the 470th position of the amino acid sequence of SEQ ID NO: 1 is
the 467th position in the GDH from *Mucor hiemalis* (MhGDH, SEQ ID NO: 3),
the 467th position in the GDH from *Mucor* RD056860 (MrdGDH, SEQ ID NO: 4),
the 470th position in the GDH from *Mucor subtilissimus* (MsGDH, SEQ ID NO: 5),
the 465th position the GDH from *Mucor guilllermondii* (MgGDH, SEQ ID NO: 6),
the 469th position in the GDH from *Circinella simplex* (CsGDH, SEQ ID NO: 7)
the 469th position in the GDH from genus *Circinella* (CrGDH, SEQ ID NO: 8), and
the 471st position in the GDH from *Mucor circinelloides* (McGDH, SEQ ID NO: 9).

(c) The position corresponding to the 472nd position of the amino acid sequence of SEQ ID NO: 1 is
the 469th position of the GDH from *Mucor hiemalis* (MhGDH, SEQ ID NO: 3),
the 469th position of the GDH from *Mucor* RD056860 (MrdGDH, SEQ ID NO: 4),
the 472nd position of the GDH from *Mucor subtilissimus* (MsGDH, SEQ ID NO: 5),
the 467th position of the GDH from *Mucor guilllermondii* (MgGDH, SEQ ID NO: 6),
the 471st position of the GDH from *Circinella simplex* (CsGDH, SEQ ID NO: 7)
the 471st position of the GDH from genus *Circinella* (CrGDH, SEQ ID NO: 8), and
the 473rd position of the GDH from *Mucor circinelloides* (McGDH, SEQ ID NO: 9).

(a) Optionally, the amino acid at the position corresponding to the 464th position of the amino acid sequence of SEQ ID NO: 1 may be substituted with a polar amino acid or alanine. In the present specification, the polar amino acid refers to cysteine, serine, threonine, asparagine, glutamine, aspartic acid, glutamic acid, histidine, arginine, lysine, glycine and tyrosine.

(b) Optionally, the amino acid at the position corresponding to the 470th position of the amino acid sequence of SEQ ID NO: 1 may be substituted with a polar amino acid or alanine.

(c) Optionally, the amino acid at the position corresponding to the 472nd position of the amino acid sequence of SEQ ID NO: 1 may be substituted with a polar amino acid or alanine.

(a-1) Optionally, the amino acid at the position corresponding to the 464th position of the amino acid sequence of SEQ ID NO: 1 may be substituted with cysteine, serine, alanine, aspartic acid, threonine or histidine.

(b-1) Optionally, the amino acid at the position corresponding to the 470th position of the amino acid sequence of SEQ ID NO: 1 may be substituted with cysteine, alanine, serine, threonine, aspartic acid, arginine or histidine.

(c-1) Optionally, the amino acid at the position corresponding to the 472nd position of the amino acid sequence of SEQ ID NO: 1 may be substituted with cysteine, serine, aspartic acid or histidine.

The above (a), (b), (c), (a-1), (b-1) and (c-1) may be present in any combination. For example, a mutant may have substitutions (a) and (b), substitutions (b) and (c), substitutions (c) and (a) and may have substitutions (a), (b) and (c). For convenience, a mutation substituting amino acid $A_1$ at position xxx with amino acid $A_2$ is expressed as $A_1$xxx$A_2$. For example, the mutation substituting tyrosine at the 464th position with cysteine is expressed as Y464C. Further, in double mutants, mutations are expressed as the first mutation/second mutation. For example, the GDH of the present invention may have mutations Y464C/V470C, Y464C/L472C, or V470C/L472C in the amino acid sequence of SEQ ID NO: 1. Similarly, the present invention provides the following mutants although the mutants are not limited thereto:
Y464C/V470C, Y464C/L472C, V470C/L472C, Y464S/V470S, Y464S/L472S, V470S/L472S, Y464H/V470H, Y464H/L472H, V470H/L472H, Y464A/V470A, Y464A/L472A, V470A/L472A, Y464T/V470T, Y464T/L472T, V470T/L472T, Y464R/V470R, Y464R/L472R, V470R/L472R, Y464D/V470D, Y464D/L472D, V470D/L472D, Y464C/V470C/L472C, Y464C/V470C/L472S, Y464C/V470S/L472C, Y464S/V470C/L472C, Y464C/V470S/L472S, Y464S/V470C/L472S, Y464S/V470S/L472C, Y464S/V470S/L472S, Y464C/V470C/L472D, Y464C/V470D/L472C, Y464D/V470C/L472C, Y464C/V470D/L472D, Y464D/V470C/L472D, Y464D/V470D/L472C, Y464D/V470D/L472D, Y464D/V470D/L472S, Y464D/V470S/L472D, Y464S/V470D/L472D, Y464D/V470S/L472S, Y464S/V470D/L472S, Y464S/V470S/L472D, Y464C/V470C/L472H, Y464C/V470H/L472C, Y464H/V470C/L472C, Y464C/V470H/L472H, Y464H/V470C/L472H, Y464H/V470H/L472C, Y464S/V470S/L472H, Y464S/V470H/L472S, Y464H/V470S/L472S, Y464S/V470H/L472H, Y464H/V470S/L472H, Y464H/V470H/L472S, Y464D/V470D/L472H, Y464D/V470H/L472D, Y464H/V470D/L472D, Y464D/V470H/L472H, Y464H/V470D/L472H, Y464H/V470H/L472D, Y464D/V470R/L472H, Y464D/V470S/L472H, Y464H/V470H/L472H, Y464T/V470T/L472T, Y464A/V470A/L472A.

In the present specification, with regard to the positions in a glucose dehydrogenase corresponding to the 464th position, 470th position and 472nd position of the amino acid sequence of SEQ ID NO: 1, the phrase the "amino acid is substituted" means that the wild type amino acid at the position in the glucose dehydrogenase is excluded and the amino acid is substituted to an amino acid other than the wild type amino acid. For example, in some GDHs, the amino acid at the position corresponding to the 470th position of SEQ ID NO: 1 is alanine (for example, MrdGDH, SEQ ID NO: 4). In such GDH, alanine is excluded from the substituted amino acid at the position corresponding to the 470th position of the amino acid sequence of SEQ ID NO: 1, and an amino acid other than alanine, for example, a polar amino acid may be substituted in place. For example, in some GDHs, the amino acid at the position corresponding to the 472nd position of SEQ ID NO: 1 is lysine (for example, MgGDH, SEQ ID NO: 6). In such GDH, lysine is excluded from the substituted amino acid at the position corresponding to the 472nd position of the amino acid sequence of SEQ ID NO: 1 and a polar amino acid other than lysine or alanine may be substituted in place. For example, in some GDHs, the amino acid at the position corresponding to the 464th position of SEQ ID NO: 1 is tyrosine (see, for example, FIG. 1-3). In such GDH, tyrosine is excluded from the substituted amino acid at the position corresponding to the 464th position of the amino acid sequence of SEQ ID NO: 1 and a polar amino acid other than tyrosine or alanine may be substituted in place. In the case of GDH in which the amino acid at the position corresponding to the 464th position of SEQ ID NO: 1 is not tyrosine (see, for example, Satake, et al., J. Biosci. Bioeng., (2015), Vol. 120, Issue 5, November 2015, 498-503), the amino acid at said position may be substituted with tyrosine.

(Homologous Region)

The amino acid sequence identity or homology can be computed by using a program such as maximum matching or search homology of GENETYX Ver.11 (manufactured by Genetics Inc.), or a program such as maximum matching or multiple alignment of DNASIS Pro (Hitachi Solutions Co., Ltd.). In order to compute amino acid sequence identity, positions having identical amino acids between two or more GDHs when said two or more GDHs are aligned can be investigated. Based on such information, identical regions between the amino acid sequences can be determined.

Further, the positions having similar amino acids in two or more GDHs can be investigated. For example, a plurality of amino acid sequences can be aligned with CLUSTALW. In this case, using the Blosum62 algorithm, amino acids determined as being similar (analogous) when a plurality of amino acid sequences are aligned, may be referred to as similar amino acids. In the mutants of the present invention, amino acid substitution(s) may be between such similar amino acids. By such alignment, regions having identical amino acid sequences and positions occupied by similar amino acids can be investigated in a plurality of amino acid sequences. Based on such information, a homologous region (conserved region) in an amino acid sequence can be determined.

In the present specification, the "homologous region" is specified as a region consisting of identical amino acids or similar amino acids which are present in the corresponding positions between a standard GDH and a GDH being compared when two or more GDHs are aligned, wherein said region consists of 3 or more, 4 or more, 5 or more, 6 or more, 7 or more, 8 or more, 9 or more or 10 or more continuous amino acids. For example, in FIG. 1, GDHs having 70% or more full-length amino acid sequence identity were aligned. Of these, taking the GDH from the genus *Mucor* and represented by SEQ ID NO: 1 as a standard (basis), the amino acids from the 31st to 41st position consist of identical amino acids and, therefore, the region from the 31st to 41st position is a homologous region. Similarly, when using the GDH from the genus *Mucor* of SEQ ID NO: 1 as the standard, the regions consisting of 58 to 62nd position, 71 to 85th position, 106 to 116th position, 119 to 127th position, 132 to 134th position, 136 to 144th position, 150 to 157th position, 167 to 171st position, 219 to 225th position, 253 to 262nd position, 277 to 281st position, 301 to 303rd position, 305 to 312nd position, 314 to 319th position, 324 to 326th position, 332 to 337th position, 339 to 346th position, 348 to 354th position, 388 to 394th position, 415 to 417th position, 454 to 456th position, 478 to 484th position, 486 to 491st position, 508 to 511st position, 564 to 579th position, 584 to 586th position, 592 to 605th position, 607 to 617th position, and 625 to 630th position may be homologous regions.

In one embodiment, the homologous region of GDH is, based on the GDH from the genus *Mucor* of SEQ ID NO: 1 as the standard, the region consisting of amino acid sequences from 32 to 38th position, 58 to 62nd position, 76 to 82nd position, 106 to 109th position, 111 to 116th position, 119 to 126th position, 132 to 134th position, 136 to 144th position, 150 to 153rd position, 167 to 171st position, 222 to 225th position, 253 to 262nd position, 277 to 281st position, 301 to 303rd position, 305 to 312nd position, 314 to 319th position, 324 to 326th position, 332 to 337th position, 339 to 346th position, 348 to 354th position, 388 to 390th position, 415 to 417th position, 454 to 456th position, 478 to 482nd position, 486 to 491st position, 508 to 511st position, 564 to 567th position, 570 to 579th position, 584 to 586th position, 592 to 595th position, 597 to 599th position, 601 to 604th position, 607 to 609th position, 611 to 617th position, and 625 to 630th position.

In one embodiment, the homologous region of GDH is, based on the GDH from the genus *Mucor* of SEQ ID NO: 1 as the standard, the region consisting of amino acid sequences from 32 to 34th position, 58 to 62nd position, 106 to 109th position, 111 to 116th position, 119 to 126th position, 132 to 134th position, 136 to 144th position, 150 to 153rd position, 167 to 171st position, 222 to 225th position, 253 to 262nd position, 277 to 281st position, 301 to 303rd position, 305 to 312nd position, 314 to 319th position, 324 to 326th position, 332 to 337th position, 339 to 346th position, 388 to 390th position, 415 to 417th position, 454 to 456th position, 486 to 491st position, 508 to 511st position, 564 to 567th position, 570 to 574th position, 584 to 586th position, 592 to 594th position, 597 to 599th position, 601 to 604th position, 607 to 609th position, 611 to 617th position, and 625 to 630th position.

The GDH of the present invention, when aligned with GDH having the amino acid sequence of SEQ ID NO: 1, has a full-length amino acid sequence identity of 50% or more, 55% or more, 60% or more, 65% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, for example 99% or more, and has glucose dehydrogenase activity. Further, the amino acid sequence in the homologous region of the GDH mutant of the present invention has a sequence identity of 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, for example 99% or more, with the amino acid sequence of the homologous region in SEQ ID NO: 1.

(Further Substitutions)
(Amino Acid Substitution Improving Thermal Stability of GDH)

The present inventors previously reported that the thermal stability of GDH can be improved by substituting an amino acid residue thereof (see, for example, WO 2012/169512, the entire content of which is incorporated in the present specification by reference). The GDH of the present invention may optionally have such further amino acid substitution(s).

As exemplary amino acid substitutions for changing the substrate specificity or improving thermal stability of a GDH, amino acid substitutions to the positions corresponding to the following positions in the amino acid sequence of SEQ ID NO: 1 may be mentioned.
  (a) 232nd position
  (b) 387th position
  (c) 545th position.

Optionally, the amino acid at the position corresponding to (a) the 232nd position may be substituted with alanine, methionine, cysteine, glutamine or glutamic acid.
Optionally, the amino acid at the position corresponding to glutamine at (b) the 387th position may be substituted with alanine, valine, glycine, serine or cysteine.
Optionally, the amino acid at the position corresponding to alanine at (c) 545th position may be substituted with valine, threonine, serine, proline, alanine, tyrosine, lysine, histidine, phenylalanine or glutamic acid.

Further, the present inventors previously reported that the thermal stability of GDH can be improved by substituting an amino acid residue thereof (see, for example, WO 2015/099112 the entire content of which is incorporated in the present specification by reference). The GDH of the present invention may optionally have such further amino acid substitution.

Exemplary amino acid substitutions for improving thermal stability of GDH include amino acid substitutions to the positions corresponding to the following positions in the amino acid sequence of SEQ ID NO: 1.
  (d) 66th position
  (e) 68th position
  (f) 88th position
  (g) 158th position
  (h) 233rd position
  (i) 385th position
  (j) 391st position
  (k) 557th position
  (l) 559th position Optionally, the amino acid at the position corresponding to (d) the 66th position may be substituted with tyrosine.
Optionally, the amino acid at the position corresponding to (e) the 68th position may be substituted with glycine.
Optionally, the amino acid at the position corresponding to (0 the 88th position may be substituted with alanine. Optionally, the amino acid at the position corresponding to (g) the 158th position may be substituted with histidine.
Optionally, the amino acid at the position corresponding to (h) the 233rd position may be substituted with arginine.
Optionally, the amino acid at the position corresponding to (i) the 385th position may be substituted with threonine.
Optionally, the amino acid at the position corresponding to (j) the 391st position may be substituted with isoleucine.
Optionally, the amino acid at the position corresponding to (k) the 557th position may be substituted with valine.
Optionally, the amino acid at the position corresponding to (l) the 559th position may be substituted with lysine.

(Amino Acid Substitution for Improving Specific Activity of GDH)

The present inventors previously reported that the specific activity of GDH can be improved by substituting an amino acid residue thereof (see, for example, WO 2015/129475, the entire content of which is incorporated in the present specification by reference). The GDH of the present invention may optionally include such further amino acid substitution.

As the amino acid substitution for improving specific activity of GDH, amino acid substitution for the positions corresponding to the following positions in the amino acid sequence of SEQ ID NO: 1 may be mentioned.
  (m) 88th position
  (n) 554th position Optionally, the amino acid at the position corresponding to (m) the 88th position may be substituted with alanine.
Optionally, the amino acid at the position corresponding to (n) the 554th position may be substituted with aspartic acid.

(Enzyme Chemical Characteristics of the Flavin Bound GDH of the Present Invention)

In one embodiment, the GDH of the present invention has the following properties.
Action: exhibits glucose dehydrogenase activity; and is capable of directly transferring an electron from the enzyme to an electrode in the absence of a mediator,
Molecular weight: the molecular weight estimated based on the primary sequence of the polypeptide chain portion of the protein is about 70 kDa or the molecular weight measured by SDS-polyacrylamide electrophoresis is about 80 kDa,
Substrate specificity: the reactivity to maltose and D-xylose is low compared to the reactivity to D-glucose,
Cofactor characteristics: is a flavin bound (binding) type and comprises at least one amino acid substitution within the molecule, for example, a particular region within the molecule.

In one embodiment, the GDH of the present invention has low reactivity to D-galactose, compared to the reactivity to D-glucose. In the present specification, the phrase that reactivity to a sugar is low compared to the reactivity to D-glucose means that the activity to the sugar is less than 5%, for example, less than 4%, less than 3%, less than 2%, for example, less than 1.5% based on activity to D-glucose (100%).

The molecular weight can be calculated based on the information of a primary sequence by using a program such as GENETYX Ver.11 (manufactured by Genetics Inc.) and ExPASy (web dot expasy dot org/computepi) or can be measured by SDS-polyacrylamide electrophoresis. When calculation is made by using, for example, GENETYX Ver.11, the molecular weight estimated from the primary sequence of the flavin-bound GDH having the amino acid sequence of SEQ ID NO: 1 is 70 kDa. When the molecular weight is measurement is made by using, for example, SDS-polyacrylamide electrophoresis, the molecular weight of the flavin-bound GDH having the amino acid sequence of SEQ ID NO: 1 is about 80 kDa.

In one embodiment, the present invention provides a DNA encoding a glucose dehydrogenase. In one embodiment, the present invention provides a DNA encoding the amino acid sequence of SEQ ID NO: 12 or a DNA having the nucleotide sequence of SEQ ID NO: 13. In one embodiment, the present invention provides DNA having a nucleotide sequence having a sequence identity of 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 90%, 90%, 91%, 92%, 93%, 94%, 95%, 96%, 97%, 98% or 99% or more with the nucleotide sequence of SEQ ID NO: 13 and encoding a protein having a glucose dehydrogenase activity which can directly transfer an electron in the absence of a mediator. (GDH Gene)

In order to obtain a gene encoding a GDH a gene cloning method carried out in the art in general can be used. For example, chromosomal DNA or mRNA can be extracted from microbial cells or various cells having GDH productivity by a routine method, for example, a method described in Current Protocols by Molecular Biology (WILEY Interscience, 1989). Further, cDNA can be synthesized using mRNA as a template. Using chromosomal DNA or cDNA thus obtained, a library of chromosomal DNA or cDNA can be prepared.

Next, an appropriate probe DNA can be synthesized based on the amino acid sequence of the GDH above and a GDH gene can be screened from the chromosomal DNA or cDNA library by using the probe DNA or, alternatively, appropriate primer DNA(s) can be prepared based on the amino acid sequence above and the DNA containing the gene fragment of interest encoding the GDH can be amplified with an appropriate polymerase chain reaction (PCR method) such as the 5'RACE method and the 3'RACE method, and then, these DNA fragments can be linked to obtain a DNA containing the full-length GDH gene of interest.

Examples of a gene encoding a GDH obtained as mentioned above include a GDH gene from the genus *Mucor* (described in JP Patent No. 4648993). A gene obtained by modifying this GDH gene may be used including, for example, modified genes described in WO 2012/169512 and WO 2015/099112.

These GDH gene may be ligated or inserted into various vectors or integrated in a chromosome or a genome. In the case of using a vector, cloning of the gene into the vector can be carried out by using a commercially available kit such as TA Cloning Kit (Invitrogen) and In-Fusion HD Cloning Kit (Clontech); commercially available plasmid vector DNA such as pUC119 (manufactured by Takara Bio Inc.), pUC18 (manufactured by Takara Bio Inc.), pBR322 (manufactured by Takara Bio Inc.), pBluescript SK+(Stratagene) and pYES2/CT (Invitrogen); and/or commercially available bacteriophage vector DNA such as λEMBL3 (Stratagene). Using such recombinant DNA, a host organism, for example, *Escherichia coli*, preferably *Escherichia coli* JM109 strain (manufactured by Takara Bio Inc.) or *Escherichia coli* DH5 α strain (manufactured by Takara Bio Inc.) can be transformed. Recombinant DNA contained in the resultant transformants is purified by, e.g., QIAGEN Plasmid Mini Kit (manufactured by QIAGEN Genomics Inc.).
(Treatment for Inducing Mutation of GDH Gene)

A method for obtaining the GDH of the present invention starting from a known GDH is as follows. A mutation is introduced into the starting GDH gene and GDHs expressed by various mutant genes can be subjected to selection or screening based on the enzymological properties as an index.

Mutation of the starting GDH gene can be performed by any known method depending on the intended form of mutation. That is, methods of bringing a chemical agent serving as a mutagen into contact with and allowing to act on a GDH gene or recombinant DNA comprising said gene integrated therein; ultraviolet irradiation methods; genetic engineering techniques; protein engineering methods; or a combination of these can be used extensively.

Examples of the chemical agent serving as the mutagen used in the above mutation treatment include hydroxylamine, N-methyl-N'-nitro-N-nitrosoguanidine, nitrous acid, sulfurous acid, hydrazine, formic acid or 5-bromouracil and the like.

The conditions for allowing a chemical agent to contact and act can be determined depending on the type of chemical agent being used and the like and the conditions are not particularly limited as long as the desire mutation can actually be induced in the GDH gene. A desire mutation can be induced usually by allowing a chemical agent preferably having a concentration of 0.5 to 12 M to contact and act on (the gene) at a reaction temperature of 20 to 80° C. for 10 minutes or more and preferably 10 to 180 minutes. In the case of ultraviolet irradiation, a mutation can be induced with a routine method as mentioned above (Modern Chemistry, p. 24 to 30, June, 1989).

As a method of employing protein engineering procedures, in general, a method known as a Site-Specific Mutagenesis can be used. Examples thereof include the Kramer method (Nucleic Acids Res., 12, 9441 (1984): Methods Enzymol., 154, 350 (1987): Gene, 37, 73 (1985)), the Eckstein method (Nucleic Acids Res., 13, 8749 (1985): Nucleic Acids Res., 13, 8765 (1985): Nucleic Acids Res, 14, 9679 (1986)) and the Kunkel method (Proc. Natl. Acid. Sci. U.S.A., 82, 488 (1985): Methods Enzymol., 154, 367 (1987)). Examples of a specific method for converting the nucleotide sequence in DNA include methods using a commercially available kit (e.g., Transformer Mutagenesis Kit; Clonetech, EXOIII/Mung Bean Deletion Kit; manufactured by Stratagene, Quick Change Site Directed Mutagenesis Kit; manufactured by Stratagene).

Further, the method known as the general PCR method (Polymerase Chain Reaction) can be used (Technique, 1, 11 (1989)). Incidentally, apart from the above gene modifying methods, a modified GDH gene of interest can be directly synthesized using organic synthesis methods or enzyme synthesis methods.

The nucleotide sequence of the DNA of the GDH gene obtained by the method above can be determined or confirmed using, for example, multi-capillary DNA analysis system CEQ2000 (manufactured by Beckman Coulter, Inc.) and the like.
(Vector Having an Insertion of the GDH Gene of the Present Invention and Host Cell)

The GDH gene of the present invention obtained as described above can be integrated into a vector such as a bacteriophage, cosmid, or a plasmid for transformation of prokaryote cells or eukaryote cells according to routine methods and the host cell corresponding to the vector can be transformed or transduced with routine methods.

Examples of the prokaryotic host cell that can be used herein include, microorganisms belonging to the genus *Escherichia* such as *Escherichia coli* K-12 strain, *Escherichia coli* BL21 (DE3), *Escherichia coli* JM109, *Escherichia coli* DH5a, *Escherichia coli* W3110, and *Escherichia coli* C600 (all are manufactured by Takara Bio Inc.). These microbial cells can be transformed or transduced to obtain host cells having DNA introduced therein (transformants). As a method for introducing a recombinant vector into a host cell, if the host cell is a microorganism belonging to *Escherichia coli*, a method of transferring recombinant DNA in the presence of a calcium ion can be employed. Furthermore, an electroporation method may be used. Moreover, commercially available competent cells (for example, ECOS Competent *Escherichia coli* BL21 (DE3); manufactured by Nippon Gene Co., Ltd.) may be used.

Incidentally, the present inventors have previously confirmed that by truncating the N terminal signal peptide of a natural GDH, the productivity thereof in a microbial host such as *Escherichia coli* can be improved (see, for example, WO 2012/169512). If a microorganism such as *Escherichia coli* is used as a host, then the N terminal signal peptide of the GDH of the present invention can optionally be truncated.

The N terminal signal peptide of the GDH from the genus *Mucor* of SEQ ID NO: 1 is a peptide consisting of amino acids from the 1st to 20th position of the amino acid sequence of SEQ ID NO: 1. Cleavage occurs between alanine at the 20th position and glutamine at the 21st position. In order to delete the N terminal signal peptide from this polypeptide, a codon encoding alanine at the 20th position or a codon encoding glutamine at the 21st position may be substituted with an initiation codon. The same applies to the positions corresponding to the 20th positions or 21st positions (SEQ ID NO: 1) of other GDHs having sequence identity with SEQ ID NO: 1.

Examples of the eukaryotic host cell include yeast. Examples of microorganisms classified as yeast include yeasts belonging to the genus *Zygosaccharomyces*, the genus *Saccharomyces*, the genus *Pichia* and the genus *Candida*. The gene insert may contain a marker gene which enables selecting transformed cells. Examples of the marker gene include genes which compensate auxotrophy of a host cell, such as URA3 and TRP1. The gene insert may desirably contain a promoter enabling expression of the gene of the present invention in a host cell or other regulatory sequences (for example, secretory signal sequence, enhancer sequence, terminator sequence, polyadenylation sequence and the like). Specific examples of the promoter include GAL1 promoter and ADH1 promoter. As methods for transforming yeast, known methods such as the method of using lithium acetate (Methods Mol. Cell. Biol., 5, 255-269 (1995)) as well as electroporation (J Microbiol Methods 55 (2003) 481-484) can suitably be used although the transformation method is not limited thereto. Various methods including the spheroplast method and glass bead method can be used for transformation.

Other examples of the eukaryotic host cell include filamentous fungi such as those of the genus *Aspergillus* and the genus *Tricoderma*. The method for preparing a transformant of a filamentous fungus is not particularly limited and includes, for example, a method of inserting a gene encoding a GDH to a host filamentous fungus with routine methods such that the gene encoding the GDH is expressed. More specifically, a DNA construct is prepared by inserting a gene encoding a GDH between an expression inducing promoter and a terminator; and then, a host filamentous fungus is transformed with the DNA construct containing the gene encoding the GDH to obtain transformants overexpressing the gene encoding the GDH. In the present specification, a DNA fragment consisting of an expression inducing promoter-GDH encoding gene-terminator, and a recombinant vector comprising said DNA fragment, produced to transform a host filamentous fungus, are collectively referred to as DNA constructs.

The method for inserting a gene encoding a GDH into a host filamentous fungus such that the gene is expressed is not particularly limited and includes, for example, a method of directly inserting the gene into the chromosome of a host organism by using homologous recombination; and a method of ligating the gene to a plasmid vector and introducing the vector to a host filamentous fungus.

In the method using homologous recombination, a DNA construct is inserted into the genome of the host filamentous fungus by ligating the DNA construct between sequences homologous to the upstream region and downstream region of a recombination site on the chromosome. By overexpressing the gene under control of its own high expression promotor in the host filamentous fungus a transformant by self-cloning can be obtained. Examples of the high expression promoter include, but are not particularly limited to, the promoter region of TEF1 gene (tef1) serving as a translation elongation factor, the promoter region of α-amylase gene (amy) and the promoter region of an alkaline protease gene (alp).

In the method of using a vector, a DNA construct is integrated into a plasmid vector used in transformation of filamentous fungi by a routine method and then the corresponding host filamentous fungus can be transformed (with the plasmid vector) with a routine method.

Such suitable vector-host system is not particularly limited as long as the GDH can be produced in the host filamentous fungus and includes, for example, pUC19 and filamentous fungus system, pSTA14 (Mol. Gen. Genet. 218, 99-104, 1989) and filamentous fungus system.

It is preferably to use the DNA construct by introducing the same into the chromosome of a host filamentous fungus. However, as an alternative method, the DNA construct can be integrated into an autonomous replicating vector (Ozeki et al. Biosci. Biotechnol. Biochem. 59, 1133 (1995)). In this manner, the DNA construct can be used without being introduced into the chromosome.

The DNA construct may comprise a marker gene which enables a transformed cell to be selected. Examples of the marker gene include, but are not particularly limited to, genes compensating auxotrophy of a host such as pyrG, niaD, adeA; and drug resistance genes against chemical agents such as pyrithiamine, hygromycin B and oligomycin. Further, the DNA construct preferably comprises a promoter enabling overexpression of the gene encoding the GDH in the host cell, a terminator and other regulatory sequences (for example, enhancer, polyadenylation sequence). Examples of the promoter include, but are not particularly limited to, suitable expression induction promoters and constitutive promoters, such as the tef1 promoter, alp promoter, amy promoter and the like. Examples of the terminator include, but are not particularly limited to, the alp terminator, amy terminator and tef1 terminator and the like.

In the DNA construct, if the DNA fragment containing the gene encoding the GDH to be inserted has a sequence having expression regulating function, then an expression regulatory sequence for the gene encoding the GDH need not be required. When transformation is carried out by a co-transformation method, the DNA construct need not have a marker gene in some cases.

One embodiment of the DNA construct is e.g., a DNA construct prepared by ligating tef1 gene promoter, a gene encoding GDH, alp gene terminator and pyrG marker gene to the In-Fusion Cloning Site present in the multiple cloning site of pUC19.

As a method for transforming filamentous fungi, methods known to those skilled in the art can appropriately be selected, for example, a protoplast PEG method can be used, in which a protoplast of a host filamentous fungus is prepared, and then, polyethylene glycol and calcium chloride are used (see, for example, Mol. Gen. Genet. 218, 99-104, 1989, JP Patent Publication (Kokai) No. 2007-222055A). As the culture medium for regenerating a transformed filamentous fungus, an appropriate culture medium is used depending on the host filamentous fungus to be used and the transformation marker gene. For example, if *Aspergillus soya* is used as the host filamentous fungus and pyrG gene is used as the transformation marker gene, the transformed filamentous fungus can be regenerated in Czapek-Dox minimal medium (Difco) containing for example, 0.5% agar and 1.2 M sorbitol.

To obtain, for example, the transformed filamentous fungus of the present invention, the promoter of the gene encoding the GDH that the host filamentous fungus originally has in the chromosome may be substituted with a high expression promoter such as tef1, by using homologous recombination. In this case, a transformation marker gene such as pyrG is preferably inserted in addition to the high expression promoter. For example, for this purpose, a transformation cassette consisting of an upstream region of a gene encoding GDH-transformation marker gene-high expression promoter-whole or part of gene encoding GDH, can be used (see, Example 1 and FIG. 1 in JP Patent Publication (Kokai) No. 2011-239681A). In this case, the upstream region of a gene encoding GDH and the whole or part of the gene encoding GDH are used for homologous recombination. As the whole or part of the gene encoding GDH, a region containing the initiation codon up to a midstream region can be used. The length of the region suitable for homologous recombination is preferably 0.5 kb or more.

Whether the transformed filamentous fungus of the present invention was produced or not can be confirmed by culturing the transformed filamentous fungus of the present invention under conditions where GDH enzyme activity can be confirmed and then confirming the GDH activity in a culture obtained after culturing.

Further, whether the transformed filamentous fungus of the present invention was produced or not can be confirmed by extracting chromosomal DNA from a transformed filamentous fungus, subjecting the chromosomal DNA to PCR using the chromosomal DNA as the template and confirming production of a PCR product that can be amplified if transformation took place.

For example, PCR is carried out by using a forward primer to the nucleotide sequence of the applied promoter in combination with a reverse primer to the nucleotide sequence of the transformation marker gene, and then, whether or not a product having the estimated length is obtained, is confirmed.

(Screening of a Host Cell Producing the GDH of the Present Invention)

To efficiently screen a transformed filamentous fungus producing the GDH of the present invention, the following method, for example, may be used. From a minimal medium containing 0.5% agar and having colonies of host cells (transformants) formed thereon, a colony is picked up, inoculated in a DPY liquid medium (1% (w/v) polypeptone, 2% (w/v) dextrin, 0.5% (w/v) yeast extract, 0.5% (w/v) $KH_2PO_4$, 0.05% (w/v) $MgSO_4.7H_2O$) and cultured for 3 days while shaking. The resultant culture supernatant is mixed with a reaction solution (10 mM phosphate buffer (pH 7.0) containing glucose, DCIP or cytochrome c) having a composition that can develop color or change color if GDH acts thereon, and then the degree of color change of purple color from DCIP or reddish brown from cytochrome c is observed. In the case of a GDH which requires a mediator such as PMS for transferring electrons, the degree of color change is low in the reaction solution without any mediator; however, in the case of the GDH of the present invention having modified electron transfer properties, for example, in the case of GDH which can directly transfer electrons, the degree of color change of the reaction solution is high. Utilizing this and by comparing with the degree of color change in the reaction solution containing a wild type GDH producing strain, transformants which can produce GDH having modified electron transfer properties, for example, GDH which can directly transfer electrons, can be screened.

To efficiently screen transformed *Escherichia coli* producing the GDH of the present invention, for example, the following method may be used. Several sheets of replicas are produced from LB agar medium having colonies of the resultant host cells (transformants) by using sterilized velvet fabric and the like onto new agar media and then the same is cultured. When colonies of the replica agar mediums reach a sufficient size, a membrane impregnated with a lysing agent such as lysozyme is overlaid on the culture medium and allowed to stand at room temperature for about one hour to allow for lysis. At this time, crude enzyme solution of the lysate is adsorbed onto the membrane.

Then, said membrane with the adsorbed crude enzyme solution is allowed to stand at 35° C. for one minute to one hour and a membrane impregnated with a reaction solution (10 mM phosphate buffer (pH 7.0) containing glucose, DCIP or cytochrome c) whose composition is prepared such that if GDH functions, a color changes is overlaid thereon. Then, the degree of a change of purple color from DCIP or reddish brown from cytochrome c is observed. In the case of a GDH requiring a mediator such as PMS for transferring electrons, the degree of color-change of colonies is low in a reaction solution without any mediator; however, in the GDH of the present invention having modified electron transfer properties, for example, in the case of GDH that can directly transfer an electron, the degree of color change of colonies is high. Utilizing this and by comparing the degree of color change to that of a strain producing a wild type GDH, transformants producing a GDH having modified electron transfer properties, for example, a GDH capable of directly transferring an electron, can be screened.

If necessary, mutation(s) can further be repeatedly introduced to the gene encoding a GDH having modified electron transfer properties found in this manner, and further excellently modified GDHs and transformants having the capability to produce the same can be obtained.

(High Throughput Screening)

A GDH can further be subjected to high throughput screening in order to obtain a functional GDH mutant. For example, a library of transformed strains or transduced strains comprising mutated GDH genes can be prepared and then the library may be subjected to high throughput screening based on a microtiter plate or to ultrahigh-throughput screening based on droplet microfluids. As an example, a combinatorial library of mutant genes encoding variants is constructed and then a large population of modified GDHs is screened by using, e.g., phage display (for example, Chem. Rev. 105 (11): 4056-72, 2005); yeast display (for example, Comb Chem High Throughput Screen. 2008; 11 (2): 127-34); bacterial display (for example, Curr Opin Struct Biol 17: 474-80, 2007) and the like. Also see, Agresti, et al., "Ultrahigh-throughput screening in drop-based microfluidics for directed evolution" Proceedings of the National Academy of Sciences 107 (9): 4004-4009 (March, 2010). The contents of this document on the ultrahigh-throughput screening method that may be used for screening GDH variants is incorporated herein by reference. For example, a library can be constructed by an error-prone PCR method. Further, saturation mutagenesis may be used to introduce mutations into the region(s) or position(s) described herein or the corresponding region(s) or position(s) thereto as the target to construct a library. Using such library, appropriate cells such as electrocompetent EBY-100 cells, can be transformed and about 10 to the power of seven mutants can be obtained. Yeast cells transformed with said library can subsequently be subjected to cell sorting. A polydimethoxysiloxane (PDMS) microfluidic device prepared by a standard soft lithography method may be used. Monodispersed droplets can be formed using a flow focus device. Formed droplets containing individual mutants can be subjected to an appropriate sorting device. When screening cells, the presence or absence of GDH activity can be utilized. For this purpose, the reaction solution having a composition capable of developing color or undergoing a color change if GDH functions, may, for example, be used. For example, in the case of using cytochrome c, absorbance at 550 nm may be measured using a 96 well plate, a 192 well plate, a 384 well plate or a 9600 well plate and a plate reader. Mutation and screening can be repeated a plurality of times.

(Production of GDH of the Present Invention)

The GDH of the present invention may be produced by culturing a host cell producing the GDH of the present invention and obtained as mentioned above, expressing the GDH gene contained in said host cell, and then isolating a GDH protein from the culture.

When culturing a microbial host cell, culturing can be carried out at a culture temperature of 10 to 42° C., preferably about 25° C. for several hours to several days, further preferably at a culture temperature of about 25° C. preferably for 1 to 7 days with aerated and agitated deep culture, shaking culture or stationary culture. Both synthetic medium and natural medium can be used, as long as it is a culture medium usually used for culturing filamentous fungi, i.e., containing a carbon source, a nitrogen source, inorganic substances and other nutrients in appropriate ratios. As the culture medium for culturing the above microbial host cell, a culture medium prepared by adding, one or more nitrogen source such as yeast extract, tryptone, peptone, meat extract, corn steep liquor or soy or wheat bran steep liquor, one or more inorganic salts such as sodium chloride, primary potassium phosphate, secondary phosphate, magnesium sulfate, magnesium chloride, ferric chloride, ferric sulfate or manganese sulfate, and if necessary, further adding a sugar source, and vitamins and the like where appropriate, is used.

For culture conditions, culture conditions for filamentous fungi widely known to those skilled in the art can be employed and can be appropriately designed, for example, the initial pH of a culture medium can be adjusted to 5 to 10; for example, the culture temperature can be 20 to 40° C., the culture time can be from several hours to several days, preferably 1 to 7 days, and more preferably 2 to 5 days. The culture means is not particularly limited and although aeration stirring deep culture, shaking culture and static culture and the like can be employed, it is preferable that culture is performed in conditions where sufficient dissolved oxygen is present. Examples of culture medium and culture conditions for culturing Aspergillus microorganism include a shaking culture using a DPY culture medium performed at 30° C. and 160 rpm for 3 to 5 days, described later in the Examples.

After completion of culture, the GDH of the present invention is recovered from the culture. This can be carried out by known enzyme sampling means used routinely. For example, the supernatant of the culture is collected, or a fungus body is subjected to, a routine treatment such as ultrasonication disruption treatment or grinding treatment; or the GDH of the invention is extracted by using a lytic enzyme such as lysozyme or yatarase. Alternatively, the fungus body is shaken or allowed to stand in the presence of toluene and the like to cause cell lysis and in this manner, the GDH of the invention can be discharged out of the fungus body. Subsequently, the lysis solution is filtered or centrifuged and solid matter is removed and, if necessary, nucleic acid is removed by streptomycin sulfate, protamine sulfate, or manganese sulfate and the like. To the resultant, ammonium sulfate, an alcohol and/or acetone is(are) added, the mixture is fractionated and a precipitate is collected to obtain a crude enzyme of the GDH of the present invention.

The crude enzyme of the GDH of the present invention can be further purified by any means known in the art. A purified enzyme preparation can be obtained by a method appropriately selected from, for example, a gel filtration method using Sephadex, ultrogel or bio gel; an adsorption elution method using an ion exchanger; an electrophoretic method using, e.g., polyacrylamide gel; an adsorption elution method using hydroxyapatite; a sedimentation method such as a sucrose density gradient centrifugation method; an affinity chromatography method; and a fractionation method using, e.g., a molecular sieve membrane or a hollow fiber membrane, or by using these methods in combination. In this manner, a purified GDH enzyme preparation of the present invention can be obtained.

(Measuring Activity of the GDH of the Present Invention)

The GDH of the present invention catalyzes the reaction of oxidizing a hydroxyl group of a glucose to generate glucono-δ-lactone.

Activity of the GDH of the present invention can be measured based on this principle of action and by using, for example, the following measurement system which employs phenazine methosulfate (PMS) and 2,6-dichloroindophenol (DCIP) as electron acceptors.

(Reaction 1) D-glucose+PMS (oxidized form)
→D-glucono-δ-lactone+PMS (reduced type)

(Reaction 2) PMS (reduced type)+DCIP (oxidized form)
→PMS (oxidized form)+DCIP (reduced type)

More specifically, first, in (Reaction 1), as oxidation of D-glucose proceeds, PMS (reduced type) is generated. Subsequently, (Reaction 2) proceeds, in which as oxidation of PMS (reduced type) proceeds, DCIP is reduced. The degree of disappearance of "DCIP (oxidized form)" is detected as the amount of change in absorbance at a wavelength of 600 nm and based on this amount of change, the enzyme activity can be determined.

More specifically, the activity of GDH can be measured with the following procedure. 2.05 mL of 100 mM phosphate buffer (pH 7.0), 0.6 mL of 1M D-glucose solution and 0.15 mL of 2 mM DCIP solution are mixed and kept at a temperature of 37° C. for 5 minutes. To the mixture, 0.1 mL of a 15 mM PMS solution and 0.1 mL of the enzyme sample solution are added to initiate the reaction. Absorbance is measured at the initiation of the reaction and over time. The decrease of absorbance at 600 nm per minute as the enzymatic reaction proceeds (ΔA600) is obtained and GDH activity is computed with the following formula. Here, 1U of GDH activity is defined as the enzyme amount required for reducing 1 μmol of DCIP at 37° C. in the presence of D-glucose (concentration 200 mM) per minute.

$$GDH \text{ activity (U/mL)} = \frac{-(\Delta A600 - \Delta A600_{blank}) \times 3.0 \times df}{16.3 \times 0.1 \times 1.0} \quad \text{[Formula 1]}$$

Note that, in the formula, the numerical value 3.0 represents the amount (mL) of liquid (reaction reagent+enzyme reagent), the numerical value 16.3 represents the millimolar molecular extinction coefficient ($cm^2/\mu mol$) under this activity measurement condition; the numerical value 0.1 represents the amount of enzyme solution (mL), the numerical value 1.0 represents the optical path length of the cell (cm), $\Delta A600_{blank}$ represents the decrease in absorbance at 600 nm per minute in the case where 100 mM phosphate buffer (pH 7.0) is added instead of the enzyme sample solution and the reaction is initiated; and df represents the dilution factor.

(Method for Measuring Glucose with the GDH of the Present Invention)

In one embodiment, the present invention provides a glucose assay kit comprising the GDH of the present invention. By using this kit, glucose in the blood (blood glucose level) can be measured using the GDH of the present invention. Measurement may be carried out continuously.

The glucose assay kit of the present invention comprises the GDH of the present invention at an amount sufficient for at least one assay. Typically, the glucose assay kit of the present invention comprises, other than the GDH of the present invention, a buffer solution required for the assay, a glucose standard solution for preparing a calibration curve and instructions. In one embodiment, the glucose assay kit of the present invention, for example, the glucose assay kit for SMBG, CGM or FGM, comprises a mediator. In one embodiment, the glucose assay kit of the present invention, for example, the glucose assay kit for SMBG, CGM or FGM need not include a mediator. The GDH of the present invention can be provided in various forms, for example, as a freeze dried reagent, a reagent immobilized onto beads or an electrode surface, or a solution stored in a proper preservation solution.

Measurement of glucose concentration in the case of a colorimetric glucose assay kit is, for example, carried out as follows. In the reaction layer of the glucose assay kit, a liquid or solid state composition containing GDH and at least one selected from the group consisting of N-(2-acetamide)imide diacetate (ADA), bis(2-hydroxyethyl)iminotris (hydroxy methyl) methane (Bis-Tris), sodium carbonate and imidazole as a reaction accelerator are placed. Here, if necessary, a pH buffer and a coloring reagent (discoloration reagent) are added. To this, a sample containing glucose is added and allowed to react for a predetermined time. During this time period, a dye polymerized and generated by directly receiving an electron from the GDH during the reaction or the absorbance corresponding to the maximum absorption wavelength of the reduced dye is monitored. The glucose concentration in the sample can be calculated from the rate of change of absorbance per time if a rate method is used or from the rate of change of absorbance up to the time point where glucose in the sample is completely oxidized if an endpoint method is employed, based on a calibration curve prepared in advance using a standard-concentration glucose solution.

Examples of a coloring reagent (discoloration reagent) to be used in this method include 2,6-dichloroindophenol (DCIP) which can be added as an electron acceptor and the amount of glucose can be determined by monitoring the decrease in absorbance at 600 nm. Glucose concentration can be calculated by adding nitrotetrazolium blue (NTB) as a coloring reagent and measuring the absorbance at 570 nm to determine the amount of generated diformazan. Incidentally, needless to say, the coloring reagent (discoloration reagent) to be used is not limited to these.

(Glucose Sensor Containing the GDH of the Present Invention)

In one embodiment, the present invention provides a glucose sensor using the GDH of the present invention. As an electrode, e.g., a carbon electrode, a gold electrode or a platinum electrode can be used and the GDH enzyme of the present invention can be applied or immobilized onto the electrode. Examples of the immobilization method include a method using a cross-linking agent, a method of embedding in a polymer matrix, a method of coating (covering) with a dialysis membrane, methods of using a photo-crosslinkable polymer, conductive polymer or redox polymer and the like, and the GDH may be immobilized in a polymer or may be immobilized by adsorption on an electrode, or these methods may be used in combination. Typically, the GDH of the present invention is immobilized onto a carbon electrode by using glutaraldehyde and thereafter treated with a reagent having an amine group to block glutaraldehyde.

The GDH of the present invention can be applied to various electrochemical measurement methods by using, a potentiostat, a galvanostat and the like. Examples of the electrochemical measurement method include, various methods such as amperometry, voltammetry, potentiometry and coulometry and the like. For example, by using the amperometric method and measuring the current when glucose is reduced, it is possible to calculate the glucose concentration of a sample. The voltage to be applied varies depending on the conditions and setting of the apparatus and can be set to be, for example, −1000 mV to +1000 mV (vs. Ag/AgCl).

Glucose concentration can be measured as follows. To a constant-temperature cell, a buffer solution is added and the temperature is held constant. An electrode to which the GDH of the present invention is immobilized is used as the working electrode, and a counter electrode (for example, platinum electrode) and a reference electrode (for example, Ag/AgCl electrode) are used. A constant voltage is applied to the carbon electrode and when the current becomes stationary, a sample containing glucose is added and the increase of current is measured. Based on a calibration curve prepared by using a standard-concentration glucose solution, the glucose concentration of the sample can be calculated.

As a specific example, 0.2 U to 150 U, more preferably, 0.5 U to 100 U of the GDH of the present invention is immobilized to a glassy carbon (GC) electrode and the response current value corresponding to the glucose concentration is measured. To an electrolytic cell is added 10.0 ml of 100 mM potassium phosphate buffer (pH 6.0). A GC electrode is connected to a potentiostat BAS100B/W (manufactured by BAS) and the solution is stirred at 37° C. and then, a voltage of +500 mV is applied to a silver-silver chloride reference electrode. To this system, a 1 M D-glucose solution is added so as to obtain a final concentration of 5, 10, 20, 30, 40 or 50 mM and for each addition, the current value at a constant state is measured. These current values are plotted relative to corresponding glucose concentrations already known (5, 10, 20, 30, 40, 50 mM) to obtain a calibration curve. In this manner, the amount of glucose can be determined by an enzyme-immobilized electrode using the glucose dehydrogenase of the present invention.

Further, a printed electrode can also be used for electrochemical measurement. This enables reducing the amount of solution required for measurement. In this case, it is preferable that the electrode is formed on an insulating substrate. More specifically, it is desirable to form the electrode on a substrate by a printing technique such as photolithographic technology, screen printing, gravure printing and flexographic printing. Exemplary materials for the insulating substrate include, silicon, glass, ceramic, polyvinyl chloride, polyethylene, polypropylene and polyester and it is more preferable to use a material having high resistance to various solvents and chemical agents.

Regarding the Mediator

In the measuring method, a kit, an apparatus and a sensor of the present invention, a mediator (also referred to as an artificial electron mediator, an artificial electron acceptor, an electron mediator) can be used. The mediator is not particularly limited as long as it can receive an electron from the GDH of the present invention. Examples of the mediator include quinones, phenazines, viologens, cytochromes (for example, cytochrome b, cytochrome c), phenoxazines, phenothiazines, a ferricyanide, for example potassium ferricyanide, ferredoxins, ferrocene, an osmium complex, and derivatives thereof. Examples of the phenazine compound include, but are not limited to, for example PMS, and methoxy PMS.

In one embodiment, the GDH of the present invention has amino acid substitution and having modified electron transfer properties. Without wishing to be bound to any particular theory, in one embodiment it is believed that electron transfer from the GDH enzyme to another electron acceptor substance is facilitated via the substituted amino acid(s) introduced into the GDH of the present invention. Without wishing to be bound to any particular theory, in one embodiment it is believed that histidine introduced into the GDH of the present invention interacts with a metal ion and promotes electron transfer from the GDH enzyme to another electron acceptor substance or an electrode. It is known that the surface of a carbon electrode is negatively charged in neutral to basic conditions (see, JP Patent Publication (Kokai) No. H8-5600A, 1996). Accordingly, without wishing to be bound to any particular theory, if arginine, lysine or histidine, which are positive charges, is present in proximity to the active site of an enzyme, the distance between an electrode and these amino acids may be reduced by electrostatic interaction. As a result, it is considered possible that the distance between the electrode and the active site of the enzyme may also be shortened and electron transfer from the enzyme to electrode can be enhanced. Without wishing to be bound to any particular theory, in one embodiment, it is considered possible for the aspartic acid introduced in the GDH of the present invention to increase the electron density of the region in proximity to said aspartic acid, and facilitate electron transfer from the GDH enzyme to another electron acceptor substance or electrode. The same effect is expected for glutamic acid as well. In one embodiment, electron transfer from the GDH enzyme of the present invention to another electron acceptor substance can occur even in the presence of a mediator reduced in concentration, compared to the case of the enzyme prior to modification. In one embodiment, electron transfer from the GDH enzyme of the present invention to another electron acceptor substance can occur in the absence of a mediator. In one embodiment, the GDH enzyme of the present invention is capable of directly transferring an electron from the enzyme to an electrode.

In one embodiment, electron transfer from the GDH enzyme of the present invention to another electron acceptor substance is possible even for certain types of mediators for which it was difficult to transfer electrons using the enzyme before modification. For example, a ruthenium compound does not generate a response current in a glucose concentration-dependent manner unless a second mediator such as mPMS co-exists with the ruthenium compound in glucose measurement using a conventional glucose dehydrogenase (see, JP Patent Publication (Kokai) No. 2013-083634A). The GDH of the present invention having modified electron transfer properties can be used in glucose measurement in combination with a ruthenium compound without using a second mediator such as mPMS. As a further example, the GDH of the present invention having modified electron transfer properties can be used in glucose measurement in combination with cytochrome c without using a second mediator such as mPMS.

The GDH of the present invention having modified electron transfer properties can be used in the same manner as in conventional GDHs. The GDH of the present invention can be used for measuring glucose concentration in the sample and this can be useful for diagnosing diabetes and self-monitoring blood glucose levels. The GDH of the present invention can be used as an enzyme electrode and can be used for various electrochemical measurements. Further, the GDH of the present invention can be used as an enzyme sensor. Further, the GDH of the present invention can be used in a glucose measurement kit and a glucose sensor. The above are merely examples and use of the modified GDH of the present invention is not limited thereto.

The present invention will be further illustrated by way of the following Examples. However, the technical scope of the present invention is not limited by these examples in any way.

EXAMPLES

Example 1

1. Introduction of the GDH from the Genus *Mucor* Gene to a Host and Confirmation of GDH Activity To explain briefly, first, to the gene encoding a GDH from the genus *Mucor* (MpGDH, SEQ ID NO: 1), individual mutations of N66Y/N68G/C88A/Q233R/T387C/E554D/L557V/S559K were introduced to obtain a gene encoding a modified GDH (hereinafter also referred to as MpGDH-M1). The amino acid sequence of MpGDH-M1 is shown in SEQ ID NO: 10. The nucleotide sequence of the gene is shown in SEQ ID NO: 11. The target MpGDH-M1 gene was inserted into the multiple cloning site of plasmid pUC19 with routine methods to obtain a DNA construct. More specifically, as pUC19, the pUC19 linearized Vector provided with the In-Fusion HD Cloning Kit (Clontech) was used. To the In-Fusion Cloning Site present in the multiple cloning site of pUC19, the MpGDH-M1 gene was ligated by using the In-Fusion HD Cloning Kit mentioned above according to the protocol attached to the kit to obtain a plasmid construct (pUC19-MpGDH-M1).

Using the resultant recombinant plasmid pUC19-MpGDH-M1 as the template and synthetic oligonucleotides of SEQ ID NOs: 15 and 16 and KOD-Plus- (manufactured by Toyobo Co., Ltd.), PCR was performed with the following conditions.

More specifically, 5 µl of 10×KOD-Plus-buffer solution, 5 µl of dNTP mixture solution which was prepared such that the dNTPs are contained at a concentration of 2 mM each, 2 µl of 25 mM $MgSO_4$ solution, 50 ng of DNA construct ligated with the MpGDH-M1 gene serving as the template, 15 pmol each of the aforementioned synthetic oligonucleotides and 1 unit of KOD-Plus- were mixed and then sterile water was added up to a total amount of 50 µl. The reaction solution thus prepared was subjected to a thermal cycler (manufactured by Eppendorf) in which incubation was performed at 94° C. for 2 minutes, and then, a cycle of a reaction at "94° C. for 15 seconds", reaction at "50° C. for 30 seconds" and reaction at "68° C. for 8 minutes" was repeated 30 times.

An aliquot was taken from the reaction solution and electrophoresed on a 1.0% agarose gel to confirm that a DNA fragment of about 8,000 bp in size was specifically amplified. The DNA fragment thus obtained was treated with restriction enzyme DpnI (manufactured by NEW ENGLAND BIOLABS) to cleave the residual template DNA, and thereafter, *Escherichia coli* JM109 was transformed and inoculated on a LB-amp agar medium. The grown colonies were inoculated on 2.5 ml of LB-amp medium [1% (W/V) bactotrypton, 0.5% (W/V) peptone, 0.5% (W/V) NaCl, 50 µg/ml Ampicillin] and subjected to shaking culture at 37° C. for 20 hours to obtain a culture. The culture was centrifuged at 7,000 rpm for 5 minutes and a bacterial body was collected. Then, from the bacterial body, the recombinant plasmid was extracted and purified using QIAGEN tip-100 (manufactured by QIAGEN) to obtain 2.5 µg of DNA. The nucleotide sequence of the DNA encoding MpGDH-M1 in the plasmid was sequenced using multicapillary DNA analysis system, Applied Biosystems 3130x1 genetic analyzer (manufactured by Life Technologies). As a result, a DNA construct (SEQ ID NO: 13) encoding MpGDH-M1/Y464C/V470C/L472C (SEQ ID NO: 12), a triple mutant in which tyrosine at the 464th position, valine at the 470th position and leucine at the 472nd position of the amino acid sequence of SEQ ID NO: 1 are all substituted with cysteine, was obtained.

The gene was expressed in *Aspergillus sojae* and GDH activity thereof was evaluated.

More specifically, using a gene encoding a GDH from the genus *Mucor* as the starting material and modifying the same in order to obtain the GDH of the present invention, a GDH gene suitable for recombinant expression in *Aspergillus sojae* was designed. More specifically, a gene sequence was designed based on the sequence of the GDH gene of SEQ ID NO: 1 by matching the codon usage to that of the host and said gene was totally synthesized. The sequence of totally synthesized DNA is shown in SEQ ID NO: 2.

Double-joint PCR (Fungal Genetics and Biology, Vol. 41, p. 973-981, 2004) was carried out to construct a cassette consisting of 5' arm region-PyrG gene (uracil auxotrophic marker)-TEF1 promoter gene-flavin bound GDH gene-3' arm region and this was used for transformation of *Aspergillus soya* NBRC4239 derived pyrG disrupted strain (strain deficient in 48 bp upstream, 896 bp of coding region, and 240 bp downstream of pyrG gene). To polypeptone dextrin liquid medium (100 ml) comprising 20 mM uridine and placed in a 500 ml Erlenmeyer flask, conidia of the pyrG disrupted strain from *Aspergillus soya* NBRC4239 were inoculated and subjected to shaking culture at 30° C. for about 20 hours, and then, fungus bodies were collected. A protoplast was prepared from the fungus bodies collected. Using the resultant protoplast and 20 µg of DNA construct comprising the inserted target gene, transformation was carried out with the protoplast PEG method. Then, incubation was carried out using Czapek-Dox minimal medium (Difco; pH 6) containing 0.5% (w/v) agar and 1.2 M sorbitol at 30° C. for 5 days or more to obtain transformed *Aspergillus soya* having colony forming ability.

The resultant transformed *Aspergillus soya* is capable of growing on uridine-free medium due to introduction of the pyrG gene which complements uridine auxotrophy, thereby enabling selection of strains having the target gene introduced therein. Of the resultant strains, a transformant of interest was confirmed with PCR and selected.

Using *Aspergillus soya* transformants transformed with a MpGDH-M1 or MpGDH-M1/Y464CN470C/L472C gene, each GDH was produced.

To 40 ml of DPY liquid medium (1% (w/v) polypeptone, 2% (w/v) dextrin, 0.5% (w/v) yeast extract, 0.5% (w/v) $KH_2PO_4$, 0.05% (w/v) $MgSO_4.7H_2O$; pH not adjusted) placed in a 200 ml-Erlenmeyer flask, conidia of each strain were inoculated and subjected to shaking culture at 160 rpm and 30° C. for 4 days. Then, the culture was filtered to filter off fungus body. The resultant supernatant fraction was concentrated by Amicon Ultra-15, 30K NMWL (manufactured by Millipore) up to 10 mL and applied to HiLoad 26/60 Superdex 200 pg (manufactured by GE healthcare) equilibrated with a 20 mM potassium phosphate buffer (pH 6.5) containing 150 mM NaCl and eluted with the same buffer. Fractions exhibiting GDH activity were collected to obtain a purified product of MpGDH-M1 or MpGDH-M1/Y464CN470C/L472C.

Chronoamperometry

Using a purified enzyme of MpGDH-M1 or MpGDH-M1/Y464CN470C/L472C, chronoamperometry was carried out with a printed electrode measurement. More specifically, on a DEP Chip electrode (attached with a circular carbon dam ring; manufactured by BioDevice Technology) having a glassy carbon working electrode and a silver-silver chloride reference electrode printed thereon, a solution in which a phosphate buffer (pH 7.0) having a final concentration of about 100 mM and 135 U purified enzyme MpGDH-M1 solution or 128 U purified enzyme MpGDH-M1/Y464CN470C/L472C solution were dissolved in 15 µL was placed. Thereafter, the DEP Chip electrode was connected to ALS electrochemical analyzer 814D (manufactured by BAS) by using a DEP Chip specific connector. Then, a voltage of +300 mV or +500 mV (vs. Ag/AgCl) was applied, 5 µL of a 100 mM glucose solution was placed on the electrode to carry out the reaction and a current value was measured for 120 seconds.

Figure 3:
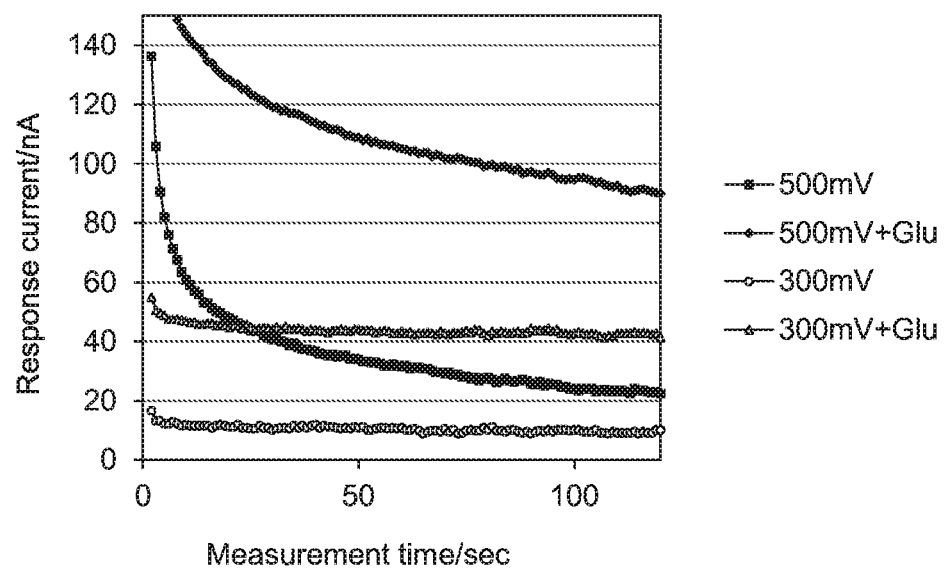

Results are shown in FIGS. 2 and 3. FIG. 2 shows chronoamperometric measurement results of MpGDH-M1 enzyme having no cysteine residue introduced therein. In neither cases of 300 mV and 500 mV, a significant difference in response current was observed in the presence or absence of glucose. FIG. 3 shows chronoamperometric measurement results of the MpGDH-M1/Y464C/V470C/L472C enzyme, a triple mutant having cysteine residues introduced therein. In both cases of +300 mV and +500 mV (vs. Ag/AgCl), a significantly high response current was observed when glucose was added. Even at an applied voltage of +300 mV (vs. Ag/AgCl), a response current as high as 31 nA was exhibited 120 seconds after initiation of measurement.

Confirmation Test to Demonstrate that Substrate Specificity is Maintained

MpGDH-M1 enzyme has a high substrate specificity and reactivities to maltose and D-xylose are low compared to the reactivity to D-glucose. Whether or not such high substrate specificity is maintained was checked even if the triple mutation Y464C/V470C/L472C is introduced into the MpGDH-M1 enzyme. When setting activity of MpGDH-M1/Y464CN470C/L472C to D-glucose as 100%, the activity to maltose and D-xylose were 1.1% and 1.0%, respectively. Accordingly, it can be said that the GDH of the present invention prepared by introducing the triple mutation Y464C/V470C/L472C into MpGDH-M1 shows high substrate specificity, more specifically, the GDH exhibits high reactivity to D-glucose; whereas it rarely exhibits almost no reactivity to maltose or D-xylose.

From the above observation, since a response current was generated even in the absence of a mediator, it is believed that when the GDH of the present invention oxidizes glucose to gluconolactone, an electron is directly transferred from the enzyme to an electrode. To date it has not been reported that a GDH or GOD capable of directly transferring an electron from the enzyme to an electrode can be obtained by only introducing an amino acid substitution into a GDH which does not have any cytochrome domain.

Example 2

Measurement of response current in the case where various mutations were introduced into the GDH from the genus *Mucor*

In the same manner as in Example 1, PCR was performed using the recombinant plasmid pUC19-MpGDH-M1 as the template and using synthetic oligonucleotides of ID NOs: 17 and 18 to obtain a DNA construct encoding MpGDH-M1/Y464C, which is a mutant obtained by substituting tyrosine at the 464th position of the amino acid sequence of SEQ ID NO: 1 with cysteine, in accordance with the method described in the instruction of KOD-Plus-Mutagenesis Kit (Code No. SMK-101, manufactured by Toyobo Co., Ltd.). Subsequently, the gene was expressed in *A. sojae* in the same manner as in Example 1 to obtain a purified product.

Using a purified enzyme of MpGDH-M1 or MpGDH-M1/Y464C, chronoamperometry was carried out with a printed electrode measurement. More specifically, onto the working electrode on a DEP Chip electrode, a solution containing 80 μg of purified enzyme MpGDH-M1 or a solution containing 80 μg of purified enzyme MpGDH-M1/Y464C was added, and then dried in air at room temperature. Subsequently, 10 μL of a 20 mM phosphate buffer (pH 7.5)/1.5 M potassium chloride/20 mM glucose solution was placed on the electrode and allowed to react. Then, a voltage of +300 mV (vs. Ag/AgCl) was applied and the current value was measured for 60 seconds. As a control, a solution containing no glucose was subjected to the same measurement. Comparison was made based on a value obtained by subtracting the response current value obtained by measurement of the solution containing no glucose from the response current value obtained by measurement of the solution containing glucose.

As a result, the value obtained by subtracting the response current value obtained by measurement of the solution containing no glucose from the response current value of measurement of the solution containing glucose, was 2 nA and no substantial difference was observed. In contrast, the measurement result (value) in the case of MpGDH-M1/Y464C enzyme exhibited a high value of 14 nA.

Subsequently, in the same manner as above, PCR was performed using the recombinant plasmid pUC19-MpGDH-M1 as the template and using synthetic oligonucleotides of SEQ ID Nos. in the following table to obtain DNA constructs encoding the following mutants.

SEQ ID NO: 21, 22: MpGDH-M1/Y464C/L472C
SEQ ID NO: 23, 24: MpGDH-M1/V470C
SEQ ID NO: 25, 26: MpGDH-M1/L472C
SEQ ID NO: 27, 28: MpGDH-M1/V470C/L472C
SEQ ID NO: 29, 30: MpGDH-M1/Y464S
SEQ ID NO: 31, 32: MpGDH-M1/Y464A
SEQ ID NO: 33, 34: MpGDH-M1/Y464D
SEQ ID NO: 35, 36: MpGDH-M1/Y464T
SEQ ID NO: 37, 38: MpGDH-M1/V470A
SEQ ID NO: 39, 40: MpGDH-M1N470S
SEQ ID NO: 41, 42: MpGDH-M1/V470T
SEQ ID NO: 43, 44: MpGDH-M1/Y464S/V470S/L472S
SEQ ID NO: 45, 46: MpGDH-M1/Y464D/V470D/L472D
SEQ ID NO: 51, 52: MpGDH-M1/Y464H/V470H/L472H.

Subsequently, PCR was carried out using synthetic oligonucleotides of SEQ ID NOs: 47 and 48 and using pUC19-MpGDH-M1/Y464D as the template to obtain a DNA construct encoding MpGDH-M1/Y464D/V470R/L472H. Further, PCR was carried out using synthetic oligonucleotides of SEQ ID NOs: 49 and 50 and using pUC19-MpGDH-M1/Y464D as the template to obtain a DNA construct encoding MpGDH-M1/Y464D/V470S/L472H. Subsequently, the genes were expressed in *A. sojae* in the same manner as in Example 1 to obtain purified products.

Using a purified enzyme of MpGDH-M1/Y464C/L472C, MpGDH-M1/V470C, MpGDH-M1/L472C, MpGDH-M1/V470C/L472C, MpGDH-M1/Y464D/V470D/L472D or MpGDH-M1/Y464H/V470H/L472H, chronoamperometry was carried out with the printed electrode measurement. More specifically, onto the working electrode on a DEP Chip electrode, a solution containing 80 μg of each purified enzyme was added and then dried in air at room temperature. Subsequently, 10 μL of a 20 mM phosphate buffer (pH 7.5)/1.5M potassium chloride/20 mM glucose solution was placed on the electrode and allowed to react. A voltage of +300 mV (vs. Ag/AgCl) was applied and the current value for 60 seconds was measured. As a control, a solution containing no glucose was subjected to the same measurement. Comparison was made based on a value obtained by subtracting the response current value obtained by measurement of the solution containing no glucose from the response current value obtained by measurement of the solution containing glucose. Measurements showed high values and the measurement result of MpGDH-M1/Y464C/L472C enzyme was 10 nA; the measurement result of MpGDH-M1/V470C enzyme was 12 nA; the measurement result of MpGDH-M1/L472C enzyme was 10 nA; the measurement result of MpGDH-M1/V470C/L472C enzyme was 20 nA; the measurement result of MpGDH-M1/Y464D/V470D/L472D enzyme was 63 nA; and the measurement result of MpGDH-M1/Y464H/V470H/L472H enzyme was 31 nA.

Using a purified enzyme of each of MpGDH-M1, MpGDH-M1/Y464C/L472C, MpGDH-M1/Y464A, MpGDH-M1/Y464S, MpGDH-M1/Y464D, MpGDH-M1/Y464T, MpGDH-M1/V470A, MpGDH-M1/V470S, MpGDH-M1N470T, MpGDH-M 1/Y464S/V470S/L472S, MpGDH-M1/Y464D/V470R/L472H and MpGDH-M1/Y464D/V470S/L472H, chronoamperometry was carried out with the printed electrode measurement in the same manner as above. However, the applied voltage was +500 mV (vs. Ag/AgCl) here.

The measurement result of MpGDH-M1 enzyme was 5 nA; however, measurements of the mutants showed high values and the measurement result of MpGDH-M1/Y464C/L472C enzyme was 27 nA; the measurement result of MpGDH-M1/Y464A enzyme was 13 nA; the measurement result of MpGDH-M1/Y464S enzyme was 16 nA; the measurement result of MpGDH-M1/Y464D enzyme was 12 nA; the measurement result of MpGDH-M1/Y464T enzyme was 22 nA; the measurement result of MpGDH-M1/V470A enzyme was 28 nA; the measurement result of MpGDH-M1/V470S enzyme was 15 nA; the measurement result of MpGDH-M1/V470T enzyme was 9 nA; the measurement result of MpGDH-M1/Y464S/V470S/L472S enzyme was 22 nA; the measurement result of MpGDH-M1/Y464D/V470R/L472H enzyme was 19 nA; and the measurement result of MpGDH-M1/Y464D/V470S/L472H enzyme was 144 nA.

Example 3

Mutation into MrdGDH and Response Current Measurement

A gene encoding the GDH from *Mucor* RD056860 (MrdGDH) was obtained (see, WO 2013/118798). The amino acid sequence of MrdGDH is shown in SEQ ID NO: 4, and the nucleotide sequence of the gene of MrdGDH is shown in SEQ ID NO: 53. PCR was performed in the same manner as in Example 2 by using synthetic oligonucleotides of SEQ ID NOs: 54 and 55. A DNA construct encoding MrdGDH/Y461C/A467C/L469C, which is a mutant obtained by substituting tyrosine at the 461st position of the amino acid sequence of SEQ ID NO: 4 with cysteine; alanine at the 467th position thereof with cysteine and leucine at the 469th position thereof with cysteine. Subsequently, the genes encoding MrdGDH and MrdGDH/Y461C/A467C/L469C were expressed in *A. sojae* in the same manner as in Example 1 to obtain purified products and the response current was measured.

Using purified enzymes of MrdGDH and MrdGDH/Y461C/A467C/L469C, chronoamperometry was carried out with the printed electrode measurement in the same manner as in Example 1, except that 130 µg of purified enzyme was applied to the working electrode and dried in air; a voltage of +500 mV (vs. Ag/AgCl) was applied; and measurement time was 40 seconds.

The measurement result of MrdGDH enzyme was 16 nA; however, the measurement result (response current) of MrdGDH/Y461C/A467C/L469C enzyme was as high as 24 nA.

INDUSTRIAL APPLICABILITY

By using the glucose dehydrogenase of the present invention, glucose can be measured in the presence of a mediator reduced in concentration than those of conventional measurements or in the absence of a mediator. Further, the glucose dehydrogenase of the present invention can be used in a glucose sensor and in continuous glucose measurement.

Brief Description of Sequences

SEQ ID NO: 1 Amino acid sequence of the GDH from *Mucor prainii* (MpGDH)
SEQ ID NO: 2 Nucleotide sequence of MpGDH gene
SEQ ID NO: 3 Amino acid sequence of the GDH from *Mucor hiemalis* (MhGDH)
SEQ ID NO: 4 Amino acid sequence of the GDH from *Mucor* RD056860 (MrdGDH)
SEQ ID NO: 5 Amino acid sequence of the GDH from *Mucor subtilissimus* (MsGDH)
SEQ ID NO: 6 Amino acid sequence of the GDH from *Mucor guilliermondii* (MgGDH)
SEQ ID NO: 7 Amino acid sequence of the GDH from *Circinella simplex* (CsGDH)
SEQ ID NO: 8 Amino acid sequence of the GDH from genus *Circinella* (CrGDH)
SEQ ID NO: 9 Amino acid sequence of the GDH from *Mucor circinelloides* (McGDH)
SEQ ID NO: 10 Amino acid sequence of MpGDH-M1 glucose dehydrogenase
SEQ ID NO: 11 Nucleotide sequence of MpGDH-M1 gene
SEQ ID NO: 12 Amino acid sequence of MpGDH-M1/Y464C/V470C/L472C triple mutant
SEQ ID NO: 13 Nucleotide sequence of a gene encoding the polypeptide of SEQ ID NO: 12
SEQ ID NO: 14 Motif sequence Cys-Xaa-Xaa-Xaa-Xaa-Xaa-Cys-Xaa-Cys
SEQ ID NO: 15 to 52 Primers
SEQ ID NO: 53 the GDH from *Mucor* RD056860 (MrdGDH)
SEQ ID NO: 54 to 55 Primers All publications, patents and patent applications used in the present specification are incorporated herein in their entirety by reference.

The invention claimed is:

1. A glucose dehydrogenase mutant having at least one amino acid substitution, and being capable of transferring an electron from the enzyme directly to an electrode wherein, in said glucose dehydrogenase mutant, the full length amino acid sequence of said glucose dehydrogenase mutant has an amino acid sequence identity of 90% or more with the amino acid sequence of SEQ ID NO: 1 or SEQ ID NO: 4, and said glucose dehydrogenase mutant has glucose dehydrogenase activity capable of transferring an electron from the enzyme directly to an electrode,
wherein:
the amino acid at the position corresponding to the 464th position of SEQ ID NO: 1 is substituted with a polar amino acid or alanine,
the amino acid at the position corresponding to the 470th position of SEQ ID NO: 1 is substituted with a polar amino acid or alanine, or
the amino acid at the position corresponding to the 472nd position of SEQ ID NO: 1 is substituted with a polar amino acid or alanine.

2. A glucose dehydrogenase mutant having at least one amino acid substitution, and being capable of transferring an electron from the enzyme directly to an electrode, wherein said glucose dehydrogenase mutant is a flavin adenine dinucleotide dependent glucose dehydrogenase mutant having an amino acid sequence identity of 90% or more with the amino acid sequence of SEQ ID NO: 1 or SEQ ID NO: 4,
wherein,
the amino acid at the position corresponding to the 464th position of SEQ ID NO: 1 is substituted with a polar amino acid or alanine,
the amino acid at the position corresponding to the 470th position of SEQ ID NO: 1 is substituted with a polar amino acid or alanine, or
the amino acid at the position corresponding to the 472nd position of SEQ ID NO: 1 is substituted with a polar amino acid or alanine wherein,
(i) when the amino acid sequence of the glucose dehydrogenase mutant is aligned with the amino acid sequence of SEQ ID NO: 1,
the glucose dehydrogenase mutant comprises a substitution with a polar amino acid or alanine, or a substitution of an amino acid selected from the group consisting of cysteine, aspartic acid, histidine, serine, alanine, threonine and arginine at least 1, 2 or 3 positions corresponding to the 464th position and 472nd position of the amino acid sequence of SEQ ID NO: 1; and
comprises glucose dehydrogenase activity capable of transferring an electron from the enzyme directly to an electrode,
(ii) with regard to the glucose dehydrogenase mutant of said (i), the glucose dehydrogenase mutant has an amino acid sequence comprising a substitution, deletion or addition of one or several amino acids at a position other than the position(s) having the above amino acid substitution introduced thereto, and comprises glucose dehydrogenase activity capable of transferring an electron from the enzyme directly to an electrode,
(iii) with regard to the glucose dehydrogenase mutant of said (i), the full length amino acid sequence of said glucose dehydrogenase mutant has an amino acid sequence identity of 90% or more with the amino acid sequence of SEQ ID NO: 1 or SEQ ID NO: 4; and has glucose dehydrogenase activity capable of transferring an electron from the enzyme directly to an electrode,
(iv) the amino acid residues at the positions corresponding to the positions of the 464th position, 470th position and 472nd position of the amino acid sequence of SEQ ID NO: 1 are cysteine,
(v) the amino acid residues at the positions corresponding to the positions of the 464th position, 470th position and 472nd position of the amino acid sequence of SEQ ID NO: 1 are aspartic acid, or
(vi) the amino acid residues at the positions corresponding to the positions of the 464th position, 470th position and 472nd position of the amino acid sequence of SEQ ID NO: 1 are histidine.

3. The glucose dehydrogenase mutant according to claim 1, wherein,
the amino acid at the position corresponding to the 464th position of the amino acid sequence of SEQ ID NO: 1 is substituted with an amino acid selected from the group consisting of cysteine, aspartic acid, histidine, serine, alanine and threonine,
the amino acid at the position corresponding to the 470th position of the amino acid sequence of SEQ ID NO: 1 is substituted with an amino acid selected from the group consisting of cysteine, aspartic acid, histidine, serine, alanine, threonine and arginine, or
the amino acid at the position corresponding to the 472nd position of the amino acid sequence of SEQ ID NO: 1 is substituted with an amino acid selected from the group consisting of cysteine, aspartic acid, histidine and serine.

4. The glucose dehydrogenase mutant according to claim 1, wherein
2 or 3 amino acids at the positions corresponding to the 464th position, 470th position or 472nd position of the amino acid sequence of SEQ ID NO: 1 are substituted with cysteine;
2 or 3 amino acids at the positions corresponding to the 464th position, 470th position or 472nd position of the amino acid sequence of SEQ ID NO: 1 are substituted with aspartic acid, or
2 or 3 amino acids at the positions corresponding to the 464th position, 470th position or 472nd position of the amino acid sequence of SEQ ID NO: 1 are substituted with histidine.

5. A gene encoding a glucose dehydrogenase having modified electron transfer properties said gene consisting of
(a) DNA encoding the FAD dependent glucose dehydrogenase according to claim 1,
(b) DNA encoding the amino acid sequence of SEQ ID NO: 12, or
(c) DNA comprising the nucleotide sequence of SEQ ID NO: 13.

6. A vector comprising the gene according to claim 5.

7. An isolated recombinant host cell comprising the vector according to claim 6.

8. A method for producing a glucose dehydrogenase comprising the following steps:
culturing the host cell according to claim 7,
expressing the glucose dehydrogenase gene contained in the host cell, and
recovering glucose dehydrogenase from the culture.

9. A method for measuring glucose, said method comprising contacting the glucose dehydrogenase mutant of claim 1 with a sample containing glucose.

10. A glucose measuring kit comprising the glucose dehydrogenase of claim 1.

11. An electrode comprising the glucose dehydrogenase of claim 1.

12. A glucose sensor comprising the electrode of claim 11.

* * * * *

SEQUENCE LISTING

```
<160> NUMBER OF SEQ ID NOS: 55

<210> SEQ ID NO 1
<211> LENGTH: 641
<212> TYPE: PRT
<213> ORGANISM: Mucor prainii

<400> SEQUENCE: 1

Met Lys Ile Thr Ala Ala Ile Ile Thr Val Ala Thr Ala Phe Ala Ser
1               5                   10                  15

Phe Ala Ser Ala Gln Gln Asp Thr Asn Ser Ser Ser Thr Asp Thr Tyr
                20                  25                  30

Asp Tyr Val Ile Val Gly Gly Gly Val Ala Gly Leu Ala Leu Ala Ser
            35                  40                  45

Arg Ile Ser Glu Asn Lys Asp Val Thr Val Ala Val Leu Glu Ser Gly
        50                  55                  60

Pro Asn Ala Asn Asp Arg Phe Val Val Tyr Ala Pro Gly Met Tyr Gly
65                  70                  75                  80

Gln Ala Val Gly Thr Asp Leu Cys Pro Leu Ile Pro Thr Thr Pro Gln
                85                  90                  95

Glu Asn Met Gly Asn Arg Ser Leu Thr Ile Ala Thr Gly Arg Leu Leu
                100                 105                 110
```

-continued

Gly Gly Gly Ser Ala Ile Asn Gly Leu Val Trp Thr Arg Gly Gly Leu
            115                 120                 125

Lys Asp Tyr Asp Ala Trp Glu Glu Leu Gly Asn Pro Gly Trp Asn Gly
130                 135                 140

Ala Asn Leu Phe Lys Tyr Phe Lys Lys Val Glu Asn Phe Thr Pro Pro
145                 150                 155                 160

Thr Pro Ala Gln Ile Glu Tyr Gly Ala Thr Tyr Gln Lys Ser Ala His
                165                 170                 175

Gly Lys Lys Gly Pro Ile Asp Val Ser Phe Thr Asn Tyr Glu Phe Ser
            180                 185                 190

Gln Ser Ala Ser Trp Asn Ala Ser Leu Glu Thr Leu Asp Phe Thr Ala
        195                 200                 205

Leu Pro Asp Ile Leu Asn Gly Thr Leu Ala Gly Tyr Ser Thr Thr Pro
    210                 215                 220

Asn Ile Leu Asp Pro Glu Thr Val Gln Arg Val Asp Ser Tyr Thr Gly
225                 230                 235                 240

Tyr Ile Ala Pro Tyr Thr Ser Arg Asn Asn Leu Asn Val Leu Ala Asn
                245                 250                 255

His Thr Val Ser Arg Ile Gln Phe Ala Pro Lys Asn Gly Ser Glu Pro
            260                 265                 270

Leu Lys Ala Thr Gly Val Glu Trp Tyr Pro Thr Gly Asn Lys Asn Gln
        275                 280                 285

Lys Gln Ile Ile Lys Ala Arg Tyr Glu Val Ile Ile Ser Ser Gly Ala
    290                 295                 300

Ile Gly Ser Pro Lys Leu Leu Glu Ile Ser Gly Ile Gly Asn Lys Asp
305                 310                 315                 320

Ile Val Ser Ala Ala Gly Val Glu Ser Leu Ile Asp Leu Pro Gly Val
                325                 330                 335

Gly Ser Asn Met Gln Asp His Val His Ala Ile Thr Val Ser Thr Thr
            340                 345                 350

Asn Ile Thr Gly Tyr Thr Thr Asn Ser Val Phe Val Asn Glu Thr Leu
        355                 360                 365

Ala Gln Glu Gln Arg Glu Glu Tyr Glu Ala Asn Lys Thr Gly Ile Trp
    370                 375                 380

Ala Thr Thr Pro Asn Asn Leu Gly Tyr Pro Thr Pro Glu Gln Leu Phe
385                 390                 395                 400

Asn Gly Thr Glu Phe Val Ser Gly Lys Glu Phe Ala Asp Lys Ile Arg
                405                 410                 415

Asn Ser Thr Asp Glu Trp Ala Asn Tyr Tyr Ala Ser Thr Asn Ala Ser
            420                 425                 430

Asn Val Glu Leu Leu Lys Lys Gln Tyr Ala Ile Val Ala Ser Arg Tyr
        435                 440                 445

Glu Glu Asn Tyr Leu Ser Pro Ile Glu Ile Asn Phe Thr Pro Gly Tyr
    450                 455                 460

Glu Gly Ser Gly Asn Val Asp Leu Gln Asn Asn Lys Tyr Gln Thr Val
465                 470                 475                 480

Asn His Val Leu Ile Ala Pro Leu Ser Arg Gly Tyr Thr His Ile Asn
                485                 490                 495

Ser Ser Asp Val Glu Asp His Ser Val Ile Asn Pro Gln Tyr Tyr Ser
            500                 505                 510

His Pro Met Asp Ile Asp Val His Ile Ala Ser Thr Lys Leu Ala Arg
        515                 520                 525

Glu Ile Ile Thr Ala Ser Pro Gly Leu Gly Asp Ile Asn Ser Gly Glu

```
                530               535               540
Ile Glu Pro Gly Met Asn Ile Thr Ser Glu Asp Asp Leu Arg Ser Trp
545               550               555               560

Leu Ser Asn Asn Val Arg Ser Asp Trp His Pro Val Gly Thr Cys Ala
                565               570               575

Met Leu Pro Lys Glu Leu Gly Gly Val Val Ser Pro Ala Leu Met Val
                580               585               590

Tyr Gly Thr Ser Asn Leu Arg Val Val Asp Ala Ser Ile Met Pro Leu
                595               600               605

Glu Val Ser Ser His Leu Met Gln Pro Thr Tyr Gly Ile Ala Glu Lys
                610               615               620

Ala Ala Asp Ile Ile Lys Asn Phe Tyr Lys Thr Gln His Lys Asn Gln
625               630               635               640

Asn

<210> SEQ ID NO 2
<211> LENGTH: 1926
<212> TYPE: DNA
<213> ORGANISM: Mucor prainii

<400> SEQUENCE: 2
atgaagatca cagctgccat tatcactgtt gccacagcat ttgcttcttt tgcttctgct      60
caacaagaca caaattcttc ctcaactgat acttatgatt atgttatcgt tggcggcggt     120
gtagctggtt tggctttggc tagtcgtatc tctgaaaaca aggatgtcac tgttgctgtt     180
ctcgagtccg gtcctaatgc aatgataga tttgttgttt atgctcctgg catgtatggc     240
caagctgttg gcactgatct ctgtcctctc attcctacta ctcctcaaga aaatatgggc     300
aacagaagtc tcacaatcgc tactggtaga ttgctcggtg gtggcagtgc tattaatggt     360
ctcgtttgga cccgtggtgg cttgaaggat tacgatgctt gggaggagct cggtaaccct     420
ggatggaacg gtgccaactt gttcaagtac tttaagaagg tcgaaaactt cactcctcct     480
actcctgccc aaattgaata cggcgctact tatcagaaaa gtgctcatgg caagaaggga     540
cctattgatg tctctttcac gaactacgag ttctctcaat ctgctagctg aaacgcctca     600
ctcgaaaccc ttgatttcac tgcacttcct gatatcttga acggtacttt ggccggttac     660
tctaccactc ccaacatttt ggaccctgag actgttcaac gtgttgattc ctatactggt     720
tacattgctc cttacactag ccgtaacaac ctcaatgttt tggccaacca taccgtctcc     780
cgcattcaat tgctcccaa gaatggtagc gaacctctca aggctaccgg tgttgaatgg     840
tatcccactg gcaacaagaa tcaaaagcaa attatcaagg cccgttatga agttatcatc     900
tcatctggtg ccattggtag tcctaagctt ttggaaatct ctggtatcgg taataaggat     960
atcgtctctg ctgctggtgt cgagtccttg attgacttgc ctggcgttgg ttccaacatg    1020
caagatcacg ttcatgctat cactgtctct actaccaata ttactggcta tactaccaac    1080
agcgtctttg tcaatgaaac ccttgcccaa gaacaaagag aagaatatga agccaacaag    1140
actggtatct gggctactac tcccaacaac ctcggttatc ctacgcccga caactcttc    1200 aatggcaccg aattcgtttc tggaaaggag tttgctgaca agattcgtaa ctctactgat    1260
gaatgggcca actattatgc ttccaccaac gcctccaatg tcgagttatt aaagaagcaa    1320
tatgctattg tcgcctctcg ttacgaagag aactacttgt ctcctattga aatcaacttc    1380
actcctggtt atgagggtag cggtaatgtc gatttgcaaa acaacaagta ccaaactgtc    1440
aaccatgtct tgattgctcc tttaagtcgt ggttatactc acattaactc ttctgatgtg    1500
```

```
gaggatcatt ctgtcattaa tccccaatac tactctcatc ctatggatat tgatgtccat   1560
atcgcttcca ctaaacttgc tcgcgaaatc atcactgcct ctcccggtct tggtgacatt   1620
aacagtggcg aaatcgaacc cggtatgaat attacttctg aagacgacct tagatcttgg   1680
ttgagtaata atgtccgttc tgactggcat cctgttggta cttgtgctat gcttcccaag   1740
gaattaggtg gtgttgtcag ccccgctctc atggtttacg gcacttccaa cttgcgtgtt   1800
gttgatgctt cgattatgcc cctcgaagtc tcttctcatt tgatgcaacc cacctacggt   1860
attgctgaga aggctgctga cattattaag aatttctaca agactcaaca caagaaccaa   1920
aattag                                                              1926
```

<210> SEQ ID NO 3
<211> LENGTH: 635
<212> TYPE: PRT
<213> ORGANISM: Mucor hiemalis

<400> SEQUENCE: 3

```
Met Lys Ile Ser Val Ala Ile Val Thr Ile Ala Ala Ala Phe Ala Ser
1               5                   10                  15

Phe Ala Asn Ala Gln Lys Thr Ala Thr Ser Asn Thr Tyr Asp Tyr Val
            20                  25                  30

Ile Val Gly Gly Gly Val Gly Gly Leu Ala Leu Ala Ser Arg Leu Ser
        35                  40                  45

Glu Asp Lys Ser Val Thr Val Ala Val Leu Glu Ala Gly Pro Asn Ala
    50                  55                  60

Asp Glu Gln Phe Val Val Tyr Ala Pro Gly Met Tyr Gly Gln Ala Val
65                  70                  75                  80

Gly Thr Asp Leu Cys Pro Leu Arg Pro Thr Val Pro Gln Glu Ala Met
                85                  90                  95

Asn Asn Arg Thr Leu Thr Ile Ala Thr Gly Lys Leu Leu Gly Gly Gly
            100                 105                 110

Ser Ala Ile Asn Gly Leu Val Trp Thr Arg Gly Ala Leu Lys Asp Phe
        115                 120                 125

Asp Ala Trp Glu Glu Leu Gly Asn Pro Gly Trp Asn Gly Arg Thr Met
    130                 135                 140

Phe Lys Tyr Phe Lys Lys Val Glu Arg Phe His Pro Pro Thr Lys Ala
145                 150                 155                 160

Gln Val Gln Tyr Gly Ala Thr Tyr Gln Lys Gly Val His Gly Lys Asn
                165                 170                 175

Gly Arg Ile Asp Ile Ser Phe Pro Glu Phe Gln Phe Pro Gln Ser Ala
            180                 185                 190

Asn Trp Asn Ala Ser Leu Ala Thr Leu Asp Phe Thr His Gln Gln Asp
        195                 200                 205

Leu Leu Asn Gly Ser Leu His Gly Tyr Ser Thr Thr Pro Asn Thr Leu
    210                 215                 220

Asp Pro Lys Thr Ala Arg Arg Val Asp Ser Tyr Thr Gly Tyr Ile Ala
225                 230                 235                 240

Pro Phe Val Ser Arg Lys Asn Leu Phe Val Leu Ala Asn His Thr Val
                245                 250                 255

Ser Arg Ile Gln Phe Lys Pro Lys Asn Gly Thr Glu Leu Leu Lys Ala
            260                 265                 270

Val Gly Val Glu Trp Tyr Thr Thr Gly Asp Asn Ser Asn Lys Gln Thr
        275                 280                 285
```

```
Ile Lys Ala Arg Arg Glu Val Ile Val Ser Ser Ser Ile Gly Ser
290                 295                 300

Pro Lys Leu Leu Glu Ile Ser Gly Ile Gly Asn Lys Asp Ile Val Thr
305                 310                 315                 320

Ala Ala Gly Val Gln Ser Leu Ile Asp Leu Pro Gly Val Gly Ser Asn
                325                 330                 335

Met Gln Asp His Val His Ala Val Thr Val Ser Thr Asn Ile Thr
                340                 345                 350

Gly Phe Thr Thr Asp Ser Val Phe Gln Asn Glu Thr Leu Ala Glu Glu
                355                 360                 365

Gln Arg Gln Gln Tyr Tyr Asn Asn Lys Thr Gly Ile Trp Thr Thr Thr
370                 375                 380

Pro Asn Asn Leu Gly Tyr Pro Ser Pro Ser Gln Leu Phe Asp Gly Thr
385                 390                 395                 400

Ser Phe Glu Ser Gly Gln Ala Phe Ala Asn Arg Ile Arg Asn Ser Thr
                405                 410                 415

Asp Gln Trp Ala Glu Tyr Tyr Ala Ser Thr Asn Ala Thr Asn Ile Glu
                420                 425                 430

Leu Leu Lys Lys Gln Tyr Ala Ile Val Ala Ser Arg Tyr Glu Glu Asn
                435                 440                 445

Tyr Leu Ser Pro Ile Glu Ile Asn Phe Thr Pro Gly Tyr Gly Gly Thr
450                 455                 460

Thr Asp Val Asp Leu Lys Asn Asn Lys Tyr Gln Thr Val Asn His Val
465                 470                 475                 480

Leu Ile Ala Pro Leu Ser Arg Gly Tyr Thr His Ile Asn Ser Ser Asn
                485                 490                 495

Ile Glu Asp Pro Val Val Ile Asn Pro Gln Tyr Tyr Thr His Pro Met
                500                 505                 510

Asp Val Asp Val His Ile Ala Ser Thr Lys Leu Ala Arg Arg Ile Leu
                515                 520                 525

Gly Ala Glu Pro Gly Leu Ala Ser Ile Asn Ser Gly Glu Ile Gln Pro
530                 535                 540

Gly Ser Asn Ile Thr Ser Asp Glu Asp Val Lys Gln Trp Leu Ala Asp
545                 550                 555                 560

Asn Val Arg Ser Asp Trp His Pro Val Gly Thr Cys Ala Met Leu Pro
                565                 570                 575

Arg Glu Leu Gly Gly Val Val Asp Pro Asn Leu Leu Val Tyr Gly Thr
                580                 585                 590

Ala Asn Leu Arg Val Val Asp Ala Ser Ile Met Pro Leu Glu Ile Ser
                595                 600                 605

Ser His Leu Met Gln Pro Thr Tyr Gly Val Ala Glu Lys Ala Ala Asp
610                 615                 620

Ile Ile Lys Met Ser Arg Lys Asn Asn Asn
625                 630                 635

<210> SEQ ID NO 4
<211> LENGTH: 631
<212> TYPE: PRT
<213> ORGANISM: Mucor DR056860

<400> SEQUENCE: 4

Met Arg Leu Ser Val Ala Ile Leu Thr Leu Thr Ser Ala Leu Ala Ser
1               5                   10                  15

Val Thr Ser Ala Gln Gln Asn Asn Thr Asp Thr Tyr Asp Tyr Val Ile
                20                  25                  30
```

```
Val Gly Gly Gly Val Gly Leu Ala Leu Ala Ser Arg Leu Ser Glu
        35                  40                  45

Asp Lys Asn Val Thr Val Ala Val Leu Glu Ser Gly Pro Tyr Ala Asp
    50                  55                  60

Asp Lys Phe Val Val Tyr Ala Pro Gly Met Tyr Gly Gln Ala Val Gly
65                  70                  75                  80

Thr Asp Leu Cys Pro Leu Leu Pro Thr Val Pro Gln Pro Ser Met Asn
                85                  90                  95

Asn Arg Thr Ile Thr Ile Ala Thr Gly Arg Leu Leu Gly Gly Gly Ser
                100                 105                 110

Ala Val Asn Gly Leu Val Trp Thr Arg Gly Ala Met Lys Asp Phe Asp
            115                 120                 125

Ala Trp Gln Glu Leu Gly Asn Pro Gly Trp Asn Gly Thr Thr Met Phe
        130                 135                 140

Lys Tyr Phe Lys Lys Ile Glu Asn Phe His Pro Pro Thr Glu Glu Gln
145                 150                 155                 160

Ile Gln Tyr Gly Ala Thr Tyr Asn Lys Ser Val His Gly Phe Asn Gly
                165                 170                 175

Pro Ile Asp Ile Ala Phe Pro Val Phe Glu Phe Pro Gln Ser Ala Asn
            180                 185                 190

Trp Asn Ala Ser Leu Ala His Leu Asn Phe Thr Arg Arg Gln Asp Leu
        195                 200                 205

Leu Asp Gly Ser Leu His Gly Tyr Ser Thr Thr Pro Asn Thr Leu Asn
210                 215                 220

Pro Gln Thr Ala Arg Arg Ala Asp Ala Tyr Gly Tyr Ile Gln Pro
225                 230                 235                 240

Asn Val Asn Arg Thr Asn Leu Ala Val Leu Ala Asn His Thr Val Ser
                245                 250                 255

Arg Ile Gln Phe Glu Ala Arg Asn Gly Ser Gln Pro Leu Lys Ala Ile
            260                 265                 270

Gly Val Glu Trp Tyr Thr Thr Gly Gly Asp Lys Thr Ser Lys Gln Thr
        275                 280                 285

Ile Lys Ala Arg Arg Glu Ile Ile Leu Ser Ser Gly Ala Ile Gly Ser
    290                 295                 300

Pro Lys Leu Leu Glu Val Ser Gly Ile Gly Asn Lys Ala Ile Val Thr
305                 310                 315                 320

Ala Ala Gly Val Gln Ser Leu Ile Asp Leu Pro Gly Val Gly Ser Asn
                325                 330                 335

Met Gln Asp His Val His Ala Val Thr Val Ser Thr Thr Asn Ile Asp
            340                 345                 350

Gly Tyr Thr Thr Asn Ser Val Phe Thr Asn Glu Thr Leu Ala Gln Glu
        355                 360                 365

Gln Lys Asp Leu Tyr Tyr Asn Asn Lys Thr Gly Ile Trp Thr Thr Thr
    370                 375                 380

Pro Asn Asn Leu Gly Tyr Pro Ser Pro Ser Gln Leu Phe Thr Asn Thr
385                 390                 395                 400

Thr Phe Lys Ser Gly Lys Glu Phe Ala Ala Met Ile Arg Asn Ser Thr
                405                 410                 415

Asp Lys Tyr Ala Gln Tyr Tyr Ala Ala Asn Asn Ala Thr Asn Val Glu
            420                 425                 430

Leu Leu Lys Lys Gln Tyr Ser Ile Val Ala Arg Arg Tyr Glu Glu Asn
        435                 440                 445
```

-continued

```
Tyr Ile Ser Pro Ile Glu Ile Asn Phe Thr Pro Gly Tyr Gly Gly Thr
    450                 455                 460

Gly Met Ala Asp Leu Gln Asn Lys Lys Tyr Gln Thr Val Asn His Val
465                 470                 475                 480

Leu Val Ala Pro Leu Ser Arg Gly Tyr Thr His Ile Asn Ser Ser Asp
                485                 490                 495

Ile Glu Asp Pro Val Val Ile Asp Pro Gln Tyr Tyr Ser His Pro Leu
            500                 505                 510

Asp Val Asp Val His Val Ala Ser Thr Gln Leu Ala Arg Ser Ile Leu
        515                 520                 525

Asn Ala Pro Gly Leu Ala Ser Ile Asn Ser Gly Glu Val Glu Pro Gly
    530                 535                 540

Glu Lys Val Gln Ser Asp Glu Asp Val Arg Lys Trp Leu Ser Asp Asn
545                 550                 555                 560

Val Arg Ser Asp Trp His Pro Val Gly Thr Cys Ala Met Leu Pro Arg
                565                 570                 575

Lys Leu Gly Gly Val Val Asp Ser Lys Leu Lys Val Tyr Gly Thr Ala
            580                 585                 590

Asn Leu Arg Ile Val Asp Ala Ser Ile Ile Pro Leu Glu Ile Ser Ser
        595                 600                 605

His Leu Met Gln Pro Val Tyr Ala Val Ser Glu Arg Ala Ala Asp Ile
    610                 615                 620

Ile Lys Ser Ser Ser Lys Lys
625                 630

<210> SEQ ID NO 5
<211> LENGTH: 633
<212> TYPE: PRT
<213> ORGANISM: Mucor subtilissimus

<400> SEQUENCE: 5

Met Arg Leu Ser Leu Ala Ile Leu Ser Leu Thr Ser Ala Leu Val Thr
1               5                   10                  15

Val Thr Ser Ala Gln Gln Asn Gly Thr Ser Asn Asp Thr Tyr Asp Tyr
                20                  25                  30

Val Ile Val Gly Gly Gly Val Gly Gly Leu Ser Leu Ala Ser Arg Leu
            35                  40                  45

Ser Glu Asp Lys Gly Val Thr Val Ala Val Leu Glu Ser Gly Pro Tyr
        50                  55                  60

Ala Asp Asp Arg Phe Val Val Tyr Ala Pro Gly Met Tyr Gly Gln Ala
65                  70                  75                  80

Val Gly Thr Glu Leu Cys Pro Leu Leu Pro Thr Val Pro Gln Val Gly
                85                  90                  95

Met Asn Asn Arg Thr Ile Thr Ile Ala Thr Gly Arg Leu Leu Gly Gly
            100                 105                 110

Gly Ser Ala Val Asn Gly Leu Val Trp Thr Arg Gly Ala Met Lys Asp
        115                 120                 125

Phe Asp Ala Trp Glu Glu Leu Gly Asn Pro Gly Trp Asn Gly Lys Thr
130                 135                 140

Met Phe Lys Tyr Phe Lys Lys Ile Glu Asn Phe His Pro Pro Thr Glu
145                 150                 155                 160

Glu Gln Val Gln Tyr Gly Ala Thr Tyr Gln Lys Asn Val His Gly Ser
                165                 170                 175

Gly Gly Pro Ile Asp Ile Ser Phe Pro Val Phe Glu Phe Pro Gln Ser
            180                 185                 190
```

```
Ala Asn Trp Asn Ala Ser Leu Ala Tyr Leu Asn Phe Thr His Gln Gln
        195                 200                 205

Asp Leu Leu Asn Gly Ser Leu His Gly Tyr Ser Thr Thr Pro Asn Thr
    210                 215                 220

Leu Asn Pro Glu Thr Ala Arg Arg Ala Asp Ala Tyr Ala Gly Tyr Ile
225                 230                 235                 240

Gln Pro Asn Val Asn Arg Thr Asn Leu Ala Val Leu Ala Asn His Thr
                245                 250                 255

Val Ser Arg Ile Gln Phe Glu Lys Ser Asn Gly Ser Gln Pro Leu Lys
            260                 265                 270

Ala Ile Gly Val Glu Trp Tyr Thr Thr Gly Gly Asp Lys Ser Thr Lys
        275                 280                 285

Gln Thr Ile Lys Ala Arg Arg Glu Val Ile Ile Ser Ser Gly Ala Ile
    290                 295                 300

Gly Ser Pro Lys Leu Leu Glu Val Ser Gly Ile Gly Asn Lys Gln Ile
305                 310                 315                 320

Val Thr Ala Ala Gly Val Glu Ser Leu Ile Asp Leu Pro Gly Val Gly
                325                 330                 335

Ser Asn Met Gln Asp His Val His Ala Val Thr Val Ser Thr Thr Asn
            340                 345                 350

Ile Glu Gly Tyr Thr Thr Asn Ser Val Phe Thr Asn Glu Thr Leu Ala
        355                 360                 365

Gln Glu Gln Lys Asp Leu Tyr Tyr Asn Asn Lys Thr Gly Ile Trp Thr
    370                 375                 380

Thr Thr Pro Asn Asn Leu Gly Tyr Pro Ser Pro Ser Gln Leu Phe Thr
385                 390                 395                 400

Asn Thr Thr Phe Arg Ser Gly Lys Gln Phe Ala Ala Met Ile Arg Asn
                405                 410                 415

Ser Thr Asp Lys Tyr Ala Gln Tyr Tyr Ala Ser Thr Lys Asn Ala Thr
            420                 425                 430

Asn Ile Gln Leu Leu Lys Lys Gln Tyr Ala Ile Val Ala Arg Arg Tyr
        435                 440                 445

Glu Glu Asp Tyr Ile Ser Pro Ile Glu Ile Asn Phe Thr Pro Gly Tyr
    450                 455                 460

Gly Gly Thr Gly Glu Val Asp Leu Gln Asn Asn Lys Tyr Gln Thr Val
465                 470                 475                 480

Asn His Val Leu Val Ala Pro Leu Ser Arg Gly Tyr Thr His Ile Asn
                485                 490                 495

Ser Ser Asp Ile Glu Asp Pro Val Val Ile Asp Pro Gln Tyr Tyr Ser
            500                 505                 510

His Pro Leu Asp Val Asp Val His Val Ala Ser Thr Gln Leu Ala Arg
        515                 520                 525

Ser Ile Leu Asn Ala Pro Ala Leu Ala Ala Ile Asn Ser Gly Glu Val
    530                 535                 540

Glu Pro Gly Glu Lys Ile Gln Thr Asp Gln Asp Val Arg Lys Trp Leu
545                 550                 555                 560

Ser Asp Asn Val Arg Ser Asp Trp His Pro Val Gly Thr Cys Ala Met
                565                 570                 575

Leu Pro Lys Gly Leu Gly Gly Val Val Asp Ser Asn Leu Lys Val Tyr
            580                 585                 590

Gly Thr Ala Asn Leu Arg Val Val Asp Ala Ser Ile Ile Pro Leu Glu
        595                 600                 605
```

```
Ile Ser Ser His Leu Met Gln Pro Val Tyr Ala Val Ser Glu Arg Ala
        610                 615                 620

Ala Asp Ile Ile Lys Gly Ser Arg Asn
625                 630
```

<210> SEQ ID NO 6
<211> LENGTH: 633
<212> TYPE: PRT
<213> ORGANISM: Mucor guilliermondii

<400> SEQUENCE: 6

```
Met Lys Ile Ser Ala Ala Ile Val Thr Ile Ala Thr Ala Phe Ala Ser
1               5                   10                  15

Leu Val Ser Ala Gln Ser Asn Thr Asp Thr Tyr Asp Tyr Val Ile Val
            20                  25                  30

Gly Gly Gly Val Gly Gly Leu Ala Leu Ala Asn Arg Leu Ser Glu Asn
        35                  40                  45

Lys Gln Val Thr Val Ala Val Leu Glu Ala Gly Pro Asn Ala Asn Asp
50                  55                  60

Glu Phe Ile Val Tyr Ala Pro Gly Met Tyr Gly Gln Ala Val Gly Thr
65                  70                  75                  80

Tyr Leu Ala Pro Leu Arg Pro Thr Val Pro Gln Glu Asn Met Asn Asn
                85                  90                  95

Arg Ser Leu Ser Ile Ala Thr Gly Lys Leu Leu Gly Gly Gly Ser Ala
            100                 105                 110

Val Asn Gly Leu Val Trp Thr Arg Gly Ala Thr Lys Asp Phe Asp Ala
        115                 120                 125

Trp Glu Glu Leu Gly Asn Pro Gly Trp Asn Gly Ala Ser Met Phe Lys
130                 135                 140

Tyr Phe Lys Lys Val Glu Asn Phe Thr Ala Pro Thr Pro Tyr Gln Val
145                 150                 155                 160

Asn Tyr Gly Ala Thr Tyr Gln Lys Asn Thr His Gly Tyr Lys Gly Pro
                165                 170                 175

Val Gln Val Ser Phe Thr Asn Tyr Glu Phe Pro Gln Ser Ala His Trp
            180                 185                 190

Asn Gln Ser Leu Ala Ser Leu Gly Phe Asp His Leu Pro Asp Leu Leu
        195                 200                 205

Asn Gly Thr Leu Ser Gly Tyr Ser Thr Thr Pro Asn Ile Leu Asp Pro
210                 215                 220

Asn Thr Asp Gln Arg Cys Asp Ala Tyr Ala Ala Tyr Ile Ala Pro Tyr
225                 230                 235                 240

Thr Ala Arg Thr Asn Leu His Val Leu Ala Asn His Thr Val Ser Arg
                245                 250                 255

Ile Glu Phe Asn Gln Thr Asn Ala Asn Pro Leu Val Ala Ser Gly
            260                 265                 270

Val Glu Trp Tyr Pro Thr Gly Asp Asn Thr Lys Lys Gln Thr Ile Lys
        275                 280                 285

Ala Arg Leu Glu Val Ile Val Ser Gly Ser Ile Gly Ser Pro Lys
290                 295                 300

Leu Leu Glu Ile Ser Gly Ile Gly Asn Lys Asp Ile Thr Ala Ala
305                 310                 315                 320

Gly Val Lys Ser Leu Leu Asp Leu Pro Gly Val Gly Ser Asn Met Gln
                325                 330                 335

Asp His Val His Ala Val Thr Val Ser Thr Thr Asn Ile Thr Gly Tyr
            340                 345                 350
```

-continued

Thr Thr Asp Ser Val Phe Val Asn Ser Thr Leu Ala Ser Glu Gln Arg
            355                 360                 365

Glu Gln Tyr Glu Lys Asp Lys Ser Gly Ile Trp Thr Thr Pro Asn
    370                 375                 380

Asn Leu Gly Tyr Pro Thr Pro Ala Gln Leu Phe Asn Gly Thr Glu Phe
385                 390                 395                 400

Met Asp Gly Lys Ala Phe Ala Ala Arg Ile Arg Asn Ser Ser Gln Glu
                405                 410                 415

Trp Ala Gln Tyr Tyr Ala Ser Lys Asn Ala Ser Thr Val Glu Leu Leu
            420                 425                 430

Met Lys Gln Tyr Glu Ile Val Ala Ser Arg Tyr Glu Asn Tyr Leu
        435                 440                 445

Ser Pro Ile Glu Ile Asn Leu Thr Pro Gly Tyr Gly Gly Val Gly Thr
        450                 455                 460

Val Asp Lys Thr Lys Asn Lys Tyr Gln Thr Val Asn His Val Leu Ile
465                 470                 475                 480

Ala Pro Leu Ser Arg Gly Phe Thr His Ile Asn Ser Ser Asp Ile Glu
                485                 490                 495

Asp Pro Val Asn Ile Asn Pro Gln Tyr Tyr Ser His Pro Met Asp Ile
            500                 505                 510

Asp Val His Val Ala Ser Thr Lys Leu Ala Arg Arg Ile Ile Asn Ala
        515                 520                 525

Pro Gly Leu Gly Asp Leu Asn Ser Gly Glu Val Glu Pro Gly Met Asp
        530                 535                 540

Ile Thr Ser Asp Ser Asp Val Arg Ala Trp Leu Ala Asn Asn Val Arg
545                 550                 555                 560

Ser Asp Trp His Pro Val Gly Thr Cys Ala Met Leu Pro Lys Glu Leu
                565                 570                 575

Gly Gly Val Val Asp Ser Ser Leu Lys Val Tyr Gly Thr Ala Asn Leu
            580                 585                 590

Arg Val Val Asp Ala Ser Ile Met Pro Leu Glu Val Ser Ser His Leu
        595                 600                 605

Met Gln Pro Thr Phe Gly Val Ala Glu Lys Ala Ala Asp Ile Ile Lys
    610                 615                 620

Ala Glu Tyr Lys Lys Gln Lys Ala Gln
625                 630

<210> SEQ ID NO 7
<211> LENGTH: 637
<212> TYPE: PRT
<213> ORGANISM: Circinella simplex

<400> SEQUENCE: 7

Met Lys Ile Ser Ala Ala Val Val Thr Ile Val Thr Ala Phe Ala Ser
1               5                   10                  15

Val Ala Thr Ala Gln Gln Gln Asn Thr Ser Glu Thr Asn Thr Tyr Asp
            20                  25                  30

Tyr Val Ile Val Gly Gly Gly Val Gly Gly Leu Ala Leu Ala Ser Arg
        35                  40                  45

Leu Ser Glu Asn Lys Gly Val Ser Val Ala Val Leu Glu Ala Gly Pro
    50                  55                  60

Tyr Ala Gly Asp Gln Phe Val Val Tyr Ala Pro Gly Met Tyr Gly Gln
65                  70                  75                  80

Ala Val Gly Thr Asp Leu Cys Pro Leu Leu Pro Thr Thr Pro Gln Glu

```
                      85                  90                  95
Asn Met Gly Asn Arg Ser Leu Ser Ile Ala Thr Gly Lys Leu Leu Gly
            100                 105                 110

Gly Gly Ser Ser Val Asn Gly Leu Val Trp Thr Arg Gly Gly Leu Lys
            115                 120                 125

Asp Phe Asp Ala Trp Glu Glu Leu Gly Asn Pro Gly Trp Asn Gly Ala
130                 135                 140

Ser Met Phe Asn Tyr Phe Lys Lys Val Glu Asn Phe Thr Pro Pro Thr
145                 150                 155                 160

Pro Ala Gln Ala Ala Tyr Gly Ala Thr Tyr Gln Lys Asn Ala His Gly
                165                 170                 175

Thr Lys Gly Pro Met Asp Val Ser Phe Thr Asn Phe Glu Phe Pro Gln
            180                 185                 190

Ser Gly Asn Trp Asn Ala Ser Leu Asn Ala Val Gly Phe Thr Ala Val
            195                 200                 205

Pro Asp Leu Leu Asn Gly Thr Leu His Gly Tyr Ser Thr Thr Pro Asn
210                 215                 220

Ile Leu Asp Pro Val Asn Ala Arg Arg Ala Asp Ala Tyr Ala Gly Tyr
225                 230                 235                 240

Ile Lys Pro Tyr Ile Ser Arg Asn Asn Leu Ala Val Leu Ala Asn His
                245                 250                 255

Thr Val Ser Arg Ile Gln Phe Ala Pro Gln Ser Gly Ser Gln Pro Leu
            260                 265                 270

Arg Ala Thr Gly Val Glu Trp Tyr Pro Thr Gly Asp Lys Ser Gln Lys
            275                 280                 285

Gln Val Leu Asn Ala Arg Tyr Glu Val Ile Leu Ser Ser Gly Ala Ile
            290                 295                 300

Gly Ser Pro Lys Leu Leu Glu Leu Ser Gly Ile Gly Asn Lys Asp Ile
305                 310                 315                 320

Val Ala Ala Ala Gly Ile Gln Ser Leu Leu Asp Leu Pro Gly Val Gly
                325                 330                 335

Ser Asn Met Gln Asp His Val His Ala Val Thr Val Ser Thr Thr Asn
            340                 345                 350

Ile Thr Gly Tyr Thr Thr Asn Ser Ile Phe Thr Asn Asp Ala Leu Ala
            355                 360                 365

Ala Glu Glu Arg Gln Glu Tyr Asp Asn Asn Lys Thr Gly Ile Tyr Thr
            370                 375                 380

Thr Thr Pro Asn Asn Leu Gly Tyr Pro Ser Pro Ser Gln Leu Phe Arg
385                 390                 395                 400

Gly Thr Ser Phe Val Ser Gly Lys Gln Phe Ala Ala Arg Ile Arg Asn
                405                 410                 415

Thr Thr Asp Glu Trp Ala Glu Arg Tyr Ala Ala Asp Asn Ala Thr Asn
            420                 425                 430

Ala Glu Leu Leu Lys Lys Gln Tyr Ala Ile Ile Ala Ser Arg Tyr Glu
            435                 440                 445

Glu Asp Tyr Leu Ser Pro Ile Glu Ile Asn Leu Thr Pro Gly Tyr Gly
            450                 455                 460

Gly Thr Ala Asp Val Asp Leu Thr Asn Asn Lys Tyr Gln Thr Val Asn
465                 470                 475                 480

His Val Leu Ile Ala Pro Leu Ser Arg Gly Tyr Thr His Ile Lys Ser
                485                 490                 495

Ala Asp Ile Glu Asp Ala Val Asp Ile Asn Pro Gln Tyr Tyr Ser His
            500                 505                 510
```

```
Pro Met Asp Val Asp Val His Val Ala Ser Thr Lys Leu Ala Arg Glu
        515                 520                 525

Ile Ile Ser Ala Ser Pro Gly Leu Gly Asp Ile Asn Ser Gly Glu Thr
530                 535                 540

Glu Pro Gly Lys Glu Ile Thr Ser Asp Ser Asp Val Arg Lys Trp Leu
545                 550                 555                 560

Ala Asp Asn Val Arg Ser Asp Trp His Pro Val Gly Thr Cys Ala Met
                565                 570                 575

Leu Pro Lys Glu Leu Gly Gly Val Val Asp Pro Asn Leu Lys Val Tyr
                580                 585                 590

Gly Thr Ser Asn Leu Arg Val Val Asp Ala Ser Val Met Pro Leu Glu
            595                 600                 605

Val Ser Ser His Leu Met Gln Pro Thr Phe Gly Ile Ala Glu Lys Ala
610                 615                 620

Ala Asp Ile Ile Lys Ser Ala Asn Lys Lys Arg Ser Asn
625                 630                 635
```

<210> SEQ ID NO 8
<211> LENGTH: 637
<212> TYPE: PRT
<213> ORGANISM: Circinella

<400> SEQUENCE: 8

```
Met Lys Ile Ser Ala Ala Val Val Thr Ile Val Thr Ala Phe Ala Ser
1               5                   10                  15

Val Ala Thr Ala Gln Gln Gln Asn Thr Ser Glu Thr Asn Thr Tyr Asp
            20                  25                  30

Tyr Val Ile Val Gly Gly Gly Val Gly Gly Leu Ala Leu Ala Ser Arg
        35                  40                  45

Leu Ser Glu Asn Lys Gly Val Ser Val Ala Val Leu Glu Ala Gly Pro
50                  55                  60

Tyr Ala Gly Asp Gln Phe Val Val Tyr Ala Pro Gly Met Tyr Gly Gln
65                  70                  75                  80

Ala Val Gly Thr Asp Leu Cys Pro Leu Leu Pro Thr Thr Pro Gln Glu
            85                  90                  95

Asn Met Gly Asn Arg Ser Leu Ser Ile Ala Thr Gly Lys Leu Leu Gly
            100                 105                 110

Gly Gly Ser Ser Val Asn Gly Leu Val Trp Thr Arg Gly Gly Leu Lys
        115                 120                 125

Asp Phe Asp Ala Trp Glu Glu Leu Gly Asn Pro Gly Trp Asn Gly Ala
130                 135                 140

Ser Met Phe Asn Tyr Phe Lys Lys Val Glu Asn Phe Thr Pro Pro Thr
145                 150                 155                 160

Pro Ala Gln Ala Ala Tyr Gly Ala Thr Tyr Gln Lys Asn Ala His Gly
                165                 170                 175

Thr Lys Gly Pro Met Asp Val Ser Phe Thr Asn Phe Glu Phe Pro Gln
            180                 185                 190

Ser Gly Asn Trp Asn Ala Ser Leu Asn Ala Val Gly Phe Thr Ala Val
        195                 200                 205

Pro Asp Leu Leu Asn Gly Thr Leu His Gly Tyr Ser Thr Thr Pro Asn
210                 215                 220

Ile Leu Asp Pro Val Asn Ala Arg Arg Ala Asp Ala Tyr Ala Gly Tyr
225                 230                 235                 240

Ile Lys Pro Tyr Ile Ser Arg Asn Asn Leu Ala Val Leu Ala Asn His
```

245                 250                 255
    Thr Val Ser Arg Ile Gln Phe Ala Pro Gln Ser Gly Ser Gln Pro Leu
                    260                 265                 270

Arg Ala Thr Gly Val Glu Trp Tyr Pro Thr Gly Asp Lys Ser Gln Lys
                275                 280                 285

Gln Val Leu Asn Ala Arg Tyr Glu Val Ile Leu Ser Ser Gly Ala Ile
            290                 295                 300

Gly Ser Pro Lys Leu Leu Glu Leu Ser Gly Ile Gly Asn Lys Asp Ile
    305                 310                 315                 320

Val Ala Ala Ala Gly Ile Gln Ser Leu Leu Asp Leu Pro Gly Val Gly
                    325                 330                 335

Ser Asn Met Gln Asp His Val His Ala Val Thr Val Ser Thr Thr Asn
                340                 345                 350

Ile Thr Gly Tyr Thr Thr Asn Ser Ile Phe Thr Asn Asp Ala Leu Ala
                355                 360                 365

Ala Glu Glu Arg Gln Glu Tyr Asp Asn Asn Lys Thr Gly Ile Tyr Thr
            370                 375                 380

Thr Thr Pro Asn Asn Leu Gly Tyr Pro Ser Pro Ser Gln Leu Phe Arg
    385                 390                 395                 400

Gly Thr Ser Phe Val Ser Gly Lys Gln Phe Ala Ala Arg Ile Arg Asn
                    405                 410                 415

Thr Thr Asp Glu Trp Ala Glu Arg Tyr Ala Ala Asp Asn Ala Thr Asn
                420                 425                 430

Ala Glu Leu Leu Lys Lys Gln Tyr Ala Ile Ile Ala Ser Arg Tyr Glu
                435                 440                 445

Glu Asp Tyr Leu Ser Pro Ile Glu Ile Asn Leu Thr Pro Gly Tyr Gly
            450                 455                 460

Gly Thr Ala Asp Val Asp Leu Thr Asn Asn Lys Tyr Gln Thr Val Asn
    465                 470                 475                 480

His Val Leu Ile Ala Pro Leu Ser Arg Gly Tyr Thr His Ile Lys Ser
                    485                 490                 495

Ala Asp Ile Glu Asp Ala Val Asp Ile Asn Pro Gln Tyr Tyr Ser His
                500                 505                 510

Pro Met Asp Val Asp Val His Val Ala Ser Thr Lys Leu Ala Arg Glu
                515                 520                 525

Ile Ile Ser Ala Ser Pro Gly Leu Gly Asp Ile Asn Ser Gly Glu Thr
            530                 535                 540

Glu Pro Gly Lys Glu Ile Thr Ser Asp Ser Asp Val Arg Lys Trp Leu
    545                 550                 555                 560

Ala Asp Asn Val Arg Ser Asp Trp His Pro Val Gly Thr Cys Ala Met
                    565                 570                 575

Leu Pro Lys Glu Leu Asp Gly Val Val Asp Pro Asn Leu Lys Val Tyr
                580                 585                 590

Gly Thr Ser Asn Leu Arg Val Val Asp Ala Ser Val Met Pro Leu Glu
                595                 600                 605

Val Ser Ser His Leu Met Gln Pro Thr Phe Gly Ile Ala Glu Lys Ala
            610                 615                 620

Ala Asp Ile Ile Lys Ser Ala Asn Lys Lys Arg Ser Asn
    625                 630                 635

<210> SEQ ID NO 9
<211> LENGTH: 644
<212> TYPE: PRT
<213> ORGANISM: Mucor circinelloides

<400> SEQUENCE: 9

Met Lys Ile Ser Ala Ala Ile Ile Thr Val Val Thr Ala Phe Ala Ser
1               5                   10                  15

Phe Ala Ser Ala Gln Gln Asp Thr Asn Asn Thr Ser Ser Thr Asp Thr
            20                  25                  30

Tyr Asp Tyr Val Ile Val Gly Gly Val Ala Gly Leu Ala Leu Ala
                35                  40                  45

Ser Arg Ile Ser Glu Asn Lys Asp Val Thr Val Ala Val Leu Glu Ser
    50                  55                  60

Gly Pro Asn Ala Glu Asp Gln Phe Val Val Tyr Ala Pro Gly Met Tyr
65                  70                  75                  80

Gly Gln Ala Val Gly Thr Glu Leu Ala Pro Leu Val Pro Thr Thr Pro
                85                  90                  95

Gln Glu Asn Met Gly Asn Arg Ser Leu Ser Ile Ala Thr Gly Arg Leu
                100                 105                 110

Leu Gly Gly Gly Ser Ala Val Asn Gly Leu Val Trp Thr Arg Gly Gly
            115                 120                 125

Leu Lys Asp Tyr Asp Ala Trp Glu Glu Leu Gly Asn Pro Gly Trp Asn
130                 135                 140

Gly Ser Asn Leu Phe Lys Tyr Phe Lys Lys Val Glu Asn Phe His Pro
145                 150                 155                 160

Pro Thr Pro Ala Gln Ile Glu Tyr Gly Ala Thr Tyr Gln Lys Ser Ala
                165                 170                 175

His Gly Lys Asn Gly Pro Ile Asp Val Ser Phe Thr Asn Phe Glu Phe
            180                 185                 190

Pro Gln Ser Ala Lys Trp Asn Ala Ser Leu Glu Ser Leu Asp Phe Thr
            195                 200                 205

Ala Leu Pro Asp Leu Leu Asn Gly Thr Leu Ala Gly Tyr Ser Thr Thr
210                 215                 220

Pro Asn Ile Leu Asp Pro Glu Thr Ala Arg Arg Val Asp Ala Tyr Ala
225                 230                 235                 240

Gly Tyr Ile Val Pro Tyr Met Gly Arg Asn Asn Leu Asn Val Leu Ala
                245                 250                 255

Asn His Thr Val Ser Arg Ile Gln Phe Ala Pro Gln Asn Gly Ser Glu
            260                 265                 270

Pro Leu Lys Ala Thr Gly Val Glu Trp Tyr Pro Thr Gly Asn Lys Asp
            275                 280                 285

Gln Lys Gln Thr Ile Lys Ala Arg Tyr Glu Val Ile Ile Ser Ser Gly
        290                 295                 300

Ala Ile Gly Ser Pro Lys Leu Leu Glu Ile Ser Gly Ile Gly Asn Lys
305                 310                 315                 320

Asp Ile Val Thr Ala Ala Gly Val Glu Ser Leu Ile Asp Leu Pro Gly
                325                 330                 335

Val Gly Ala Asn Met Gln Asp His Val His Ala Val Thr Val Ser Thr
                340                 345                 350

Thr Asn Ile Asp Gly Tyr Thr Thr Asn Ser Val Phe Thr Asn Glu Thr
            355                 360                 365

Leu Ala Gln Glu Gln Arg Glu Gln Tyr Glu Ala Asn Lys Thr Gly Ile
        370                 375                 380

Trp Thr Thr Thr Pro Asn Asn Leu Gly Tyr Pro Thr Pro Glu Gln Leu
385                 390                 395                 400

Phe Asn Gly Thr Glu Phe Val Ser Gly Lys Glu Phe Ala Ala Lys Ile

```
            405                 410                 415
Arg Asn Ser Thr Asp Glu Trp Ala Asn Tyr Tyr Ala Ser Thr Asn Ala
            420                 425                 430

Thr Asn Ala Asp Leu Leu Lys Lys Gln Tyr Ala Ile Val Ala Ser Arg
            435                 440                 445

Tyr Glu Glu Asn Tyr Leu Ser Pro Ile Glu Ile Asn Leu Thr Pro Gly
            450                 455                 460

Tyr Gly Gly Thr Gly Ser Pro Asp Leu Gln Asn Asn Lys Tyr Gln Thr
465                 470                 475                 480

Val Asn His Val Leu Ile Ala Pro Leu Ser Arg Gly Tyr Ala His Ile
            485                 490                 495

Asn Ser Ser Asp Ile Glu Glu Pro Ser Val Ile Asn Pro Gln Tyr Tyr
            500                 505                 510

Ser His Pro Leu Asp Ile Asp Val His Val Ala Ser Thr Lys Leu Ala
            515                 520                 525

Arg Glu Ile Ile Thr Ala Ser Pro Gly Leu Gly Asp Leu Asn Ser Gly
            530                 535                 540

Glu Val Glu Pro Gly Met Asn Val Thr Ser Glu Asp Leu Arg Ser
545                 550                 555                 560

Trp Leu Ser Asn Asn Val Arg Ser Asp Trp His Pro Val Gly Thr Cys
            565                 570                 575

Ala Met Leu Pro Gln Glu Leu Gly Gly Val Val Ser Pro Ala Leu Met
            580                 585                 590

Val Tyr Gly Thr Ser Asn Leu Arg Val Val Asp Ala Ser Ile Met Pro
            595                 600                 605

Leu Glu Val Ser Ser His Leu Met Gln Pro Thr Tyr Gly Ile Ala Glu
            610                 615                 620

Lys Ala Ala Asp Ile Ile Lys Asn Tyr Tyr Lys Ser Gln Tyr Ser Gly
625                 630                 635                 640

Ala Gly Lys Asn

<210> SEQ ID NO 10
<211> LENGTH: 641
<212> TYPE: PRT
<213> ORGANISM: Mucor prainii

<400> SEQUENCE: 10

Met Lys Ile Thr Ala Ala Ile Ile Thr Val Ala Thr Ala Phe Ala Ser
1               5                   10                  15

Phe Ala Ser Ala Gln Gln Asp Thr Asn Ser Ser Ser Thr Asp Thr Tyr
            20                  25                  30

Asp Tyr Val Ile Val Gly Gly Gly Val Ala Gly Leu Ala Leu Ala Ser
            35                  40                  45

Arg Ile Ser Glu Asn Lys Asp Val Thr Val Ala Val Leu Glu Ser Gly
            50                  55                  60

Pro Tyr Ala Gly Asp Arg Phe Val Val Tyr Ala Pro Gly Met Tyr Gly
65                  70                  75                  80

Gln Ala Val Gly Thr Asp Leu Ala Pro Leu Ile Pro Thr Thr Pro Gln
            85                  90                  95

Glu Asn Met Gly Asn Arg Ser Leu Thr Ile Ala Thr Gly Arg Leu Leu
            100                 105                 110

Gly Gly Gly Ser Ala Ile Asn Gly Leu Val Trp Thr Arg Gly Gly Leu
            115                 120                 125

Lys Asp Tyr Asp Ala Trp Glu Glu Leu Gly Asn Pro Gly Trp Asn Gly
```

```
                130                 135                 140
Ala Asn Leu Phe Lys Tyr Phe Lys Lys Val Glu Asn Phe Thr Pro Pro
145                 150                 155                 160

Thr Pro Ala Gln Ile Glu Tyr Gly Ala Thr Tyr Gln Lys Ser Ala His
                165                 170                 175

Gly Lys Lys Gly Pro Ile Asp Val Ser Phe Thr Asn Tyr Glu Phe Ser
                180                 185                 190

Gln Ser Ala Ser Trp Asn Ala Ser Leu Glu Thr Leu Asp Phe Thr Ala
                195                 200                 205

Leu Pro Asp Ile Leu Asn Gly Thr Leu Ala Gly Tyr Ser Thr Thr Pro
210                 215                 220

Asn Ile Leu Asp Pro Glu Thr Val Arg Arg Val Asp Ser Tyr Thr Gly
225                 230                 235                 240

Tyr Ile Ala Pro Tyr Thr Ser Arg Asn Asn Leu Asn Val Leu Ala Asn
                245                 250                 255

His Thr Val Ser Arg Ile Gln Phe Ala Pro Lys Asn Gly Ser Glu Pro
                260                 265                 270

Leu Lys Ala Thr Gly Val Glu Trp Tyr Pro Thr Gly Asn Lys Asn Gln
                275                 280                 285

Lys Gln Ile Ile Lys Ala Arg Tyr Glu Val Ile Ile Ser Ser Gly Ala
290                 295                 300

Ile Gly Ser Pro Lys Leu Leu Glu Ile Ser Gly Ile Gly Asn Lys Asp
305                 310                 315                 320

Ile Val Ser Ala Ala Gly Val Glu Ser Leu Ile Asp Leu Pro Gly Val
                325                 330                 335

Gly Ser Asn Met Gln Asp His Val His Ala Ile Thr Val Ser Thr Thr
                340                 345                 350

Asn Ile Thr Gly Tyr Thr Thr Asn Ser Val Phe Val Asn Glu Thr Leu
                355                 360                 365

Ala Gln Glu Gln Arg Glu Glu Tyr Glu Ala Asn Lys Thr Gly Ile Trp
                370                 375                 380

Ala Thr Cys Pro Asn Asn Leu Gly Tyr Pro Thr Pro Glu Gln Leu Phe
385                 390                 395                 400

Asn Gly Thr Glu Phe Val Ser Gly Lys Glu Phe Ala Asp Lys Ile Arg
                405                 410                 415

Asn Ser Thr Asp Glu Trp Ala Asn Tyr Tyr Ala Ser Thr Asn Ala Ser
                420                 425                 430

Asn Val Glu Leu Leu Lys Lys Gln Tyr Ala Ile Val Ala Ser Arg Tyr
                435                 440                 445

Glu Glu Asn Tyr Leu Ser Pro Ile Glu Ile Asn Phe Thr Pro Gly Tyr
450                 455                 460

Glu Gly Ser Gly Asn Val Asp Leu Gln Asn Asn Lys Tyr Gln Thr Val
465                 470                 475                 480

Asn His Val Leu Ile Ala Pro Leu Ser Arg Gly Tyr Thr His Ile Asn
                485                 490                 495

Ser Ser Asp Val Glu Asp His Ser Val Ile Asn Pro Gln Tyr Tyr Ser
                500                 505                 510

His Pro Met Asp Ile Asp Val His Ile Ala Ser Thr Lys Leu Ala Arg
                515                 520                 525

Glu Ile Ile Thr Ala Ser Pro Gly Leu Gly Asp Ile Asn Ser Gly Glu
                530                 535                 540

Ile Glu Pro Gly Met Asn Ile Thr Ser Asp Asp Val Arg Lys Trp
545                 550                 555                 560
```

```
Leu Ser Asn Asn Val Arg Ser Asp Trp His Pro Val Gly Thr Cys Ala
            565                 570                 575

Met Leu Pro Lys Glu Leu Gly Gly Val Val Ser Pro Ala Leu Met Val
        580                 585                 590

Tyr Gly Thr Ser Asn Leu Arg Val Val Asp Ala Ser Ile Met Pro Leu
    595                 600                 605

Glu Val Ser Ser His Leu Met Gln Pro Thr Tyr Gly Ile Ala Glu Lys
610                 615                 620

Ala Ala Asp Ile Ile Lys Asn Phe Tyr Lys Thr Gln His Lys Asn Gln
625                 630                 635                 640

Asn

<210> SEQ ID NO 11
<211> LENGTH: 1926
<212> TYPE: DNA
<213> ORGANISM: Mucor prainii

<400> SEQUENCE: 11
atgaagatca cagctgccat tatcactgtt gccacagcat ttgcttcttt tgcttctgct     60
caacaagaca caaattcttc ctcaactgat acttatgatt atgttatcgt tggcggcggt    120
gtagctggtt tggctttggc tagtcgtatc tctgaaaaca aggatgtcac tgttgctgtt    180
ctcgagtccg gtcctatgc cggtgataga tttgttgttt atgctcctgg catgtatggc    240
caagctgttg gcactgatct cgctcctctc attcctacta ctcctcaaga aaatatgggc    300
aacagaagtc tcacaatcgc tactggtaga ttgctcggtg gtggcagtgc tattaatggt    360
ctcgtttgga cccgtggtgg cttgaaggat tacgatgctt gggaggagct cggtaaccct    420
ggatggaacg tgccaacttt gttcaagtac tttaagaagg tcgaaaactt cactcctcct    480
actcctgccc aaattgaata cggcgctact tatcagaaaa gtgctcatgg caagaaggga    540
cctattgatg tctctttcac gaactacgag ttctctcaat ctgctagctg aacgcctca    600 ctcgaaaccc ttgatttcac tgcacttcct gatatcttga acggtacttt ggccggttac    660
tctaccactc ccaacatttt ggaccctgag actgttcgac gtgttgattc ctatactggt    720
tacattgctc cttacactag ccgtaacaac ctcaatgttt tggccaacca taccgtctcc    780
cgcattcaat tgctcccaa gaatggtagc gaacctctca aggctaccgg tgttgaatgg    840
tatcccactg gcaacaagaa tcaaaagcaa attatcaagg cccgttatga agttatcatc    900
tcatctggtg ccattggtag tcctaagctt ttggaaatct ctggtatcgg taataaggat    960
atcgtctctg ctgctggtgt cgagtccttg attgacttgc ctggcgttgg ttccaacatg   1020
caagatcacg ttcatgctat cactgtctct actaccaata ttactggcta tactaccaac   1080
agcgtctttg tcaatgaaac ccttgcccaa gaacaaagag aagaatatga agccaacaag   1140
actggtatct gggctacttg tcccaacaac ctcggttatc ctacgcccga caactcttc   1200 aatggcaccg aattcgtttc tggaaaggag tttgctgaca gattcgtaa ctctactgat   1260 gaatgggcca actattatgc ttccaccaac gcctccaatg tcgagttatt aaagaagcaa   1320
tatgctattg tcgcctctcg ttacgaagag aactacttgt ctcctattga atcaacttc   1380 actcctggtt atgagggtag cggtaatgtc gatttgcaaa acaacaagta ccaaactgtc   1440
aaccatgtct tgattgctcc tttaagtcgt ggttatactc acattaactc ttctgatgtg   1500
gaggatcatt ctgtcattaa tccccaatac tactctcatc ctatggatat tgatgtccat   1560
atcgcttcca ctaaacttgc tcgcgaaatc atcactgcct ctcccggtct tggtgacatt   1620
```

-continued

```
aacagtggcg aaatcgaacc cggtatgaat attacttctg acgacgacgt tagaaaatgg    1680
ttgagtaata atgtccgttc tgactggcat cctgttggta cttgtgctat gcttcccaag    1740
gaattaggtg gtgttgtcag ccccgctctc atggtttacg gcacttccaa cttgcgtgtt    1800
gttgatgctt cgattatgcc cctcgaagtc tcttctcatt tgatgcaacc cacctacggt    1860
attgctgaga aggctgctga cattattaag aatttctaca agactcaaca caagaaccaa    1920
aattag                                                               1926
```

<210> SEQ ID NO 12
<211> LENGTH: 641
<212> TYPE: PRT
<213> ORGANISM: Mucor prainii

<400> SEQUENCE: 12

```
Met Lys Ile Thr Ala Ala Ile Ile Thr Val Ala Thr Ala Phe Ala Ser
1               5                   10                  15

Phe Ala Ser Ala Gln Gln Asp Thr Asn Ser Ser Ser Thr Asp Thr Tyr
            20                  25                  30

Asp Tyr Val Ile Val Gly Gly Gly Val Ala Gly Leu Ala Leu Ala Ser
        35                  40                  45

Arg Ile Ser Glu Asn Lys Asp Val Thr Val Ala Val Leu Glu Ser Gly
    50                  55                  60

Pro Tyr Ala Gly Asp Arg Phe Val Val Tyr Ala Pro Gly Met Tyr Gly
65                  70                  75                  80

Gln Ala Val Gly Thr Asp Leu Ala Pro Leu Ile Pro Thr Thr Pro Gln
                85                  90                  95

Glu Asn Met Gly Asn Arg Ser Leu Thr Ile Ala Thr Gly Arg Leu Leu
            100                 105                 110

Gly Gly Gly Ser Ala Ile Asn Gly Leu Val Trp Thr Arg Gly Gly Leu
        115                 120                 125

Lys Asp Tyr Asp Ala Trp Glu Glu Leu Gly Asn Pro Gly Trp Asn Gly
    130                 135                 140

Ala Asn Leu Phe Lys Tyr Phe Lys Lys Val Glu Asn Phe Thr Pro Pro
145                 150                 155                 160

Thr Pro Ala Gln Ile Glu Tyr Gly Ala Thr Tyr Gln Lys Ser Ala His
                165                 170                 175

Gly Lys Lys Gly Pro Ile Asp Val Ser Phe Thr Asn Tyr Glu Phe Ser
            180                 185                 190

Gln Ser Ala Ser Trp Asn Ala Ser Leu Glu Thr Leu Asp Phe Thr Ala
        195                 200                 205

Leu Pro Asp Ile Leu Asn Gly Thr Leu Ala Gly Tyr Ser Thr Thr Pro
    210                 215                 220

Asn Ile Leu Asp Pro Glu Thr Val Arg Arg Val Asp Ser Tyr Thr Gly
225                 230                 235                 240

Tyr Ile Ala Pro Tyr Thr Ser Arg Asn Asn Leu Asn Val Leu Ala Asn
                245                 250                 255

His Thr Val Ser Arg Ile Gln Phe Ala Pro Lys Asn Gly Ser Glu Pro
            260                 265                 270

Leu Lys Ala Thr Gly Val Glu Trp Tyr Pro Thr Gly Asn Lys Asn Gln
        275                 280                 285

Lys Gln Ile Ile Lys Ala Arg Tyr Glu Val Ile Ser Ser Gly Ala
    290                 295                 300

Ile Gly Ser Pro Lys Leu Leu Glu Ile Ser Gly Ile Gly Asn Lys Asp
```

```
305             310             315             320
Ile Val Ser Ala Ala Gly Val Glu Ser Leu Ile Asp Leu Pro Gly Val
                325             330             335
Gly Ser Asn Met Gln Asp His Val His Ala Ile Thr Val Ser Thr Thr
                340             345             350
Asn Ile Thr Gly Tyr Thr Thr Asn Ser Val Phe Val Asn Glu Thr Leu
                355             360             365
Ala Gln Glu Gln Arg Glu Glu Tyr Glu Ala Asn Lys Thr Gly Ile Trp
370             375             380
Ala Thr Cys Pro Asn Asn Leu Gly Tyr Pro Thr Pro Glu Gln Leu Phe
385             390             395             400
Asn Gly Thr Glu Phe Val Ser Gly Lys Glu Phe Ala Asp Lys Ile Arg
                405             410             415
Asn Ser Thr Asp Glu Trp Ala Asn Tyr Tyr Ala Ser Thr Asn Ala Ser
                420             425             430
Asn Val Glu Leu Leu Lys Lys Gln Tyr Ala Ile Val Ala Ser Arg Tyr
                435             440             445
Glu Glu Asn Tyr Leu Ser Pro Ile Glu Ile Asn Phe Thr Pro Gly Cys
                450             455             460
Glu Gly Ser Gly Asn Cys Asp Cys Gln Asn Asn Lys Tyr Gln Thr Val
465             470             475             480
Asn His Val Leu Ile Ala Pro Leu Ser Arg Gly Tyr Thr His Ile Asn
                485             490             495
Ser Ser Asp Val Glu Asp His Ser Val Ile Asn Pro Gln Tyr Tyr Ser
                500             505             510
His Pro Met Asp Ile Asp Val His Ile Ala Ser Thr Lys Leu Ala Arg
                515             520             525
Glu Ile Ile Thr Ala Ser Pro Gly Leu Gly Asp Ile Asn Ser Gly Glu
                530             535             540
Ile Glu Pro Gly Met Asn Ile Thr Ser Asp Asp Val Arg Lys Trp
545             550             555             560
Leu Ser Asn Asn Val Arg Ser Asp Trp His Pro Val Gly Thr Cys Ala
                565             570             575
Met Leu Pro Lys Glu Leu Gly Gly Val Val Ser Pro Ala Leu Met Val
                580             585             590
Tyr Gly Thr Ser Asn Leu Arg Val Val Asp Ala Ser Ile Met Pro Leu
                595             600             605
Glu Val Ser Ser His Leu Met Gln Pro Thr Tyr Gly Ile Ala Glu Lys
                610             615             620
Ala Ala Asp Ile Ile Lys Asn Phe Tyr Lys Thr Gln His Lys Asn Gln
625             630             635             640
Asn

<210> SEQ ID NO 13
<211> LENGTH: 1926
<212> TYPE: DNA
<213> ORGANISM: Mucor prainii

<400> SEQUENCE: 13
atgaagatca cagctgccat tatcactgtt gccacagcat ttgcttcttt tgcttctgct      60
caacaagaca caaattcttc ctcaactgat acttatgatt atgttatcgt tggcggcggt     120
gtagctggtt tggctttggc tagtcgtatc tctgaaaaca aggatgtcac tgttgctgtt     180
ctcgagtccg gtccttatgc cggtgataga tttgttgttt atgctcctgg catgtatggc     240
```

```
caagctgttg gcactgatct cgctcctctc attcctacta ctcctcaaga aaatatgggc      300
aacagaagtc tcacaatcgc tactggtaga ttgctcggtg gtggcagtgc tattaatggt      360
ctcgtttgga cccgtggtgg cttgaaggat tacgatgctt gggaggagct cggtaaccct      420
ggatggaacg gtgccaactt gttcaagtac tttaagaagg tcgaaaactt cactcctcct      480
actcctgccc aaattgaata cggcgctact tatcagaaaa gtgctcatgg caagaaggga      540
cctattgatg tctctttcac gaactacgag ttctctcaat ctgctagctg gaacgcctca      600
ctcgaaaccc ttgatttcac tgcacttcct gatatcttga acggtacttt ggccggttac      660
tctaccactc ccaacatttt ggaccctgag actgttcgac gtgttgattc ctatactggt      720
tacattgctc cttacactag ccgtaacaac ctcaatgttt tggccaacca taccgtctcc      780
cgcattcaat tgctcccaa gaatggtagc gaacctctca aggctaccgg tgttgaatgg      840
tatcccactg gcaacaagaa tcaaaagcaa attatcaagg cccgttatga agttatcatc      900
tcatctggtg ccattggtag tcctaagctt ttggaaatct ctggtatcgg taataaggat      960
atcgtctctg ctgctggtgt cgagtccttg attgacttgc ctggcgttgg ttccaacatg     1020
caagatcacg ttcatgctat cactgtctct actaccaata ttactggcta tactaccaac     1080
agcgtctttg tcaatgaaac ccttgcccaa gaacaaagag aagaatatga agccaacaag     1140
actggtatct gggctacttg tcccaacaac ctcggttatc ctacgcccga caactcttc      1200 aatggcaccg aattcgtttc tggaaaggag tttgctgaca agattcgtaa ctctactgat     1260
gaatgggcca actattatgc ttccaccaac gcctccaatg tcgagttatt aaagaagcaa     1320
tatgctattg tcgcctctcg ttacgaagag aactacttgt ctcctattga aatcaacttc     1380
actcctggtt gtgagggtag cggtaattgc gattgtcaaa acaacaagta ccaaactgtc     1440
aaccatgtct tgattgctcc tttaagtcgt ggttatactc acattaactc ttctgatgtg     1500
gaggatcatt ctgtcattaa tccccaatac tactctcatc ctatggatat tgatgtccat     1560
atcgcttcca ctaaacttgc tcgcgaaatc atcactgcct ctcccggtct tggtgacatt     1620
aacagtggcg aaatcgaacc cggtatgaat attacttctg acgacgacgt tagaaaatgg     1680
ttgagtaata atgtccgttc tgactggcat cctgttggta cttgtgctat gcttcccaag     1740
gaattaggtg tgttgtcag ccccgctctc atggtttacg gcacttccaa cttgcgtgtt     1800
gttgatgctt cgattatgcc cctcgaagtc tcttctcatt tgatgcaacc cacctacggt     1860
attgctgaga aggctgctga cattattaag aatttctaca agactcaaca caagaaccaa     1920
aattag                                                                1926
```

<210> SEQ ID NO 14
<211> LENGTH: 9
<212> TYPE: PRT
<213> ORGANISM: Artificial
<220> FEATURE:
<223> OTHER INFORMATION: FeS binding motif
<220> FEATURE:
<221> NAME/KEY: MISC_FEATURE
<222> LOCATION: (2)..(6)
<223> OTHER INFORMATION: Xaa is any naturally occurring amino acid
<220> FEATURE:
<221> NAME/KEY: MISC_FEATURE
<222> LOCATION: (8)..(8)
<223> OTHER INFORMATION: Xaa is any naturally occurring amino acid

<400> SEQUENCE: 14

Cys Xaa Xaa Xaa Xaa Xaa Cys Xaa Cys
1               5

```
<210> SEQ ID NO 15
<211> LENGTH: 30
<212> TYPE: DNA
<213> ORGANISM: Artificial
<220> FEATURE:
<223> OTHER INFORMATION: primer

<400> SEQUENCE: 15
ttcactcctg gttgtgaggg tagcggtaat                              30

<210> SEQ ID NO 16
<211> LENGTH: 30
<212> TYPE: DNA
<213> ORGANISM: Artificial
<220> FEATURE:
<223> OTHER INFORMATION: primer

<400> SEQUENCE: 16
gttttgacaa tcgcaattac cgctaccctc                              30

<210> SEQ ID NO 17
<211> LENGTH: 39
<212> TYPE: DNA
<213> ORGANISM: Artificial
<220> FEATURE:
<223> OTHER INFORMATION: primer

<400> SEQUENCE: 17
gtaatgtcga tttgcaaaac aacaagtacc aaactgtca                    39

<210> SEQ ID NO 18
<211> LENGTH: 34
<212> TYPE: DNA
<213> ORGANISM: Artificial
<220> FEATURE:
<223> OTHER INFORMATION: primer

<400> SEQUENCE: 18
cgctaccctc acaaccagga gtgaagttga tttc                         34

<210> SEQ ID NO 19
<211> LENGTH: 39
<212> TYPE: DNA
<213> ORGANISM: Artificial
<220> FEATURE:
<223> OTHER INFORMATION: primer

<400> SEQUENCE: 19
aaaaaaaaaa aaaaaaaaaa aaaaaaaaaa aaaaaaaa                     39

<210> SEQ ID NO 20
<211> LENGTH: 34
<212> TYPE: DNA
<213> ORGANISM: Artificial
<220> FEATURE:
<223> OTHER INFORMATION: primer

<400> SEQUENCE: 20
aaaaaaaaaa aaaaaaaaaa aaaaaaaaaa aaaa                         34

<210> SEQ ID NO 21
<211> LENGTH: 39
<212> TYPE: DNA
<213> ORGANISM: Artificial
<220> FEATURE:
```

<223> OTHER INFORMATION: primer

<400> SEQUENCE: 21
gtaatgtcga ttgtcaaaac aacaagtacc aaactgtca          39

<210> SEQ ID NO 22
<211> LENGTH: 34
<212> TYPE: DNA
<213> ORGANISM: Artificial
<220> FEATURE:
<223> OTHER INFORMATION: primer

<400> SEQUENCE: 22
cgctaccctc acaaccagga gtgaagttga tttc          34

<210> SEQ ID NO 23
<211> LENGTH: 39
<212> TYPE: DNA
<213> ORGANISM: Artificial
<220> FEATURE:
<223> OTHER INFORMATION: primer

<400> SEQUENCE: 23
gtaattgcga tttgcaaaac aacaagtacc aaactgtca          39

<210> SEQ ID NO 24
<211> LENGTH: 34
<212> TYPE: DNA
<213> ORGANISM: Artificial
<220> FEATURE:
<223> OTHER INFORMATION: primer

<400> SEQUENCE: 24
cgctaccctc ataaccagga gtgaagttga tttc          34

<210> SEQ ID NO 25
<211> LENGTH: 39
<212> TYPE: DNA
<213> ORGANISM: Artificial
<220> FEATURE:
<223> OTHER INFORMATION: primer

<400> SEQUENCE: 25
gtaatgtcga ttgtcaaaac aacaagtacc aaactgtca          39

<210> SEQ ID NO 26
<211> LENGTH: 34
<212> TYPE: DNA
<213> ORGANISM: Artificial
<220> FEATURE:
<223> OTHER INFORMATION: primer

<400> SEQUENCE: 26
cgctaccctc ataaccagga gtgaagttga tttc          34

<210> SEQ ID NO 27
<211> LENGTH: 39
<212> TYPE: DNA
<213> ORGANISM: Artificial
<220> FEATURE:
<223> OTHER INFORMATION: primer

<400> SEQUENCE: 27
gtaattgcga ttgtcaaaac aacaagtacc aaactgtca          39

<210> SEQ ID NO 28
<211> LENGTH: 34
<212> TYPE: DNA
<213> ORGANISM: Artificial
<220> FEATURE:
<223> OTHER INFORMATION: primer

<400> SEQUENCE: 28
cgctaccctc ataaccagga gtgaagttga tttc                                34

<210> SEQ ID NO 29
<211> LENGTH: 30
<212> TYPE: DNA
<213> ORGANISM: Artificial
<220> FEATURE:
<223> OTHER INFORMATION: primer

<400> SEQUENCE: 29
ttcactcctg gcagtgaggg tagcggtaat                                     30

<210> SEQ ID NO 30
<211> LENGTH: 29
<212> TYPE: DNA
<213> ORGANISM: Artificial
<220> FEATURE:
<223> OTHER INFORMATION: primer

<400> SEQUENCE: 30
ttttgcaaat cgacattacc gctaccctc                                      29

<210> SEQ ID NO 31
<211> LENGTH: 30
<212> TYPE: DNA
<213> ORGANISM: Artificial
<220> FEATURE:
<223> OTHER INFORMATION: primer

<400> SEQUENCE: 31
ttcactcctg gcgctgaggg tagcggtaat                                     30

<210> SEQ ID NO 32
<211> LENGTH: 29
<212> TYPE: DNA
<213> ORGANISM: Artificial
<220> FEATURE:
<223> OTHER INFORMATION: primer

<400> SEQUENCE: 32
ttttgcaaat cgacattacc gctaccctc                                      29

<210> SEQ ID NO 33
<211> LENGTH: 30
<212> TYPE: DNA
<213> ORGANISM: Artificial
<220> FEATURE:
<223> OTHER INFORMATION: primer

<400> SEQUENCE: 33
ttcactcctg gcgatgaggg tagcggtaat                                     30

<210> SEQ ID NO 34
<211> LENGTH: 29
<212> TYPE: DNA
<213> ORGANISM: Artificial
<220> FEATURE:
<223> OTHER INFORMATION: primer

```
<400> SEQUENCE: 34
ttttgcaaat cgacattacc gctaccctc                                    29

<210> SEQ ID NO 35
<211> LENGTH: 30
<212> TYPE: DNA
<213> ORGANISM: Artificial
<220> FEATURE:
<223> OTHER INFORMATION: primer

<400> SEQUENCE: 35
ttcactcctg gcactgaggg tagcggtaat                                   30

<210> SEQ ID NO 36
<211> LENGTH: 29
<212> TYPE: DNA
<213> ORGANISM: Artificial
<220> FEATURE:
<223> OTHER INFORMATION: primer

<400> SEQUENCE: 36
ttttgcaaat cgacattacc gctaccctc                                    29

<210> SEQ ID NO 37
<211> LENGTH: 30
<212> TYPE: DNA
<213> ORGANISM: Artificial
<220> FEATURE:
<223> OTHER INFORMATION: primer

<400> SEQUENCE: 37
agggtagcgg taatgccgat ttgcaaaaca                                   30

<210> SEQ ID NO 38
<211> LENGTH: 30
<212> TYPE: DNA
<213> ORGANISM: Artificial
<220> FEATURE:
<223> OTHER INFORMATION: primer

<400> SEQUENCE: 38
gacagtctgg tacttgttgt tttgcaaatc                                   30

<210> SEQ ID NO 39
<211> LENGTH: 30
<212> TYPE: DNA
<213> ORGANISM: Artificial
<220> FEATURE:
<223> OTHER INFORMATION: primer

<400> SEQUENCE: 39
agggtagcgg taatagcgat ttgcaaaaca                                   30

<210> SEQ ID NO 40
<211> LENGTH: 30
<212> TYPE: DNA
<213> ORGANISM: Artificial
<220> FEATURE:
<223> OTHER INFORMATION: primer

<400> SEQUENCE: 40
gacagtctgg tacttgttgt tttgcaaatc                                   30

<210> SEQ ID NO 41
<211> LENGTH: 30
```

<212> TYPE: DNA
<213> ORGANISM: Artificial
<220> FEATURE:
<223> OTHER INFORMATION: primer

<400> SEQUENCE: 41
agggtagcgg taataccgat ttgcaaaaca                              30

<210> SEQ ID NO 42
<211> LENGTH: 30
<212> TYPE: DNA
<213> ORGANISM: Artificial
<220> FEATURE:
<223> OTHER INFORMATION: primer

<400> SEQUENCE: 42
gacagtctgg tacttgttgt tttgcaaatc                              30

<210> SEQ ID NO 43
<211> LENGTH: 39
<212> TYPE: DNA
<213> ORGANISM: Artificial
<220> FEATURE:
<223> OTHER INFORMATION: primer

<400> SEQUENCE: 43
gtaattccga ttctcaaaac aacaagtacc aaactgtca                    39

<210> SEQ ID NO 44
<211> LENGTH: 34
<212> TYPE: DNA
<213> ORGANISM: Artificial
<220> FEATURE:
<223> OTHER INFORMATION: primer

<400> SEQUENCE: 44
cgctaccctc agaaccagga gtgaagttga tttc                         34

<210> SEQ ID NO 45
<211> LENGTH: 39
<212> TYPE: DNA
<213> ORGANISM: Artificial
<220> FEATURE:
<223> OTHER INFORMATION: primer

<400> SEQUENCE: 45
gtaatgacga tgatcaaaac aacaagtacc aaactgtca                    39

<210> SEQ ID NO 46
<211> LENGTH: 34
<212> TYPE: DNA
<213> ORGANISM: Artificial
<220> FEATURE:
<223> OTHER INFORMATION: primer

<400> SEQUENCE: 46
cgctaccctc atcaccagga gtgaagttga tttc                         34

<210> SEQ ID NO 47
<211> LENGTH: 30
<212> TYPE: DNA
<213> ORGANISM: Artificial
<220> FEATURE:
<223> OTHER INFORMATION: primer

<400> SEQUENCE: 47

```
ggtagcggaa atcgggatca tcaaaacaac                                  30

<210> SEQ ID NO 48
<211> LENGTH: 30
<212> TYPE: DNA
<213> ORGANISM: Artificial
<220> FEATURE:
<223> OTHER INFORMATION: primer

<400> SEQUENCE: 48
atggttgaca gtttggtact tgttgttttg                                  30

<210> SEQ ID NO 49
<211> LENGTH: 30
<212> TYPE: DNA
<213> ORGANISM: Artificial
<220> FEATURE:
<223> OTHER INFORMATION: primer

<400> SEQUENCE: 49
ggtagcggaa atagcgatca tcaaaacaac                                  30

<210> SEQ ID NO 50
<211> LENGTH: 30
<212> TYPE: DNA
<213> ORGANISM: Artificial
<220> FEATURE:
<223> OTHER INFORMATION: primer

<400> SEQUENCE: 50
atggttgaca gtttggtact tgttgttttg                                  30

<210> SEQ ID NO 51
<211> LENGTH: 30
<212> TYPE: DNA
<213> ORGANISM: Artificial
<220> FEATURE:
<223> OTHER INFORMATION: primer

<400> SEQUENCE: 51
ttcactccgg gtcacgaggg tagcggaaat                                  30

<210> SEQ ID NO 52
<211> LENGTH: 30
<212> TYPE: DNA
<213> ORGANISM: Artificial
<220> FEATURE:
<223> OTHER INFORMATION: primer

<400> SEQUENCE: 52
gttttgtgaa tcgtgatttc cgctaccctc                                  30

<210> SEQ ID NO 53
<211> LENGTH: 1896
<212> TYPE: DNA
<213> ORGANISM: Mucor DR056860

<400> SEQUENCE: 53
atgcgtctct ctgtggcgat cctcactctc acttcggctc tggcttcggt tacctcggcc    60
caacaaaaca atactgatac ttatgactac gtgatcgtcg gaggaggagt gggtggactg   120
gctctcgctt cgcgcctctc cgaggataag aacgttaccg tggctgtcct ggaatcgggc   180
ccttatgcgg atgacaaatt cgtggtctac gccccaggga tgtatggtca ggctgtcgga   240
actgacctgt gtcctctgct cccaacggtt cctcaaccat ctatgaacaa tcgaaccatc   300
```

```
actattgcta cgggacgtct gctcggagga ggttcagctg tgaacggact ggtctggacc    360
cgtggagcta tgaaggattt cgacgcttgg caggagctgg gaaacccagg atggaatggg    420
accactatgt tcaagtactt caagaaaatc gaaaacttcc atccccgac cgaggaacag     480
attcaatacg gcgctactta taacaagtct gtccacggtt tcaatggccc gatcgatatt    540
gcctttcccg tgttcgagtt tccgcagtct gctaactgga atgcgtcact ggcccatctc    600
aacttcaccc gccggcaaga tctgctcgac ggtagtctcc acggctacag cacgacccct    660
aacaccctga atccacagac tgcccgacgt gcggatgcct acgctggata tatccaacct    720
aacgtcaatc gaacgaacct ggctgtcctc gcgaatcata ccgttagtcg catccagttt    780
gaggcgcgga acgtagccaa accactgaag gccattggcg tggaatggta tactacgggc    840
ggagacaaga ctagtaaaca gacgatcaag gcgcgccggg agatcattct gagtagcgga    900
gccattgggt cgcctaagct gctcgaagtg tccgggatcg gtaacaaagc cattgttacc    960
gccgctggag tgcagtctct gatcgatctc caggcgttg gatcaaacat gcaagaccat    1020
gtgcacgctg ttaccgtgtc gaccactaat atcgatgggt acacgaccaa ctccgtgttc    1080
acgaatgaga ccctcgccca ggaacaaaag gacctgtact acaacaacaa gactggaatc    1140
tggactacga cccctaacaa tctcgggtat cccagtccga gccagctgtt caccaacact    1200
acgtttaagt ctggcaaaga gtttgcggcc atgatccgca acagtactga taagtacgcc    1260
cagtactatg ctgcgaacaa tgctacgaac gtcgagctgc tcaagaaaca atatagtatc    1320
gtggcccgac gttacgagga aaactacatc agccctatcg aaatcaactt cacgccagga    1380
tacggggta ccgggatggc tgatctgcag aacaagaaat atcaaaccgt gaatcatgtc    1440
ctggttgccc ccctcagtcg gggctacact cacatcaact cgtccgatat tgaggacccc    1500
gttgtgatcg acccgcagta ctatagccat ccgctggatg tggacgtcca cgttgcgagt    1560
acccaactgg cccgaagcat cctcaacgcc cccggactgg cttctattaa ttcaggcgag    1620
gtggaaccgg gcgagaaggt ccagagcgat gaagacgttc gcaaatggct gtcggataac    1680
gtgcgttccg actggcatcc agtcggaacc tgcgctatgc tgccacgaaa gctcggagga    1740
gtcgttgatt cgaagctcaa agtctacggc accgcgaatc tgcgtatcgt tgacgcctcc    1800
atcattccgc tcgagatttc ttcacacctg atgcaaccag tctatgcggt ctccgaacgg    1860
gctgccgaca tcatcaaatc ctcctctaaa aaataa                              1896
```

<210> SEQ ID NO 54
<211> LENGTH: 39
<212> TYPE: DNA
<213> ORGANISM: Artificial
<220> FEATURE:
<223> OTHER INFORMATION: primer

<400> SEQUENCE: 54

```
ggatgtgtga ttgccagaac aagaaatatc aaaccgtga                           39
```

<210> SEQ ID NO 55
<211> LENGTH: 36
<212> TYPE: DNA
<213> ORGANISM: Artificial
<220> FEATURE:
<223> OTHER INFORMATION: primer

<400> SEQUENCE: 55

```
cggtaccccc gcatcctggc gtgaagttga tttcga                              36
```